United States Patent
Bruns, Jr. et al.

(10) Patent No.: US 7,268,125 B2
(45) Date of Patent: Sep. 11, 2007

(54) β-LACTAMYL VASOPRESSIN V$_{1A}$ ANTAGONISTS

(75) Inventors: Robert F. Bruns, Jr., Carmel, IN (US); Christophe D. G. Guillon, Bethlehem, PA (US); Ned D. Heindel, Easton, PA (US); Gary A. Koppel, Indianapolis, IN (US); Marvin J. Miller, South Bend, IN (US)

(73) Assignee: Azevan Pharmaceuticals, Inc., Bethlehem, PA (US)

( * ) Notice: Subject to any disclaimer, the term of this patent is extended or adjusted under 35 U.S.C. 154(b) by 0 days.

(21) Appl. No.: 11/442,788

(22) Filed: May 30, 2006

(65) Prior Publication Data
US 2006/0217364 A1    Sep. 28, 2006

Related U.S. Application Data

(63) Continuation of application No. 10/492,323, filed as application No. PCT/US2002/032433 on Oct. 11, 2002, now Pat. No. 7,119,083.

(60) Provisional application No. 60/329,054, filed on Oct. 12, 2001.

(51) Int. Cl.
  C07D 413/04      (2006.01)
  C07D 413/14      (2006.01)
  C07D 205/085     (2006.01)
  C07D 403/04      (2006.01)
  A61K 31/496      (2006.01)

(52) U.S. Cl. .................. 514/210.02; 540/363; 540/364

(58) Field of Classification Search ........... 514/210.02; 540/363, 364
See application file for complete search history.

(56) References Cited

U.S. PATENT DOCUMENTS

| | | |
|---|---|---|
| 5,759,865 A | 6/1998 | Bruns, Jr. et al. |
| 6,204,260 B1 | 3/2001 | Bruns, Jr. et al. |
| 6,627,625 B1 | 9/2003 | Koppel |

FOREIGN PATENT DOCUMENTS

WO    WO97/30707    8/1997

OTHER PUBLICATIONS

Hirai et al, "An Example of the β-Lactam Ring Formation and Novel Pyrrolinoazetidinone Ring Construction", *Sankyo Kenyusho Nempo*, vol. 37, pp. 133-139, (1985).

Ojima et al., "Asymmetric Alkylations of a Phenylalanylglycinate Equivalent. New Routes to Dipeptides Bearing α-Alkyl-α-amino Acid Residues", *J. Amer. Chem. Soc.*, vol. 112, pp. 770-774, (1990).

*Primary Examiner*—Mark L. Berch
(74) *Attorney, Agent, or Firm*—Barnes & Thornburg LLP

(57) ABSTRACT

Novel 2-(azetidin-2-on-1-yl)alkanedioic acid derivatives and 2-(azetidin-2-on-1-yl)alkoxyalkanoic acid derivatives are described for use in the treatment of disease states responsive to antagonism of the vasopressin V$_{1a}$ receptor

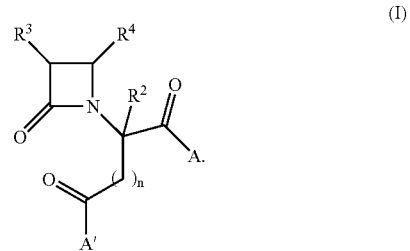

70 Claims, No Drawings

β-LACTAMYL VASOPRESSIN $V_{1A}$ ANTAGONISTS

CROSS-REFERENCE TO RELATED APPLICATIONS

This application is a continuation of U.S. patent application Ser. No. 10/492,323, filed Jun. 15, 2004, now U.S. Pat. No. 7,119,083 which is the U.S. national counterpart application of International Application No. PCT/US2002/032433 filed Oct. 11, 2002, which claims priority to U.S. Provisional Patent Application No. 60/329,054, filed Oct. 12, 2001, the entirety of the disclosures of which are incorporated herein by reference.

GOVERNMENT RIGHTS

This invention was made with support from NIH Grant Nos. R41 HD37290 and R42 HD37290; the government may have certain rights in this invention.

FIELD OF THE INVENTION

The present invention relates to novel 2-(azetidin-2-on-1-yl)alkanedioic acid derivatives as vasopressin $V_{1a}$ receptor antagonists. The present invention also relates to methods of treating mammals in need of relief from disease states associated with and responsive to the antagonism of the vasopressin $V_{1a}$ receptor.

BACKGROUND OF THE INVENTION

Vasopressin, a neurohypophyseal neuropeptide produced in the hypothalamus, is involved in water metabolism homeostasis, renal function, mediation of cardiovascular function, non-opioid mediation of tolerance for pain, and regulation of temperature in mammals. In addition to being released into the circulation via the posterior pituitary, vasopressin acts as a neurotransmitter in the brain. Three vasopressin receptor subtypes, designated $V_{1a}$, $V_{1b}$, and $V_2$ have been identified. The human $V_{1a}$ receptor has been cloned (Thibonnier et al., *The Journal of Biological Chemistry*, 269(5), 3304-3310 (1994)), and has been shown by radioligand binding techniques to be present in vascular smooth muscle cells, hepatocytes, blood platelets, lymphocytes and monocytes, type II pneumocytes, adrenal cortex, brain, reproductive organs, retinal epithelium, renal mesangial cells, and the A10, A7r5, 3T3 and WRK-1 cell lines (Thibonnier, *Neuroendocrinology of the Concepts in Neurosurgery Series* 5, (Selman, W., ed), 19-30, Williams and Wilkins, Baltimore, (1993)).

Structural modification of vasopressin has provided a number of vasopressin agonists (Sawyer, *Pharmacol. Reviews*, 13, 255 (1961)). In addition, several potent and selective vasopressin peptide antagonists have been designed (Lazslo et al., *Pharmacological Reviews*, 43, 73-108 (1991); Mah and Hofbauer, *Drugs of the Future*, 12, 1055-1070 (1987); Manning and Sawyer, *Trends in Neuroscience*, 7, 8-9 (1984)). Their lack of oral bioavailability and short half-life, however, have limited the therapeutic potential of these analogs. While novel structural classes of non-peptidyl vasopressin $V_{1a}$ antagonists have been discovered (Yamamura et al., *Science*, 275, 572-574 (1991); Serradiel-Le Gal et al., *Journal of Clinical Investigation*, 92, 224-231 (1993); Serradiel-Le Gal et al., *Biochemical Pharmacology*, 47(4), 633-641 (1994)), a clinical candidate has yet to be identified.

The general structural class of substituted 2-(azetidin-2-on-1-yl)acetic acid esters and amides are known as synthetic intermediates for the preparation of β-lactam antibiotics (see e.g. U.S. Pat. No. 4,751,299).

SUMMARY OF THE INVENTION

It has been found that certain compounds within the general class of 2-(azetidin-2-on-1-yl)alkanedioic acid derivatives elicit activity at the vasopressin $V_{1a}$ receptor. The present invention describes novel 2-(azetidin-2-on-1-yl)alkanedioic acid esters and amides useful for treating disease states that are associated with and responsive to antagonism of a vasopressin $V_{1a}$ receptor in a mammal.

The invention also describes a method for treating a disease state responsive to the antagonism of a vasopressin $V_{1a}$ receptor, in a mammal in need of such treatment, comprising the step of administering to the mammal a pharmaceutically effective amount of such 2-(azetidin-2-on-1-yl)alkanedioic acid derivatives.

In particular, the present invention describes compounds having the formula I:

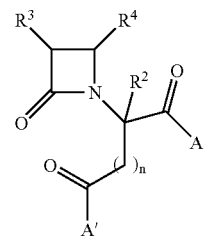

wherein:
n is an integer from 0 to 2;
A is $R^6O$—, monosubstituted amino, or disubstituted amino;
A' is $R^{6'}O$—, monosubstituted amino, or disubstituted amino;
$R^2$ is hydrogen or $C_1$-$C_6$ alkyl;
$R^3$ is a structure selected from the group consisting of

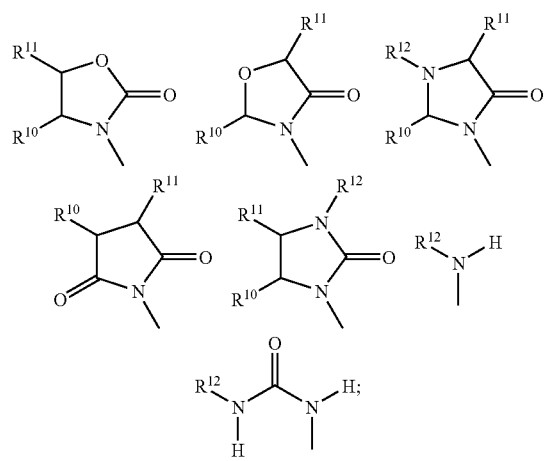

$R^4$ is $C_1$-$C_6$ alkyl, $C_2$-$C_6$ alkenyl, $C_2$-$C_6$ alkynyl, $C_3$-$C_8$ cycloalkyl, $C_3$-$C_9$ cycloalkenyl, limonenyl, pinenyl, $C_1$-$C_3$ alkanoyl, optionally-substituted aryl, optionally-substituted aryl($C_1$-$C_4$ alkyl), optionally-substituted aryl($C_2$-$C_4$ alkenyl), or optionally-substituted aryl ($C_2$-$C_4$ alkynyl);

$R^6$ and $R^{6'}$ are each independently selected from the group consisting of $C_1$-$C_6$ alkyl, $C_3$-$C_8$ cycloalkyl, ($C_1$-$C_4$ alkoxy)-($C_1$-$C_4$ alkyl), optionally-substituted aryl ($C_1C_4$ alkyl), a first heterocycle Y—, Y—($C_1$-$C_4$ alkyl), a second heterocycle Y'—, Y'—($C_1$-$C_4$ alkyl), $R^7R^8N$—($C_2$-$C_4$ alkyl), and $R^{7'}R^{8'}N$—($C_2$-$C_4$ alkyl);

where the first heterocycle Y and the second heterocycle Y' are each independently selected from the group consisting of tetrahydrofuryl, morpholinyl, pyrrolidinyl, piperidinyl, piperazinyl, homopiperazinyl, or quinuclidinyl; where said morpholinyl, pyrrolidinyl, piperidinyl, piperazinyl, homopiperazinyl, or quinuclidinyl is optionally N-substituted with $C_1$-$C_4$ alkyl or optionally-substituted aryl($C_1$-$C_4$ alkyl);

$R^7$ is hydrogen or $C_1$-$C_6$ alkyl;

$R^8$ is $C_1$-$C_6$ alkyl, $C_3$-$C_8$ cycloalkyl, optionally-substituted aryl, or optionally-substituted aryl($C_1$-$C_4$ alkyl); or $R^7$ and $R^8$ are taken together with the attached nitrogen atom to form an heterocycle selected from the group consisting of pyrrolidinyl, piperidinyl, morpholinyl, piperazinyl, and homopiperazinyl; where said piperazinyl or homopiperazinyl is optionally N-substituted with $R^{12}$;

$R^{7'}$ is hydrogen or $C_1$-$C_6$ alkyl;

$R^{8'}$ is $C_1$-$C_6$ alkyl, $C_3$-$C_8$ cycloalkyl, optionally-substituted aryl, or optionally-substituted aryl($C_1$-$C_4$ alkyl); or $R^{7'}$ and $R^{8'}$ are taken together with the attached nitrogen atom to form an heterocycle selected from the group consisting of pyrrolidinyl, piperidinyl, morpholinyl, piperazinyl, and homopiperazinyl; where said piperazinyl or homopiperazinyl is optionally N-substituted with $R^{12'}$;

$R^{10}$ and $R^{11}$ are each independently chosen from the group consisting of hydrogen, $C_1$-$C_6$ alkyl, $C_3$-$C_8$ cycloalkyl, $C_1$-$C_4$ alkoxycarbonyl, $C_1$-$C_5$ alkanoyloxy, benzyloxy, benzoyloxy, diphenylmethoxy, triphenylmethoxy, optionally-substituted aryl, and optionally-substituted aryl($C_1$-$C_4$ alkyl);

where the $C_1$-$C_6$ alkyl or the $C_3$-$C_8$ cycloalkyl is optionally monosubstituted with a substituent selected from the group consisting of hydroxy, protected carboxy, carbamoyl, thiobenzyl and $C_1$-$C_4$ thioalkyl; and, where the benzyl of said benzyloxy or said benzoyloxy is optionally substituted with one or two substituents independently selected from the group consisting of $C_1$-$C_4$ alkyl, $C_1$-$C_4$ alkoxy, halogen, hydroxy, cyano, carbamoyl, amino, mono($C_1$-$C_4$ alkyl)amino, di($C_1$-$C_4$ alkyl)amino, $C_1$-$C_4$ alkylsulfonylamino, and nitro;

$R^{12}$ and $R^{12'}$ are each independently selected from the group consisting of hydrogen, $C_1$-$C_6$ alkyl, $C_3$-$C_8$ cycloalkyl, $C_1$-$C_4$ alkoxycarbonyl, optionally-substituted aryloxycarbonyl, optionally-substituted aryl ($C_1$-$C_4$ alkyl), and optionally-substituted aryloyl; and hydrates, solvates and pharmaceutically acceptable acid addition salts thereof, and providing that:

a) when A is $R^6O$—, then A' is not benzylamino or substituted benzylamino;

b) when A is $R^6O$— and the integer n is 0, then A' is not $R^6O$—; and c) when A is monosubstituted amino and the integer n is 0, then A' is not anilinyl, substituted anilinyl, benzylamino, or substituted benzylamino.

In addition, the present invention describes compounds having the formula II:

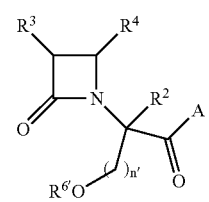

wherein:

n' is an integer from 1 to 3;

A is $R^6O$—, monosubstituted amino, or disubstituted amino;

$R^2$ is hydrogen or $C_1$-$C_6$ alkyl;

$R^3$ is a structure selected from the group consisting of

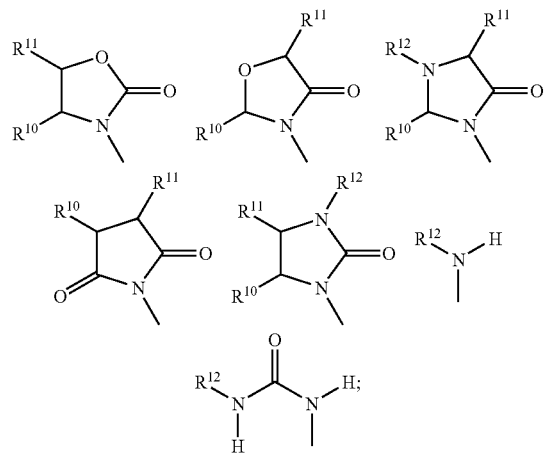

$R^4$ is $C_1$-$C_6$ alkyl, $C_2$-$C_6$ alkenyl, $C_2$-$C_6$ alkynyl, $C_3$-$C_8$ cycloalkyl, $C_3$-$C_9$ cycloalkenyl, limonenyl, pinenyl, $C_1$-$C_3$ alkanoyl, optionally-substituted aryl, optionally-substituted aryl($C_1$-$C_4$ alkyl), optionally-substituted aryl(halo $C_1$-$C_4$ alkyl), optionally-substituted aryl(alkoxy $C_1$-$C_4$ alkyl), optionally-substituted aryl($C_2$-$C_4$ alkenyl), optionally-substituted aryl(halo $C_2$-$C_4$ alkenyl), or optionally-substituted aryl($C_2$-$C_4$ alkynyl);

$R^6$ is selected from the group consisting of $C_1$-$C_6$ alkyl, $C_3$-$C_8$ cycloalkyl, ($C_1$($C_1$-$C_4$ alkoxy)-($C_1$-$C_4$ alkyl), optionally-substituted aryl($C_1$-$C_4$ alkyl), a first heterocycle Y—, Y—($C_1$-$C_4$ alkyl), and $R^7R^8N$—($C_2$-$C_4$ alkyl);

where the first heterocycle Y is selected from the group consisting of tetrahydrofuryl, morpholinyl, pyrrolidinyl, piperidinyl, piperazinyl, homopiperazinyl, or quinuclidinyl; where said morpholinyl, pyrrolidinyl, piperidinyl, piperazinyl, homopiperazinyl, or quinuclidinyl is optionally N-substituted with $C_1$-$C_4$ alkyl or optionally-substituted aryl($C_1$-$C_4$ alkyl);

$R^{6'}$ is selected from the group consisting of $C_1$-$C_6$ alkyl, $C_3$-$C_8$ cycloalkyl, ($C_1$-$C_4$ alkoxy)-($C_1$-$C_4$ alkyl), optionally-substituted aryl($C_1$-$C_4$ alkyl), Y'—($C_1$-$C_4$ alkyl), where Y'— is a second heterocycle, and $R^7R^8N$—($C_2$-$C_4$ alkyl);
  where the second heterocycle Y' is selected from the group consisting of tetrahydrofuryl, morpholinyl, pyrrolidinyl, piperidinyl, piperazinyl, homopiperazinyl, or quinuclidinyl; where said morpholinyl, pyrrolidinyl, piperidinyl, piperazinyl, homopiperazinyl, or quinuclidinyl is optionally N-substituted with $C_1$-$C_4$ alkyl or optionally-substituted aryl($C_1$-$C_4$ alkyl);
$R^7$ is hydrogen or $C_1$-$C_6$ alkyl;
$R^8$ is $C_1$-$C_6$ alkyl, $C_3$-$C_8$ cycloalkyl, optionally-substituted aryl, or optionally-substituted aryl($C_1$-$C_4$ alkyl); or
  $R^7$ and $R^8$ are taken together with the attached nitrogen atom to form an heterocycle selected from the group consisting of pyrrolidinyl, piperidinyl, morpholinyl, piperazinyl, and homopiperazinyl; where said piperazinyl or homopiperazinyl is optionally N-substituted with $R^{12}$;
$R^{7'}$ is hydrogen or $C_1$-$C_6$ alkyl;
$R^{8'}$ is $C_1$-$C_6$ alkyl, $C_3$-$C_8$ cycloalkyl, optionally-substituted aryl, or optionally-substituted aryl($C_1$-$C_4$ alkyl); or
  $R^{7'}$ and $R^{8'}$ are taken together with the attached nitrogen atom to form an heterocycle selected from the group consisting of pyrrolidinyl, piperidinyl, morpholinyl, piperazinyl, and homopiperazinyl; where said piperazinyl or homopiperazinyl is optionally N-substituted with $R^{12'}$;
$R^{10}$ and $R^{11}$ are each independently chosen from the group consisting of hydrogen, $C_1$-$C_6$ alkyl, $C_3$-$C_8$ cycloalkyl, $C_1$-$C_4$ alkoxycarbonyl, $C_1$-$C_5$ alkanoyloxy, benzyloxy, benzoyloxy, diphenylmethoxy, triphenylmethoxy, optionally-substituted aryl, and optionally-substituted aryl($C_1$-$C_4$ alkyl);
  where the $C_1$-$C_6$ alkyl or the $C_3$-$C_8$ cycloalkyl is optionally monosubstituted with a substituent selected from the group consisting of hydroxy, protected carboxy, carbamoyl, thiobenzyl and $C_1$-$C_4$ thioalkyl; and,
where the benzyl of said benzyloxy or said benzoyloxy is optionally substituted with one or two substituents independently selected from the group consisting of $C_1$-$C_4$ alkyl, $C_1$-$C_4$ alkoxy, halogen, hydroxy, cyano, carbamoyl, amino, mono($C_1$-$C_4$ alkyl)amino, di($C_1$-$C_4$ alkyl)amino, $C_1$-$C_4$ alkylsulfonylamino, and nitro;
$R^{12}$ and $R^{12'}$ are each independently selected from the group consisting of hydrogen, $C_1$-$C_6$ alkyl, $C_3$-$C_8$ cycloalkyl, $C_1$-$C_4$ alkoxycarbonyl, optionally-substituted aryloxycarbonyl, optionally-substituted aryl($C_1$-$C_4$ alkyl), and optionally-substituted aryloyl; and
hydrates, solvates and pharmaceutically acceptable acid addition salts thereof.

Illustrative compounds of formula I and II are described, wherein A is an acyclic disubstituted amino.

Illustrative compounds of formula I and II are described 1, wherein A is a cyclic disubstituted amino.

Illustrative compounds of formula I and II are described, wherein A is a monosubstituted amino having the formula XNH—, where X is selected from the group consisting of $C_1$-$C_6$ alkyl, $C_3$-$C_8$ cycloalkyl, ($C_1$-$C_4$ alkoxy)-($C_1$-$C_4$ alkyl), optionally-substituted aryl, optionally-substituted aryl($C_1$-$C_4$ alkyl), the first heterocycle Y, Y—($C_1$-$C_4$ alkyl), $R^7R^8N$—, and $R^7R^8N$—($C_2$-$C_4$ alkyl).

Illustrative compounds of formula I and II are described, wherein A is a disubstituted amino having the formula $R^5XN$—; where $R^5$ is selected from the group consisting of hydroxy, $C_1$-$C_6$ alkyl, $C_1$-$C_4$ alkoxycarbonyl, and benzyl; and where X is selected from the group consisting of $C_1$-$C_6$ alkyl, $C_3$-$C_8$ cycloalkyl, ($C_1$-$C_4$ alkoxy)-($C_1$-$C_4$ alkyl), optionally-substituted aryl, optionally-substituted aryl ($C_1$-$C_4$ alkyl), the first heterocycle Y, Y—($C_1$-$C_4$ alkyl), $R^7R^8N$—, and $R^7R^8N$—($C_2$-$C_4$ alkyl).

Illustrative compounds of formula I and II are described, wherein A is a disubstituted amino having the formula $R^5XN$—, where $R^5$ and X are taken together with the attached nitrogen atom to form an heterocycle selected from the group consisting of pyrrolidinyl, piperidinyl, piperazinyl, and homopiperazinyl;
  where the heterocycle is optionally substituted with $R^{10}$, $R^{12}$, $R^7R^8N$—, or $R^7R^8N$—($C_1$-$C_4$ alkyl) as defined above.

Illustrative compounds of formula I and II are described, wherein $R^5$ and X are taken together with the attached nitrogen atom to form piperidinyl optionally substituted, at the 4-position with hydroxy, $C_1$-$C_6$ alkyl, $C_3$-$C_8$ cycloalkyl, $C_1$-$C_4$ alkoxy, ($C_1$-$C_4$ alkoxy)carbonyl, (hydroxy($C_2$-$C_4$ alkyloxy))-($C_2$-$C_4$ alkyl), $R^7R^8N$—, $R^7R^8N$—($C_1$-$C_4$ alkyl), diphenylmethyl, optionally-substituted aryl, optionally-substituted aryl($C_1$-$C_4$ alkyl), or piperidin-1-yl($C_1$-$C_4$ alkyl).

Illustrative compounds of formula I and II are described, wherein $R^5$ and X are taken together with the attached nitrogen atom to form piperazinyl optionally substituted at the 4-position with $C_1$-$C_6$ alkyl, $C_3$-$C_8$ cycloalkyl, optionally-substituted aryl, optionally-substituted aryl($C_1$-$C_4$ alkyl), α-methylbenzyl, N—($C_1$-$C_5$ alkyl) acetamid-2-yl, N—($C_3$-$C_8$ cycloalkyl) acetamid-2-yl, $R^7R^8N$—, or ($C_1$-$C_4$ alkoxy)carbonyl.

Illustrative compounds of formula I and II are described, wherein $R^5$ and X are taken together with the attached nitrogen atom to form homopiperazinyl optionally substituted in the 4-position with $C_1$-$C_4$ alkyl, aryl, or aryl($C_1$-$C_4$ alkyl).

Illustrative compounds of formula I and II are described, wherein A is a disubstituted amino having the formula $R^5XN$—, where $R^5$ and X are taken together with the attached nitrogen atom to form an heterocycle selected from the group consisting of pyrrolidinonyl, piperidinonyl, 2-(pyrrolidin-1-ylmethyl)pyrrolidin-1-yl, 1,2,3,4-tetrahydroisoquinolin-2-yl.

Illustrative compounds of formula I are described, wherein A' is an acyclic disubstituted amino.

Illustrative compounds of formula I are described, wherein A' is a cyclic disubstituted amino.

Illustrative compounds of formula I are described, wherein A' is a monosubstituted amino having the formula X'NH—; where X' is selected from the group consisting of $C_1$-$C_6$ alkyl, $C_3$-$C_8$ cycloalkyl, ($C_1$-$C_4$ alkoxy)-($C_1$-$C_4$ alkyl), optionally -substituted aryl, optionally-substituted aryl($C_1$-$C_4$ alkyl), the second heterocycle Y', Y'—($C_1$-$C_4$ alkyl), $R^7R^8N$—, and $R^7R^8N$—($C_2$-$C_4$ alkyl).

Illustrative compounds of formula I are described, wherein A' is a disubstituted amino having the formula $R^{5'}X'N$—; where $R^{5'}$ is selected from the group consisting of hydroxy, $C_1$-$C_6$ alkyl, $C_1$-$C_4$ alkoxycarbonyl, and benzyl; and X' is selected from the group consisting of $C_1$-$C_6$ alkyl, $C_3$-$C_8$ cycloalkyl, ($C_1$-$C_4$ alkoxy)-($C_1$-$C_4$ alkyl), optionally-substituted aryl, optionally-substituted aryl($C_1$-$C_4$ alkyl), the second heterocycle Y', Y'—($C_1$-$C_4$ alkyl), $R^7R^8N$—, and $R^7R^8N$—($C_2$-$C_4$ alkyl).

Illustrative compounds of formula I are described, wherein A' is a disubstituted amino having the formula $R^{5'}X'N$—, where $R^{5'}$ and X' are taken together with the attached nitrogen atom to form an heterocycle selected from the group consisting of pyrrolidinyl, piperidinyl, piperazinyl, and homopiperazinyl;

where the heterocycle is optionally substituted with $R^{10'}$, $R^{12'}$, $R^{7'}R^{8'}N$—, or $R^{7'}R^{8'}N$—$(C_1$-$C_4$ alkyl) as defined above.

Illustrative compounds of formula I are described, wherein $R^{5'}$ and X' are taken together with the attached nitrogen atom to form piperidinyl optionally substituted at the 4-position with hydroxy, $C_1$-$C_6$ alkyl, $C_3$-$C_8$ cycloalkyl, $C_1$-$C_4$ alkoxy, $(C_1$-$C_4$ alkoxy)carbonyl, (hydroxy($C_1$-$C_4$ alkyloxy))-($C_1$-$C_4$ alkyl), $R^7R^8N$—, $R^7R^8N$—$(C_1$-$C_4$ alkyl), diphenylmethyl, optionally-substituted aryl, optionally-substituted aryl($C_1$-$C_4$ alkyl), or piperidin-1-yl($C_1$-$C_4$ alkyl).

Illustrative compounds of formula I are described, wherein $R^{5'}$ and X' are taken together with the attached nitrogen atom to form piperazinyl optionally substituted at the 4-position with $C_1$-$C_6$ alkyl, $C_3$-$C_8$ cycloalkyl, optionally-substituted aryl, optionally-substituted aryl($C_1$-$C_4$ alkyl), α-methylbenzyl, N—$(C_1$-$C_5$ alkyl) acetamid-2-yl, N—$(C_3$-$C_8$ cycloalkyl) acetamid-2-yl, $R^7R^8N$—, or $(C_1$-$C_4$ alkoxy)carbonyl.

Illustrative compounds of formula I are described, wherein $R^{5'}$ and X' are taken together with the attached nitrogen atom to form homopiperazinyl optionally substituted in the 4-position with $C_1$-$C_4$ alkyl, aryl, or aryl($C_1$-$C_4$ alkyl).

Illustrative compounds of formula I are described, wherein A' is a disubstituted amino having the formula $R^{5'}X'N$—, where $R^{5'}$ and X' are taken together with the attached nitrogen atom to form an heterocycle selected from the group consisting of pyrrolidinonyl, piperidinonyl, 2-(pyrrolidin-1-ylmethyl)pyrrolidin-1-yl, 1,2,3,4-tetrahydroisoquinolin-2-yl.

Illustrative compounds of formula I and II are described, wherein $R^4$ is optionally-substituted aryl($C_1$-$C_4$ alkyl), optionally-substituted aryl($C_2$-$C_4$ alkenyl), or optionally-substituted aryl($C_2$-$C_4$ alkynyl).

Illustrative compounds of formula I and II are described, wherein $R^3$ is the structure

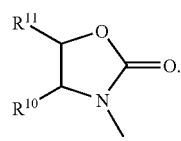

Illustrative compounds of formula I and II are described, wherein $R^2$ is hydrogen.

Illustrative compounds of formula I and II are described, wherein A is a disubstituted amino having the formula $R^5XN$—, where $R^5$ and X are taken together with the attached nitrogen atom to form an heterocycle selected from the group consisting of pyrrolidinyl, piperidinyl, and piperazinyl; where said heterocycle is optionally substituted with $C_1$-$C_6$ alkyl, $C_3$-$C_8$ cycloalkyl, $R^7R^8N$—, $R^7R^8N$—$(C_1$-$C_4$ alkyl), optionally-substituted aryl, or optionally-substituted aryl($C_1$-$C_4$ alkyl).

Illustrative compounds of formula I and II are described, wherein A is a monosubstituted amino having the formula XNH—, where X is optionally-substituted aryl($C_1$-$C_4$ alkyl).

Illustrative compounds of formula I and II are described, wherein:

$R^4$ is optionally-substituted aryl($C_1$-$C_4$ alkyl), optionally-substituted aryl($C_2$-$C_4$ alkenyl), or optionally-substituted aryl($C_2$-$C_4$ alkynyl);

$R^3$ is the structure

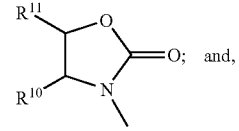

$R^2$ is hydrogen.

Illustrative compounds of formula I are described, wherein A' is $R^{6'}O$—, where $R^{6'}$ is $C_1$-$C_6$ alkyl.

Illustrative compounds of formula I are described, wherein A' is a monosubstituted amino having the formula X'NH—, where X' is optionally-substituted aryl($C_1$-$C_4$ alkyl), the second heterocycle Y', Y'—$(C_1$-$C_4$ alkyl), $R^{7'}R^{8'}N$—, or $R^{7'}R^{8'}N$—$(C_2$-$C_4$ alkyl).

Illustrative compounds of formula I are described, wherein X' is $R^{7'}R^{8'}N$— or $R^{7'}R^{8'}N$—$(C_2$-$C_4$ alkyl).

Illustrative compounds of formula I are described, wherein X' is the second heterocycle Y' or Y'—$(C_1$-$C_4$ alkyl), where the second heterocycle Y' is selected from the group consisting of pyrrolidinyl, piperidinyl, morpholinyl, piperazinyl, and homopiperazinyl, where said second heterocycle is optionally N-substituted with optionally-substituted aryl($C_1$-$C_4$ alkyl).

Illustrative compounds of formula I and II are described, wherein $R^{8'}$ is selected from the group consisting of $C_1$-$C_6$ alkyl, $C_3$-$C_8$ cycloalkyl, and aryl($C_1$-$C_4$ alkyl).

Illustrative compounds of formula I and II are described, wherein $R^{7'}$ and $R^{8'}$ are taken together with the attached nitrogen atom to form an heterocycle selected from the group consisting of pyrrolidinyl, piperidinyl, morpholinyl, piperazinyl, and homopiperazinyl, where said piperazinyl or homopiperazinyl is optionally substituted at the 4-position with ($C_1$-$C_4$ alkyl), ($C_3$-$C_8$ cycloalkyl), or aryl($C_1$-$C_4$ alkyl).

Illustrative compounds of formula I are described, wherein A' is a disubstituted amino having the formula $R^{5'}X'N$—.

Illustrative compounds of formula I are described, wherein $R^{5'}$ is aryl($C_1$-$C_4$ alkyl), and X' is selected from the group consisting of optionally-substituted aryl($C_1$-$C_4$ alkyl), the second heterocycle Y', Y'—$(C_1$-$C_4$ alkyl), $R^{7'}R^{8'}N$—, and $R^{7'}R^{8'}N$—$(C_2$-$C_4$ alkyl).

Illustrative compounds of formula I and II are described, wherein $R^{8'}$ is selected from the group consisting of $C_1$-$C_6$ alkyl, $C_3$-$C_8$ cycloalkyl, and aryl($C_1$-$C_4$ alkyl).

Illustrative compounds of formula I and II are described, wherein $R^{7'}$ and $R^{8'}$ are taken together with the attached nitrogen atom to form an heterocycle selected from the group consisting of pyrrolidinyl, piperidinyl, morpholinyl, piperazinyl, and homopiperazinyl, where said piperazinyl or homopiperazinyl is optionally substituted at the 4-position with ($C_1$-$C_4$ alkyl), ($C_3$-$C_8$ cycloalkyl), or aryl($C_1$-$C_4$ alkyl).

Illustrative compounds of formula I are described, wherein $R^{5'}$ and X' are taken together with the attached nitrogen atom to form an heterocycle selected from the group consisting of pyrrolidin-1-yl, piperidin-1-yl, piperazin-1-yl, and homopiperazin-1-yl; where said heterocycle is substituted with $C_1$-$C_6$ alkyl, $C_3$-$C_8$ cycloalkyl, optionally-substituted aryl, optionally-substituted aryl($C_1$-$C_4$ alkyl), the second heterocycle Y', Y'—($C_1$-$C_4$ alkyl), $R^{7'}R^{8'}N$—, $R^{7'}R^{8'}N$—($C_1$-$C_4$ alkyl), or $R^{7'}R^{8'}N$—C(O)-($C_1$-$C_4$ alkyl).

Illustrative compounds of formula I are described, wherein $R^{5'}$ and X' are taken together with the attached nitrogen atom to form an heterocycle selected from the group consisting of piperidin-1-yl and piperazin-1-yl, where the heterocycle is substituted with $C_1$-$C_6$ alkyl, $C_3$-$C_8$ cycloalkyl, optionally-substituted aryl($C_1$-$C_4$ alkyl), $R^{7'}R^{8'}N$—, or $R^{7'}R^{8'}N$—($C_1$-$C_4$ alkyl).

Illustrative compounds of formula I and II are described, wherein $R^{7'}$ and $R^{8'}$ are taken together with the attached nitrogen atom to form an heterocycle selected from the group consisting of pyrrolidinyl, piperidinyl, morpholinyl, piperazinyl, and homopiperazinyl, where said piperazinyl or homopiperazinyl is optionally substituted at the 4-position with ($C_1$-$C_4$ alkyl), ($C_3$-$C_8$ cycloalkyl), or aryl($C_1$-$C_4$ alkyl).

Illustrative compounds of formula I are described, wherein $R^{5'}$ and X' are taken together with the attached nitrogen atom to form piperazin-1-yl, where said piperazin-1-yl is substituted with $C_1$-$C_6$ alkyl, $C_3$-$C_8$ cycloalkyl, or aryl ($C_1$-$C_4$ alkyl).

Illustrative compounds of formula I are described, wherein the integer n is 1.

Illustrative compounds of formula I are described, wherein the integer n is 2.

Illustrative compounds of formula II are described, wherein the integer n' is 1.

Illustrative compounds of formula II are described, wherein the integer n' is 2.

The present invention also describes a pharmaceutical comprising a compound selected from those described above, and a pharmaceutically acceptable carrier, diluent, or excipient.

The general chemical terms used in the formulae above have their usual meanings. For example, the term "alkyl" includes such groups as methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

The term "cycloalkyl" includes such groups as cyclopropyl, cyclobutyl, cyclopentyl, cyclohexyl, cycloheptyl, cyclooctyl, and the like.

The term "alkenyl" includes such groups as ethenyl, propenyl, 2-butenyl, and the like.

The term "alkynyl" includes such groups as ethynyl, propynyl, 1-butynyl, and the like.

The term "aryl" refers to an aromatic ring or heteroaromatic ring and includes such groups as furyl, pyrrolyl, thienyl, pyridinyl, thiazolyl, oxazolyl, isoxazolyl, isothiazolyl, imidazolyl, pyrazolyl, phenyl, pyridazinyl, pyrimidinyl, pyrazinyl, thiadiazolyl, oxadiazolyl, naphthyl, indanyl, fluorenyl, quinolinyl, isoquinolinyl, benzodioxanyl, benzofuranyl, benzothienyl, and the like.

The term "optionally-substituted" refers to the replacement of one or more, preferably from one to three, hydrogen atoms with one or more substituents. Such substituents include such groups as $C_1$-$C_4$ alkyl, $C_1$-$C_4$ alkoxy, $C_1$-$C_4$ alkylthio, hydroxy, nitro, halo, carboxy, cyano, $C_1$-$C_4$ haloalkyl, $C_1$-$C_4$ haloalkoxy, amino, carboxamido, amino, mono($C_1$-$C_4$ alkyl)amino, di($C_1$-$C_4$ alkyl)amino, $C_1$-$C_4$ alkylsulfonylamino, and the like.

The term "heterocycle" refers to a saturated cyclic structure possessing one or more heteroatoms, such as nitrogen, oxygen, sulfur, and the like, and includes such groups as tetrahydrofuryl, morpholinyl, pyrrolidinyl, piperidinyl, piperazinyl, homopiperazinyl, quinuclidinyl, and the like.

The term "alkoxy" includes such groups as methoxy, ethoxy, propoxy, isopropoxy, butoxy, tert-butoxy and the like.

The terms "acyl" and "alkanoyl" include such groups as formyl, acetyl, propanoyl, butanoyl, pentanoyl and the like.

The term "halo" means fluoro, chloro, bromo, and iodo.

The term "alkanoyloxy" includes such groups as formyloxy, acetoxy, n-propionoxy, n-butyroxy, pivaloyloxy, and like lower alkanoyloxy groups.

The terms "optionally-substituted $C_1$-$C_4$ alkyl" and "optionally-substituted $C_2$-$C_4$ alkenyl" are taken to mean an alkyl or alkenyl chain which is optionally substituted with up to two methyl groups or with a $C_1$-$C_4$ alkoxycarbonyl group.

The term "($C_1$-$C_4$ alkyl)" as used in for example "aryl ($C_1$-$C_4$ alkyl)", "($C_1$-$C_4$ alkoxy)-($C_1$-$C_4$ alkyl)", and the like, refers to a saturated linear or branched divalent alkyl chain of from one to four carbons bearing for example aryl, $C_1$-$C_4$ alkoxy, and the like, as a substituent and includes such groups as for example benzyl, phenethyl, phenpropyl, α-methylbenzyl, methoxymethyl, ethoxyethyl, and the like.

The term "optionally-substituted phenyl" is taken to mean a phenyl radical optionally substituted with one or two substituents independently selected from the group consisting of $C_1$-$C_4$ alkyl, $C_1$-$C_4$ alkoxy, hydroxy, halo, nitro, trifluoromethyl, sulfonamido, cyano, carbamoyl, amino, mono($C_1$-$C_4$ alkyl)amino, di($C_1$-$C_4$ alkyl)amino, $C_1$-$C_4$ alkylsulfonylamino, and indol-2-yl.

The term "protected amino" refers to amine protecting groups used to protect the nitrogen of the β-lactam ring during preparation or subsequent reactions. Examples of such groups are benzyl, 4-methoxybenzyl, 4-methoxyphenyl, or trialkylsilyl, for example trimethylsilyl.

The term "protected carboxy" refers to the carboxy group protected or blocked by a conventional protecting group commonly used for the temporary blocking of the acidic carboxy. Examples of such groups include lower alkyl, for example tert-butyl, halo-substituted lower alkyl; for example 2-iodoethyl and 2,2,2-trichloroethyl, benzyl and substituted benzyl, for example 4-methoxybenzyl and 4-nitrobenzyl, diphenylmethyl, alkenyl, for example allyl, trialkylsilyl, for example trimethylsilyl and tert-butyldiethylsilyl and like carboxy-protecting groups.

The term "antagonist", as it is used in the description of this invention, is taken to mean a full or partial antagonist. A compound which is a partial antagonist at the vasopressin $V_{1a}$ receptor must exhibit sufficient antagonist activity to inhibit the effects of vasopressin or a vasopressin agonist at an acceptable dose. While a partial antagonist of any intrinsic activity may be useful, partial antagonists of at least about 50% antagonist effect are preferred and partial antagonists of at least about 80% antagonist effect are more preferred. Full antagonists of the vasopressin $V_{1a}$ receptor are most preferred.

DETAILED DESCRIPTION OF THE INVENTION

Certain classes of compounds of the present invention having formula I or formula II are preferred. Illustrative classes of such compounds are described in the following paragraphs.

A class of compounds having formula I, wherein:
(aa) A is $R^6O-$;
(ab) $R^6$ is $C_1$-$C_6$ alkyl;
(ac) $R^6$ is optionally-substituted aryl($C_1$-$C_4$ alkyl);
(ad) A is a monosubstituted amino of the formula XNH—;
(ae) A is a disubstituted amino having the formula $R^5XN-$;
(af) A' is a monosubstituted amino having the formula X'NH—;
(ag) A' is a disubstituted amino having the formula $R^{5'}X'N-$;
(ah) A' is $R^{6'}O-$;
(ai) $R^{6'}$ is $C_1$-$C_6$ alkyl;
(aj) $R^{6'}$ is optionally-substituted aryl($C_1$-$C_4$ alkyl);
(ak) X is optionally-substituted aryl($C_1$-$C_4$ alkyl);
(al) X is $R^7R^8N-(C_1$-$C_4$ alkyl);
(am) $R^7$ and $R^8$ are taken together with the attached nitrogen atom to form an heterocycle;
(an) $R^5$ and X are taken together with the attached nitrogen atom to form an heterocycle;
(ao) the heterocycle is optionally substituted with an optionally-substituted aryl($C_1$-$C_4$ alkyl), the first heterocycle Y, or $C_3$-$C_8$ cycloalkyl;
(ap) $R^2$ is hydrogen;
(aq) $R^2$ is $C_1$-$C_6$ alkyl;
(ar) $R^2$ is $C_1$-$C_2$ alkyl;
(as) $R^3$ is 4-substituted oxazolidin-2-on-3-yl;
(at) $R^3$ is 4,5-disubstituted oxazolidin-2-on-3-yl;
(au) $R^3$ is 2-substituted oxazolidin-4-on-3-yl;
(av) $R^3$ is 2-substituted imidazolidin-4-on-3-yl;
(aw) $R^3$ is 1,2-disubstituted imidazolidin-4-on-3-yl;
(ax) $R^3$ is 5-substituted imidazolidin-2-on-1-yl;
(ay) $R^3$ is 4,5-disubstituted imidazolidin-4-on-1-yl;
(az) $R^4$ is optionally-substituted 2-aryleth-1-yl;
(ba) $R^4$ is optionally-substituted 2-arylethen-1-yl;
(bb) $R^{5'}$ is benzyl;
(bc) X' is the heterocycle Y;
(bd) X is optionally-substituted aryl($C_1$-$C_4$ alkyl);
(be) aryl is optionally-substituted phenyl;
(bf) X' is $R^{7'}R^{8'}N-(C_1$-$C_4$ alkyl);
(bg) X' is $R^{7'}R^{8'}N-$;
(bh) $R^{7'}$ is $C_1$-$C_6$ alkyl;
(bi) $R^{8'}$ is $C_1$-$C_6$ alkyl;
(bj) $R^7$ and $R^8$ are taken together with the attached nitrogen atom to form an heterocycle;
(bk) $R^7$ and $R^8$ are the same and are $C_1$-$C_6$ alkyl;
(bl) $R^{5'}$ and X' taken together with the nitrogen to which they are attached form pyrrolidinyl, piperidinyl, piperazinyl; where said pyrrolidinyl, piperidinyl, or piperazinyl is optionally substituted with the second heterocycle Y' or with $R^7R^8N-(C_1$-$C_4$ alkyl);
(bm) $R^{5'}$ and X' taken together with the nitrogen to which they are attached form piperidinyl optionally substituted at the 4-position with hydroxy, $C_1$-$C_6$ alkyl, $C_3$-$C_8$ cycloalkyl, $C_1$-$C_4$ alkoxy, ($C_1$-$C_4$ alkoxy)carbonyl, (hydroxy($C_1$-$C_4$ alkyloxy))-($C_1$-$C_4$ alkyl), $R^7R^8N-$, $R^7R^8N-(C_1$-$C_4$ alkyl), phenyl, phenyl($C_1$-$C_4$ alkyl), optionally-substituted phenyl ($C_1$-$C_4$ alkyl), furyl($C_1$-$C_4$ alkyl), pyridinyl($C_1$-$C_4$ alkyl), thienyl($C_1$-$C_4$ alkyl), or piperidin-1-yl($C_1$-$C_4$ alkyl);
(bn) $R^5$ and X' taken together with the nitrogen to which they are attached form piperazinyl optionally substituted at the 4-position with $C_1$-$C_6$ alkyl, $C_3$-$C_8$ cycloalkyl, optionally-substituted phenyl, optionally-substituted phenyl($C_1$-$C_4$ alkyl), N—($C_1$-$C_5$ alkyl) acetamid-2-yl, N—($C_3$-$C_8$ cycloalkyl) acetamid-2-yl, $R^7R^8N-$, or ($C_1$-$C_4$ alkoxy)carbonyl; and (bo) $R^{5'}$ and X' taken together with the nitrogen to which they are attached form homopiperazinyl optionally substituted in the 4-position with $C_1$-$C_4$ alkyl, phenyl, or phenyl ($C_1$-$C_4$ alkyl).

It is appreciated that the classes of compounds described above may be combined to form additional illustrative classes. An example of such a combination of calsses may be a class of compounds wherein A is a monosubstituted amino having the formula XNH—, where X is optionally-substituted aryl($C_1$-$C_4$ alkyl), and A' is a disubstituted amino having the formula $R^{5'}X'N-$, where $R^{5'}$ and X' are taken together with the attached nitrogen atom to form an heterocycle, such as piperidine, peperazine, and the like. Further combinations of the classes of compounds described above are contemplated in the present invention.

Further illustrative classes of compounds are described by compounds having formula III:

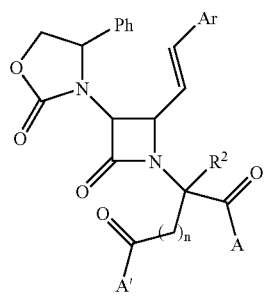

III wherein:
Ar is optionally-substituted phenyl, optionally-substituted pyridinyl, optionally-substituted furyl, or optionally-substituted thienyl;
$R^2$ is hydrogen;
A is XNH—;
A' is X'NH—;
A' is $R^{5'}X'N-$;
n is 0, 1, or 2;
X is optionally-substituted aryl($C_1$-$C_4$ alkyl), and aryl is substituted phenyl;
A' is $R^{6'}O-$;
$R^{6'}$ is $C_1$-$C_6$ alkyl;
X' is $R^{7'}R^{8'}N-$;
X' is optionally-substituted aryl($C_1$-$C_4$ alkyl);
X' is the second heterocycle Y';
$R^{5'}$ and X' are taken together with the attached nitrogen atom to form piperidinyl, piperazinyl, or homopiperazinyl; where said piperidinyl, piperazinyl, or homopiperazinyl is optionally substituted with $C_1$-$C_6$ alkyl, $C_3$-$C_8$ cycloalkyl, the second heterocycle Y', optionally-substituted aryl($C_1$-$C_4$ alkyl), $R^7R^8N-$, $R^7R^8N-(C_1$-$C_4$ alkyl), or $R^7R^8N-C(O)-(C_1$-$C_4$ alkyl);
$R^{8'}$ is $C_1$-$C_6$ alkyl, $C_3$-$C_8$ cycloalkyl, optionally-substituted aryl, optionally-substituted aryl($C_1$-$C_4$ alkyl); and
$R^{7'}$ and $R^{8'}$ are taken together with the attached nitrogen atom to form an heterocycle selected from the group consisting of pyrrolidinyl, piperidinyl, morpholinyl, and piperazinyl; where said piperazinyl is optionally substituted at the 4-position with $C_1$-$C_4$ alkyl.

Further illustrative classes of compounds are described by compounds having formula IV:

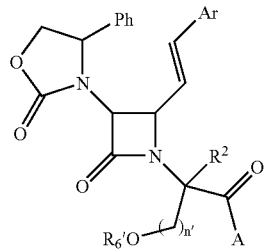

wherein:
Ar is optionally-substituted phenyl, optionally-substituted pyridinyl, optionally-substituted furyl, or optionally-substituted thienyl;

$R^2$ is hydrogen;

A is XNH—;

n' is 1, 2, or 3;

X is optionally-substituted aryl($C_1$-$C_4$ alkyl), and aryl is substituted phenyl;

$R^{6'}$ is $R^{8'}$ is $C_1$-$C_6$ alkyl, $C_3$-$C_8$ cycloalkyl, optionally-substituted aryl, optionally-substituted aryl($C_1$-$C_4$ alkyl); and $R^{7'}$ and $R^{8'}$ are taken together with the attached nitrogen atom to form an heterocycle selected from the group consisting of pyrrolidinyl, piperidinyl, morpholinyl, and piperazinyl; where said piperazinyl is optionally substituted at the 4-position with $C_1$-$C_4$ alkyl.

The following Tables 1-5 are illustrative of compounds contemplated to be within the scope of the present invention.

TABLE 1

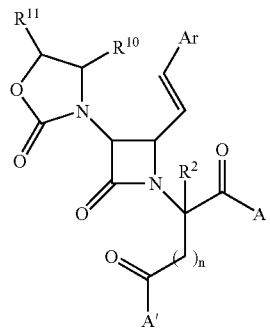

2-[3-(Oxazolidin-2-on-3-yl)azetidinon-1-yl]alkanedioic acid derivatives.

| n | $R^2$ | $R^{10}$ | $R^{11}$ | A | A' | Ar |
|---|---|---|---|---|---|---|
| 0 | H | benzofur-2-yl | 3-iodophenyl | 2-(piperidin-1-yl)ethylamino | 4-(pyrrolidin-1-yl)piperazin-1-yl | fur-3-yl |
| 0 | methyl | benzofur-7-yl | 4-fluorophenyl | 4-(piperidin-1-yl)piperidin-1-yl | 4-(3-trifluorophenyl)piperazin-1-yl | pyrrol-2-yl |
| 0 | ethyl | benzothien-5-yl | 4-cyanophenyl | 4-(phenylethyl)piperazin-1-yl | 4-(benzyloxycarbonyl)piperazin-1-yl | pyrrol-3-yl |
| 1 | methyl | benzothien-3-yl | phenyl | fur-2-ylmethylamino | 4-[2-(2-hydroxyethoxy)ethyl]piperazin-1-yl | pyridin-2-yl |
| 1 | H | thien-2-yl | methoxycarbonyl | 4-(3-trifluoromethylphenyl)piperazin-1-yl | 4-(3,4-methylenedioxybenzyl)piperazin-1-yl | pyridin-4-yl |
| 1 | H | naphth-2-yl | 4-ethylaminophenyl | 4-(benzyloxycarbonyl)piperazin-1-yl | 4-phenylpiperazin-1-yl | thiazol-2-yl |
| 2 | methyl | 3-phenyprop-1-yl | 2-isobutoxycarbonyl | 4-[2-(2-hydroxyethoxy)ethyl]piperazin-yl | 4-(3-phenylprop-2-enyl)piperazin-1-yl | thiazol-4-yl |
| 2 | ethyl | 2-pheneth-1-yl | 2-methanesulfonylaminophenyl | 4-benzylpiperazin-1-yl | 4-ethylpiperazin-1-yl | thiazol-5-yl |
| 2 | methyl | 3-isopropylbenzyl | cyclohexyl | 4-(3,4-methylenedioxybenzyl)piperazin-1-yl | 2-(dimethylamino)ethylamino | oxazol-2-yl |

TABLE 2

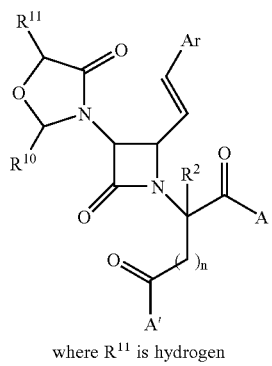

where R[11] is hydrogen

2-[3-(Oxazolidin-4-on-3-yl)azetidinon-1-yl]alkanedioic acid derivatives.

| n | R[2] | R[10] | A | A'' | Ar |
|---|---|---|---|---|---|
| 0 | ethyl | 4-fluorobenzyl | 4-phenylpiperazin-1-yl | 4-(pyrrolidin-1-ylcarbonylmethyl)piperazin-1-yl | oxazol-4-yl |
| 0 | H | benzyl | 4-(3-phenylprop-2-enyl)piperazin-1-yl | 4-(1-methylpiperidin-4-yl)piperazin-1-yl | oxazol-5-yl |
| 0 | methyl | 4-methoxyphenyl | 4-ethylpiperazin-1-yl | 4-butylpiperazin-1-yl | isoxazol-3-yl |
| 1 | H | 3-chlorophenyl | 2-(dimethylamino)ethylamino | 4-isopropylpiperazin-1-yl | isoxazol-4-yl |
| 1 | methyl | 2-ethylphenyl | 4-(pyrrolidin-1-ylcarbonylmethyl)piperazin-1-yl | 2-(piperidin-1-yl)ethylamino | isoxazol-5-yl |
| 1 | ethyl | phenyl | 4-(1-methylpiperidin-4-yl)piperazin-1-yl | 4-(2-phenylethyl)piperazin-1-yl | imidazol-2-yl |
| 1 | methyl | cyclopropyl | 4-butylpiperazin-1-yl | 4-(piperidin-1-yl)piperidin-1-yl | imidazol-4-yl |
| 2 | H | cyclobutyl | 4-isopropylpiperazin-1-yl | 2-(pyridin-2-yl)ethylamino | imidazol-5-yl |
| 2 | H | cyclopentyl | 4-pyridylmethylamino | morpholin-4-ylamino | pyrazol-3-yl |
| 2 | H | cyclohexyl | 3-(dimethylamino)propylamino | 4-(pyrrolidin-1-yl)piperazin-1-yl | pyrazol-4-1 |

TABLE 3

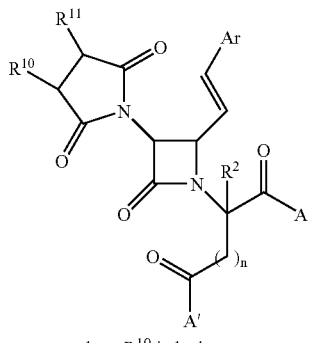

where R[10] is hydrogen

2-[3-(Succinimid-1-yl)azetidinon-1-yl]alkanedioic acid derivatives.

| n | R[2] | R[11] | A | A' | Ar |
|---|---|---|---|---|---|
| 0 | H | naphth-2-yl | 1-benzylpiperidin-4-ylamino | 4-(3-trifluorophenyl)piperazin-1-yl | pyrazol-5-yl |
| 0 | ethyl | propyl | N-benzyl-2-(dimethylamino)ethylamino | 4-(benzyloxycarbonyl)piperazin-1-yl | pyrimidin-2-yl |
| 0 | methyl | 3-chloronaphth-1-yl | 3-pyridylmethylamino | 4-[2-(2-hydroxyethoxy)ethyl]piperazin-1-yl | pyrimidin-4-yl |
| 1 | ethyl | ethyl | 4-(cyclohexyl)piperazin-1-yl | 4-benzylpiperazin-1-yl | Pyrimidin-5-yl |
| 1 | H | 6-methoxynaphth-2-yl | 4-(2-cyclohexylethyl)piperazin-1-yl | 4-(3,4-methylenedioxybenzyl)piperazin-1-yl | Thiadiazol-3-yl |
| 1 | methyl | methyl | 4-[2-(morpholin-4-yl)ethyl]piperazin-1-yl | 4-phenylpiperazin-1-yl | Oxadiazol-3-yl |
| 1 | H | 5-aminonaphth-2-yl | 4-(4-tert-butylbenzyl)piperazin-1-yl | 4-(3-phenylprop-2-enyl)piperazin-1-yl | Quinolin-2-yl |
| 2 | methyl | ethoxycarbonyl | 4-[2-(piperidin-1-yl)ethyl]piperazin-1-yl | 4-ethylpiperazin-1-yl | Quinolin-3-yl |
| 2 | ethyl | isopropyl | 4-[3-(piperidin-1-yl)propyl]piperazin-1-yl | 2-(dimethylamino)ethylamino | Quinolin-4-yl |
| 2 | methyl | tert-butoxycarbonyl | 4-[2-(N,N-dipropylamino)ethyl]piperazin-1-yl | 4-(pyrrolidin-1-ylcarbonylmethyl)piperazin-1-yl | Isoquinolin-1-yl |

TABLE 4

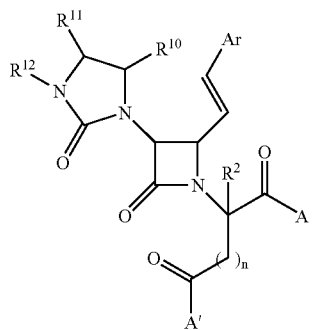

2-[3-(Imidazol-2-on-1-yl)azetidinon-1-yl]alkanedioic acid derivatives.

| n | $R^2$ | $R^{10}$ | $R^{11}$ | $R^{12}$ | A | A' | Ar |
|---|---|---|---|---|---|---|---|
| 0 | H | 3-nitrophenyl | propyl | tert-butoxycarbonyl | 4-[3-(N,N-diethylamino)propyl]piperazin-1-yl | 4-(1-methylpiperidin-4-yl)piperazin-1-yl | naphth-1-yl |
| 0 | ethyl | 3-(thiobenzyl)prop-1-yl | naphth-1-yl | benzyloxycarbonyl | 4-[2-(dimethylamino)ethyl]piperazin-1-yl | 4-butylpiperazin-1-yl | naphth-2-yl |
| 0 | methyl | Phenoxycarbonyl | ethyl | H | 4-[3-(pyrrolidin-1-yl)propyl]piperazin-1-yl | 4-isopropylpiperazin-1-yl | 2-fluorophenyl |
| 1 | methyl | 2-methoxycarbonyl-ethyl | naphth-2-yl | 4-isopropylbenzyloxycarbonyl | 4-(cyclohexylmethyl)piperazin-1-yl | 4-pyridylmethylamino | 3-chlorophenyl |
| 1 | ethyl | 4-methanesulfonyl-phenyl | methyl | 3-methoxybenzyloxycarbonyl | 4-cyclopentylpiperazin-1-yl | 3-(dimethylamino)propylamino | 4-bromophenyl |
| 1 | H | Isopropyl | 2-chloronaphth-1-yl | 2-butoxybenzyloxycarbonyl | 4-[2-(pyrrolidin-1-yl)ethyl]piperazin-1-yl | 1-benzylpiperidin-4-ylamino | 2-methylphenyl |
| 1 | ethyl | 3-aminophenyl | 6-methoxy-naphth-2-yl | 3-chlorobenzyloxycarbonyl | 4-[2-(thien-2-yl)ethyl]piperazin-1-yl | N-benzyl-2-(dimethylamino)ethylamino | 3-isopropylphenyl |
| 2 | H | 2-cyanophenyl | isobutyl | 3-fluoro-5-methoxybenzyloxycarbonyl | 4-(3-phenylpropyl)piperazin-1-yl | 3-pyridylmethylamino | 2-propoxyphenyl |
| 2 | methyl | 3-methyl-thiobutyl | 5-aminonaphth-2-yl | 3-cyanobenzyloxycarbonyl | 4-[2-(N,N-diethylamino)ethyl]piperazin-1-yl | 4-cyclohexylpiperazin-1-yl | 3-methoxyphenyl |
| 2 | H | 4-hydroxy-phenyl | butyl | methyl | 4-benzylhomopiperazin-1-yl | 4-(2-cyclohexylethyl)piperazin-1-yl | 2-ethylthiophenyl |

TABLE 5

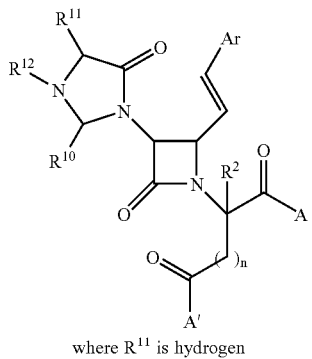

where $R^{11}$ is hydrogen

2-[3-(Imidazol-5-on-1-yl)azetidinon-1-yl]alkanedioic acid derivatives.

| n | $R^2$ | $R^{10}$ | $R^{12}$ | A | A' | Ar |
|---|---|---|---|---|---|---|
| 0 | methyl | 2-fluoro-4-methoxyphenyl | 3-aminobenzyloxycarbonyl | 4-(bisphenylmethyl)piperazin- | 4-[2-(morpholin-4-yl)ethyl]piperazin-1-yl | 4-methylthio-phenyl |
| 0 | ethyl | 3-ethoxyphenyl | 2-hydroxybenzyloxycarbonyl | 3-(4-methylpiperazin-1-yl)propylamino | 4-(4-tert-butylbenzyl)piperazin-1-yl | 2-nitro-phenyl |
| 0 | methyl | 2-methylphenyl | 3-ethylaminobenzyloxycarbonyl | (+)-3(S)-1-benzylpyrrolidin-3-ylamino | 4-[2-(piperidin-1-yl)ethyl]piperazin-1-yl | 2-carboxy-phenyl |
| 1 | H | 2-methoxyphenyl | 4-dimethylaminobenzyloxycarbonyl | 2-pyridylmethylamino | 4-[3-(piperidin-1-yl)propyl]piperazin-1-yl | 3-carboxamido-phenyl |
| 1 | H | 3-ethoxyphenyl | methyl | 4-ethylpiperazin-1-yl | 4-[2-(diisopropylamino)ethyl]piperazin-1-yl | 2,3-difluorophenyl |
| 1 | H | 3-iso-propylphenyl | benzyl | 2-(dimethylamino)ethylamino | 4-[3-(diethylamino)propyl]piperazin-1-yl | 3,5-dichlorophenyl |
| 1 | H | 4-chlorophenyl | isopropoxycarbonyl | 4-(pyrrolidin-1-ylcarbonylmethyl)piperazin-1-yl | 4-(2-dimethylaminoethyl)piperazin-1-yl | 3-chloro-4-bromophenyl |
| 2 | ethyl | 2-chloro-4-bromophenyl | propoxycarbonyl | 4-(1-methylpiperidin-4-yl)piperazin-1-yl | 4-[3-(pyrrolidin-1-yl)propyl]piperazin-1-yl | 5,6-dichloro-3-iodophenyl |
| 2 | H | 2-ethyl-3-bromophenyl | ethoxycarbonyl | 4-butylpiperazin-1-yl | 4-(cyclohexylmethyl)piperazin-1-yl | 2,4-dimethylphenyl |
| 2 | ethyl | 2-chloro-4-bromophenyl | methoxycarbonyl | 4-isopropylOpiperazin-1-yl | 4-(2-dimethylaminoethyl)piperazin-1-yl | 3-methyl-4-isopropoxy-phenyl |

The compounds of the present invention are comprised of an azetidinone nucleus, said nucleus bearing asymmetric carbons at the 3- and 4-positions as illustrated by following structures:

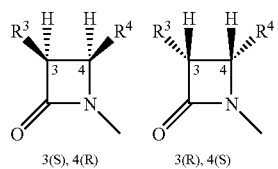

The compounds of the invention may, therefore, exist as single diastereomers, mixtures of diastereomers, or as a racemic mixture, all of which are useful and part of the invention. It is preferred that the azetidinone nucleus of the compounds of the invention exist in a single diastereomeric form. It is most preferred that the azetidinone nucleus exist as the (3S,4R)-diastereomer.

It is appreciated that, except when A=A' and n=0, the carbon bearing $R^2$ is also asymmetric. Furthermore, when $R^3$ is 4-substituted oxazolidin-2-on-3-yl, the 4-position of that ring is asymmetric. In addition, when $R^3$ is 2,5-disubstituted oxazolidin-4-on-3-yl or 1,2,5-trisubstituted imidazolidin-4-on-3-yl, the 2- and 5-carbons of those rings are asymmetric. Finally, when $R^3$ is succinimido and one of $R^{14}$ and $R^{15}$ is hydrogen, the carbon bearing the non-hydrogen substituent is also asymmetric. While compounds possessing all combinations of stereochemical purity are contemplated by the present invention, it is appreciated that in many cases at least one of these chiral centers described above may be present in a single absolute configuration.

The compounds of this invention are useful in methods for antagonism of the vasopressin $V_{1a}$ receptor. Such antagonism is useful in treating a variety of disorders that have been linked to this receptor in mammals. It is preferred that the mammal to be treated by the administration of compounds of this invention is human.

Since certain of the compounds of this invention are amines, they are basic in nature and accordingly react with any of a number of inorganic and organic acids to form pharmaceutically acceptable acid addition salts. Because some of the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as N-toluenesulfonic acid, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid, trifluoroacetic acid, maleic acid or fumaric acid.

The 2-(azetidinon-1-yl)alkanedioic acid esters and amides of formulae I and II are prepared by syntheses well known in the art. As illustrated for compounds of formula I, the 2-(azetidinon-1-yl)alkanedioic acid esters are obtainable by the 2+2 cycloaddition of an appropriately substituted acetic acid derivative (i), and an imine ester (ii) as described in Synthetic Scheme I, where Z is a leaving group, and the integer n, and the moieties A, A', $R^2$, $R^3$, and $R^4$ are as previously described. The term "leaving group" as used hereinafter refers to a subsitutent, such as halo, acyloxy, benzoyloxy and the like, present on an activated carbon atom that may be replaced by a nucleophile. The chemistry described in Synthetic Scheme I is applicable to imines (ii) bearing ester, thioester, or amide moieties.

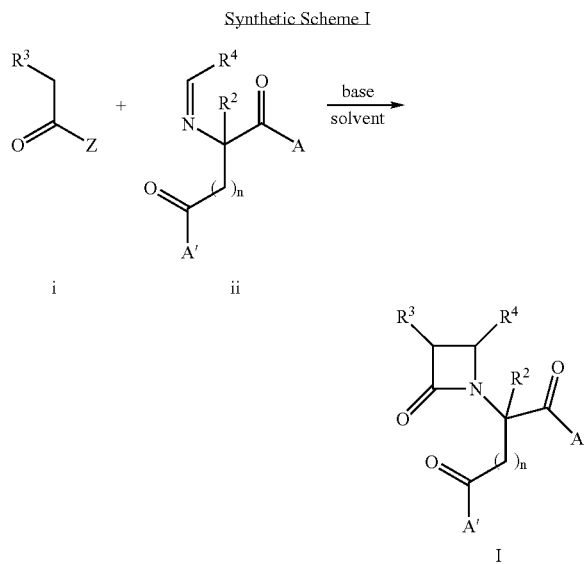

Synthetic Scheme I

The preparation of the appropriate imines (ii) and most of the required acetyl halides or anhydrides (i), as well as the cycloaddition procedure, are generally described in U.S. Pat. Nos. 4,665,171 and 4,751,299, hereby incorporated by reference. The analogous synthesis of compounds of formula II may be accomplished by this process using the appropriate alkoxy-substituted amino acid imines.

Those compounds of formulae I and II of the invention requiring $R^3$ to be 4-substituted oxazolidin-2-on-3-yl or 1,4,5-trisubstituted imidazolidin-2-on-3-yl are prepared from the corresponding (4-substituted oxazolidin-2-on-3-yl)- or (1,4,5-trisubstituted imidazolidin-2-on-3-yl)-acetyl halide or anhydride. The acid halide or anhydride is available from an appropriately substituted glycine. The glycine is first converted to the carbamate and then reduced to provide the corresponding alcohol. The alcohol is then cyclized to the 4-substituted oxazolidin-2-one, which is subsequently N-alkylated with a haloacetic acid ester. The ester is hydrolyzed, and the resulting acid is converted to the acetyl halide or anhydride (i).

Those compounds of the invention requiring $R^3$ to be 2,5-disubstituted oxazolidin-4-on-3-yl or 1,2,5-trisubstituted imidazolidin-4-on-3-yl are prepared from the corresponding (2,5-disubstituted oxazolidin-4-on-3-yl)- or (1,2,5-trisubstituted imidazolidin-4-on-3-yl)acetyl chlorides or anhydrides respectively. The chemistry to prepare these reagents is described in U.S. Pat. No. 4,772,694, hereby incorporated by reference. Briefly, the required oxazolidinone or imidazolidinone is obtained from an α-hydroxyacid or an α-aminoacid, respectively. The imidazolones are prepared by converting the α-aminoacid, $(R^{11})$—$CH(NH_2)$$CO_2H$, to an amino-protected amide and then condensing the amide with an aldehyde, $(R^{10})$—CHO, in the presence of an acid to form the 3-protected imidazolidin-4-one, where $R^{10}$ and $R^{11}$ are as defined above. The 1-position may be functionalized with an appropriate reagent to introduce $R^{12}$ and the 3-position deprotected, where $R^{12}$ is as defined above. The imidazolidin-4-one ring is then alkylated with a haloacetic acid ester, the ester deesterified, and the resulting acetic acid converted to the desired acid halide or anhydride (i). The required oxazolidinones are prepared in an analogous manner from the corresponding α-hydroxyacid, $(R^{11})$—$CH(OH)CO_2H$.

Those compounds of the invention requiring $R^3$ to be succinimido are prepared from the corresponding 2-(succinimido)acetyl halide or anhydride. The chemistry to prepare these reagents is described in U.S. Pat. No. 4,734,498, hereby incorporated by reference. Briefly, these reagents are obtained from tartaric acid or, when one of $R^{10}$ and $R^{11}$ is hydrogen, from malic acid. Tartaric acid is acylated or O-alkylated, the corresponding diacyl or di-O-alkyl tartaric acid is treated with an acid anhydride to form the succinic anhydride, and reaction of this succinic anhydride with an ester of glycine to form first the noncyclic half amide ester which is then cyclized to the 3,4-disubstituted succinimidoacetic acid ester. The ester group is deesterified and the resulting acid converted to the corresponding acid halide or anhydride (i). The mono-substituted succinimidoacetyl halide or anhydride is obtained with malic acid via succinic anhydride formation followed by succinimide formation as described above.

Those compounds of the invention requiring $R^3$ to be an N-substituted amine or an N'-substituted urea may be prepared from the corresponding phthalimido protected 3-amino analogs. The phthalimide protecting group may be removed using conventional procedures, such as by treatment with hydrazine, and the like. Once liberated, the amine may be alkylated with any one of a variety of alkyl and cycloalkyl halides and sulfates, such as methyl iodide, isopropylbromide, diethyl sulfate, cyclopropylmethylbromide, cyclopentyliodide, and the like. Such amines may also be acylated with acid halides, acid anhydrides, isocyanates, isothiocyanates, such as acetyl chloride, propionic anhydride, methylisocyanate, 3-trifluoromethylphenylisothiocyanate, and the like.

The bases to be used in Synthetic Scheme I include, among others, aliphatic tertiary amines, such as trimethylamine and triethylamine, cyclic tertiary amines, such as N-methylpiperidine and N-methylmorpholine, aromatic amines, such as pyridine and lutidine, and other organic bases such as 1,8-diazabicyclo[5,4,0]undec-7-ene (DBU).

The solvents useful for reactions described in Synthetic Scheme I include, among others, dioxane, tetrahydrofuran, diethyl ether, ethyl acetate, dichloromethane, chloroform, carbon tetrachloride, benzene, toluene, acetonitrile, dimethyl sulfoxide and N,N-dimethylformamide.

Alternatively, the compounds of formulae I and II may be prepared via N—C(4) cyclization, as illustrated for compounds of formula I in Synthetic Scheme II, via cyclizatoin of β-hydroxy amides iii, where $R^2$, $R^3$, $R^4$, A, and A' are as defined previously, according to the procedure of Townsend and Nguyen in *J. Am. Chem. Soc.* 1981, 103, 4582, and Miller and Mattingly in *Tetra.* 1983, 39, 2563, the disclosures of which are incorporated herein by reference. The analogous synthesis of compounds of formula II may be accomplished by cyclizatoin of β-hydroxy amides of alkoxy-substituted amino acids.

Synthetic Scheme II

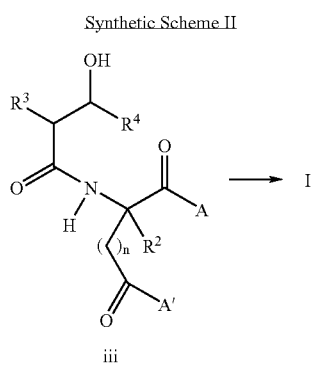

iii

The azetidinone ring may also be prepared with a deficit of substituents $R^3$, $R^4$, or the $R^2$-substituted N-alkanedioic acid or alkoxyalkanoic acid moiety, but possessing substituents capable of being elaborated through subsequent chemical transformation to such groups described for compounds of formulae I and II. In general, azetidinones may be prepared via N—C(4) cyclization, such as the cyclization of acylhydroxamates iv to azetidinone intermediates v, as depicted in Scheme III, where $R^2$, $R^3$, $R^4$, A, and A' are as defined above, according to the procedure of Mattingly et al. in *J. Am. Chem. Soc.* 1979, 101, 3983 and *Accts. Chem. Res.* 1986, 19, 49, the disclosures of which are incorporated herein by reference. It is appreciated that other hydroxamates, such as alkylhydroxamates, aryl hydroxamates, and, the like, are suitable for carrying out the cyclization.

Synthetic Scheme III

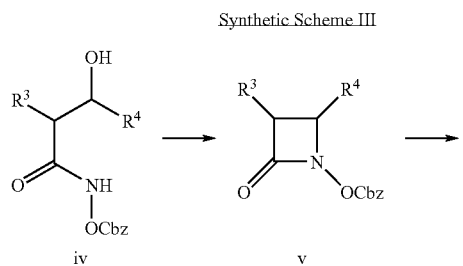

iv    v

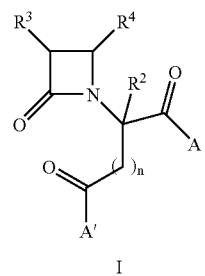

I

Subsequent chemical transformation of the acyloxyazetidinone v to introduce for example an $R^2$-substituted alkanedioic acid moiety using conventional procedures will illustratively provide compounds of formula I. The analogous synthesis of compounds of formula II may be accomplished by this process using an appropriate $R^2$-substituted alkoxyalkanoic acid.

An alternative cyclization to form intermediate azetidinones, which may be further elaborated to compounds of formulae I and II, may occur by oxidative cyclization of acylhydroxamates vi to intermediate azetidinones vii, as illustrated in Synthetic Scheme IV, where $R^3$ is as defined above, according to the procedure of Rajendra and Miller in *J. Org. Chem.* 1987, 52, 4471 and *Tetrahedron Lett.* 1985, 26, 5385, the disclosures of which are incorporated herein by reference. The group R in Scheme IV represents an alkyl or aryl moiety selected to provide $R^4$, as defined above, upon subsequent transformation. For example, R may be the group $PhCH_2$—, as in vii-a, such that oxidative elimination of HBr will provide the desired $R^4$, a styryl group, as in vii-b. It is appreciated that elaboration of R to $R^4$ is not necessarily performed immediately subsequent to the cyclization and may be performed conveniently after other steps in the synthesis of compounds of formulae I and II. It is further appreciated that alternatives to the acylhydroxamates shown, such as alkylhydroxamates, aryl hydroxamates, and the like, are suitable for carrying out the cyclization.

Synthetic Scheme IV

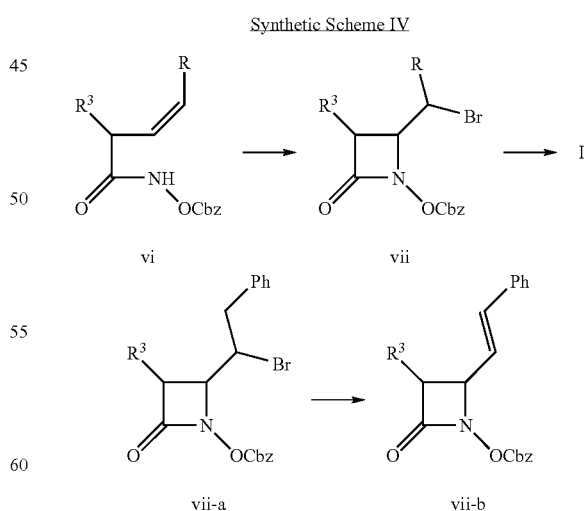

Other useful intermediates, such as the azetidinone-4-carboxaldehyde viii illustrated in Synthetic Scheme V for preparing for example compounds of formula I, may be further elaborated to 4-($R^4$)-substituted azetidinones via an olefination reaction. The group R in Scheme V is selected such that upon successful olefination of the carboxaldehyde the resulting group R—CHCH— corresponds to the desired alkyl or aryl moiety $R^4$, as defined above. Such olefination reactions may be accomplished by any of the variety of known procedures, such as by Wittig olefination, Peterson olefination, and the like. Synthetic Scheme V illustrates the corresponding Wittig olefination with phosphorane ix. The analogous synthesis of compounds of formula II may be accomplished by this process using an appropriate alkoxy-substituted azetidinone-4-carboxaldehyde derivative.

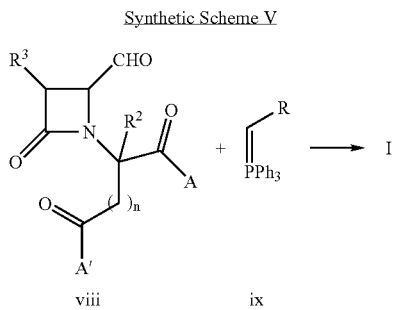

Still other useful intermediates, such as the azetidinonyl acetic acid derivatives x, may be converted into compounds of formulae I and II, as illustrated for the synthesis of compounds of formula I in Synthetic Scheme VI. Introduction of an $R^2$ moiety, and a carboxylic acid derivative A'—C(O)—$(CH_2)_n$— for compounds of formula I, or an alkoxyalkanoic acid derivative $R^{6'}O$—$(CH_2)_n$— for compounds of formula II, may be accomplished by alkylation of the anion of x, where the integers n and n', and the groups $R^2$, $R^3$, $R^4$, $R^{6'}$, A, and A' are as defined above.

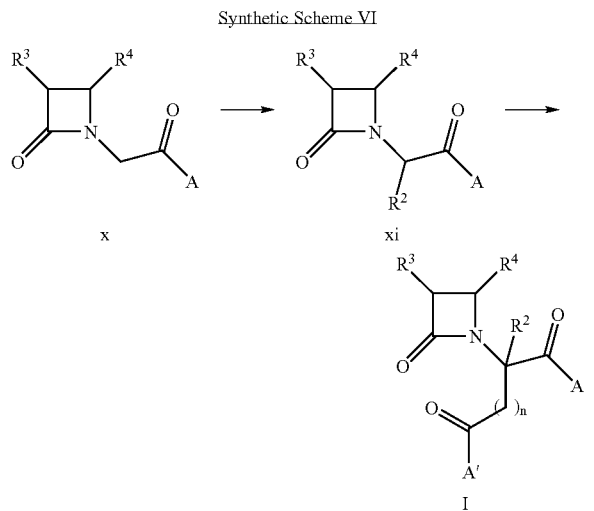

Acetic acid derivative x is deprotonated and subsequently alkylated with an alkyl halide corresponding to $R^2$-Z, where Z is a leaving group, to provide intermediate xi. Illustratively, the anion of xi may be alkylated with a compound Z'—$(CH_2)_n$COA', where Z' is a leaving group, to provide compounds of formula I. It is appreciated that the order of introduction of either the substituent $R^2$ or the acid derivative —$(CH_2)_n$COA', or the alkoxyalkanoic acid derivative —$(CH_2)_n$$OR^{6'}$, is conveniently chosen by the skilled artisan and such order of introduction may be different for each compound of formula I or formula II.

A solution of the 2-(3,4-disubstituted azetidin-2-on-1-yl) acetic acid derivative x or xi in an appropriate solvent, such as tetrahydrofuran, dioxane, or diethyl ether, is treated with a non-nucleophilic base to generate the anion of x or xi, respectively. Suitable bases for this transformation include lithium diisopropylamide, lithium 2,2,6,6-tetramethylpiperidinamide, or lithium bis(trimethylsilyl)amide. The anion is then quenched with an appropriate electrophile to provide the desired compounds. Illustrative electrophiles represented by the formulae $R^2$-Z, $R^{5'}$X'N—C(O)—$(CH_2)_n$-Z, or $R^{6'}$O—C(O)—$(CH_2)_n$-Z provide the corresponding compounds xi or I, respectively. The analogous synthesis of compounds of formula II may be accomplished by this process by using an electrophile represented by the formula $R^{6'}$O—$(CH_2)_n$-Z.

As discussed above, the compounds prepared as described in Synthetic Schemes I, II, III, IV, V, and VI may be pure diastereomers, mixtures of diastereomers, or racemates. The actual stereochemical composition of the compound will be dictated by the specific reaction conditions, combination of substituents, and stereochemistry of the reactants employed. It is appreciated that diasteromeric mixtures may be separated by chromatography or fractional crystallization to provide single diastereomers if desired. Particularly, the reactions described in Synthetic Schemes III, IV, and VI create a new chiral center at the carbon bearing $R^2$, except when n=0 and A=A'.

Compounds of formula I which are 2-(3,4-disubstituted azetidin-2-on-1-yl)alkanedioic acid half-esters, such as compounds I-a where A' is $R^{6'}$O—, while useful vasopressin $V_{1a}$ agents in their own right, may also be converted to the corresponding half-carboxylic acids xii, where the integer n and the groups $R^2$, $R^3$, $R^4$, $R^{5'}$, $R^{6'}$, A, and X' are as previously defined, as illustrated in Synthetic Scheme VII. These intermediates are useful for the preparation of other compounds of the invention, such as I-b where A' is $R^{5'}$X'N—. It is appreciated that the transformation illustrated in Synthetic Scheme VII is equally applicable for the preparation of compounds I where A' is X'NH— or where a different $R^{6'}$O— is desired.

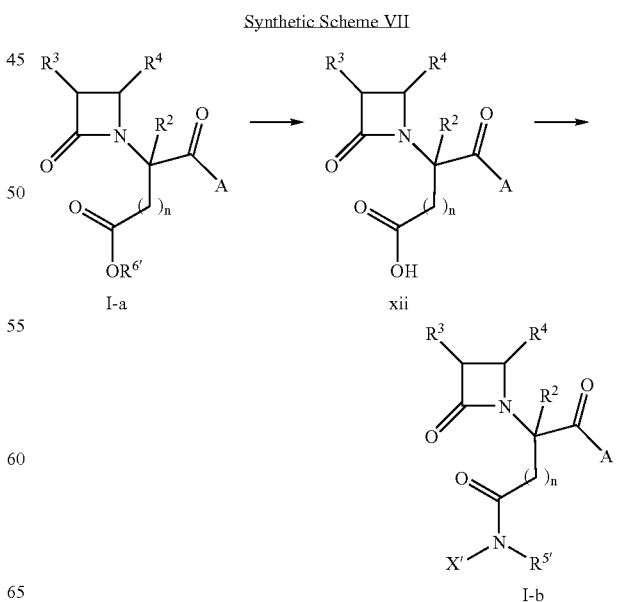

The requisite carboxylic acid xii may be prepared from the corresponding ester via saponification under standard conditions by treatment with hydroxide followed by protonation of the resultant carboxylate anion. Where $R^{6'}$ is tert-butyl, the ester I-a may be dealkylated by treatment with trifluoroacetic acid. Where $R^{6'}$ is benzyl, the ester I-a may be dealkylated either by subjection to mild hydrogenolysis conditions, or by reaction with elemental sodium or lithium in liquid ammonia. Finally, where $R^{6'}$ is 2-(trimethylsilyl) ethyl, the ester I-a may be deprotected and converted into the corresponding acid xii by treatment with a source of fluoride ion, such as tetrabutylammonium fluoride. The choice of conditions is dependent upon the nature of the $R^{6'}$ moiety and the compatability of other functionality in the molecule with the reaction conditions.

The carboxylic acid xii is converted to the corresponding amide I-b under standard conditions well recognized in the art. The acid may be first converted to the corresponding acid halide, preferably the chloride or fluoride, followed by treatment with an appropriate primary or secondary amine to provide the corresponding amide. Alternatively, the acid may be converted under standard conditions to a mixed anhydride. This is typically accomplished by first treating the carboxylic acid with an amine, such as triethylamine, to provide the corresponding carboxylate anion. This carboxylate is then reacted with a suitable haloformate, for example benzyl chloroformate, ethyl chloroformate or isobutylchloroformate, to provide the corresponding mixed anhydride. This anhydride may then be treated with an appropriate primary or secondary amine to provide the desired amide. Finally, the carboxylic acid may be treated with a typical peptide coupling reagent such as N,N'-carbonyldiimidazole (CDI), N,N'-dicyclohexylcarbodiimide (DCC) and 1-(3-dimethylaminopropyl)-3-ethylcarbodiimide hydrochloride (EDC), followed by the appropriate amine of formula $R^5XNH$. A polymer-supported form of EDC has been described in *Tetrahedron Letters*, 34(48), 7685 (1993), the disclosure of which is incorporated herein by reference, and is very useful for the preparation of the compounds of the present invention. It is appreciated that substituting an appropriate amine with an appropriate alcohol in the synthethic scheme presented above will provide the esters of the invention, e.g. analogs of I-a with a different ester $R^6O$—.

The carboxylic acid may alternatively be converted into the corresponding tert-butyl ester via treatment of the acid with an acid catalyst, such as concentrated sulfuric acid, and the like, and with isobutylene in a suitable solvent, such as dioxane, and the like. The reaction is preferably carried out under pressure in an appropriate vessel, such as a pressure bottle, and the like. Reaction times of about 18 hours are not uncommon. The desired ester may be be isolated from the organic layer after partitioning the reaction mixture between a suitable organic solvent, such as ethyl acetate, and the like, and a basic aqueous layer, such as cold 1N sodium hydroxide, and the like.

It is appreciated that the transformation illustrated in Synthetic Scheme VII may also be used to convert in an analogous fashion, the half-ester I where A is $R^6O$— to the corresponding acid and subsequently into derivatives I where A is XNH—, $R^5XN$—, or a different $R^6O$—. Finally, it is appreciated that the transformation in Synthetic Scheme VII may also be used to convert in an analogous fashion the esters of formula II, where A is $R^6O$—, to the corresponding acids, and subsequently into derivatives of formula II, where A is XNH—, $R^5XN$—, or a different $R^6O$—.

Compounds of formulae I and II where $R^4$ includes an ethenyl or ethynyl spacer; such as for example compounds I-c and I-d, respectively, may be converted into the corresponding arylethyl derivatives, compounds I-e, via reduction, as illustrated for compounds of formula I in Synthetic Scheme VIII. Conversion is accomplished by catalytic hydrogenation, and other like reductions, where the integer n and the groups $R^2$, $R^3$, A, and A' are as previously defined. The corresponding compounds of formula II may also be converted from ethyne and ethene precursors in an analogous fashion. The moiety R depicted in Scheme VIII is chosen such that the substituent R—CC—, R—CHCH—, or R—$CH_2CH_2$— corresponds to the desired $R^4$ of formulae I or II as defined above.

Synthetic Scheme VIII

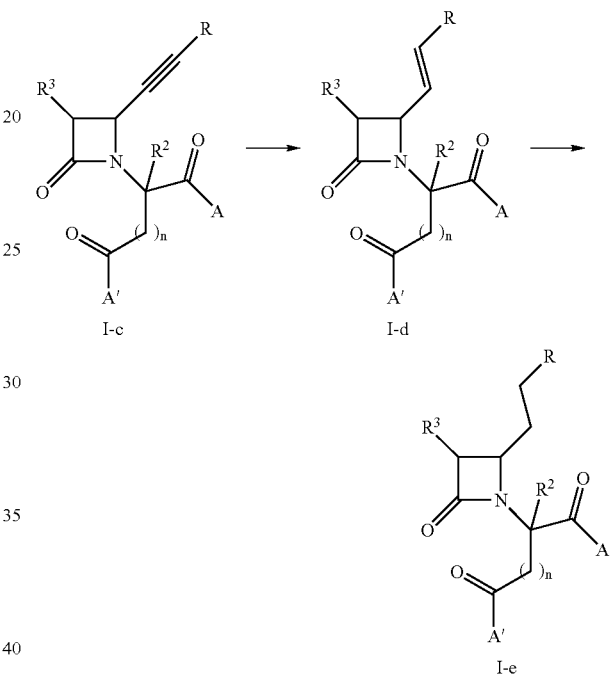

The hydrogenation of the triple or double bond proceeds readily over a precious metal catalyst, such as palladium on carbon. The hydrogenation solvent may consist of a lower alkanol, such as methanol or ethanol, tetrahydrofuran, or a mixed solvent system of tetrahydrofuran and ethyl acetate. The hydrogenation may be performed at an initial hydrogen pressure of about 20-80 p.s.i., preferably about 50-60 p.s.i., at a temperature of about 0-60° C., preferably within the range of from ambient temperature to about 40° C., for about 1 hour to about 3 days.

Alternatively, the ethynyl spacer of compound I-c may be selectively reduced to the ethenyl spacer of compound I-d using poisoned catalyts, such as Pd on $BaSO_4$, Lindlar's catalyst, and the like. It is appreciated that either the Z or E double bond geometry of compound I-d may be advantageously obtained by the appropriate choice of reaction conditions. The analogous synthesis of compounds of formula II may be accomplished by this process.

Compounds of formula I and II where $R^3$ is phthalimido are conveniently treated with hydrazine or a hydrazine derivative, for example methylhydrazine, to prepare the corresponding 2-(3-amino-4-substituted azetidin-2-on-1-yl) alkanedioic acid derivatives xiii, as illustrated in Synthetic Scheme IX for compounds of formula I, where the integer n, and the groups $R^2$, $R^4$, $R^{12}$, A, and A' are as previously defined. This compound may then be treated with an appropriate alkylating or acylating agent to prepare the corresponding amines or amides I-g, or alternatively intermediates xiii may be treated with an appropriate isocyanate to prepare the corresponding ureas I-h.

Synthetic Scheme IX

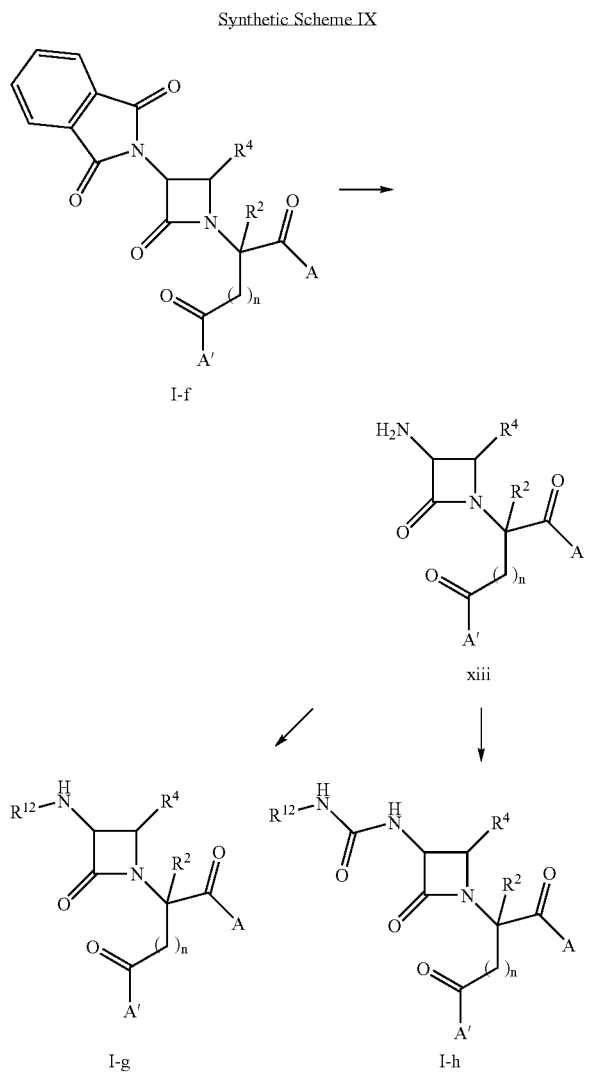

The ureas I-h are prepared by treating a solution of the appropriate amine xiii in a suitable solvent, such as chloroform or dichloromethane, with an appropriate isocyanate, $R^{12}$NCO. If necessary, an excess of the isocyanate is employed to ensure complete reaction of the starting amine. The reactions are performed at about ambient temperature to about 45° C., for from about three hours to about three days. Typically, the product may be isolated by washing the reaction with Water and concentrating the remaining organic components under reduced pressure. When an excess of isocyanate has been used, however, a polymer bound primary or secondary amine, such as an aminomethylated polystyrene, may be conveniently added to facilitate removal of the excess reagent. Isolation of products from reactions where a polymer bound reagent has been used is greatly simplified, requiring only filtration of the reaction mixture and then concentration of the filtrate under reduced pressure.

The substituted amines and amides I-g are prepared by treating a solution of the appropriate amine xiii in a suitable solvent, such as chloroform or dichloromethane, with an appropriate acylating or alkylating agent, $R^{12}$—C(O)Z or $R^{12}$-Z, respectively. If necessary, an excess of the acylating or alkylating agent is employed to ensure complete reaction of the starting amine. The reactions are performed at about ambient temperature to about 45° C., for from about three hours to about three days. Typically, the product may be isolated by washing the reaction with water and concentrating the remaining organic components under reduced pressure. When an excess of the acylating or alkylating agent has been used, however, a polymer bound primary or secondary amine, such as an aminomethylated polystyrene, may be conveniently added to facilitate removal of the excess reagent. Isolation of products from reactions where a polymer bound reagent has been used is greatly simplified, requiring only filtration of the reaction mixture and then concentration of the filtrate under reduced pressure. The analogous synthesis of compounds of formula II may be accomplished by this process.

The following preparations and examples further illustrate the synthesis of the compounds of this invention and are not intended to limit the scope of the invention in any way. Unless otherwise indicated, all reactions were performed at ambient temperature, and all evaporations were performed in vacuo. All of the compounds described below were characterized by standard analytical techniques, including nuclear magnetic resonance spectroscopy ($^1$H NMR) and mass spectral analysis (MS).

EXAMPLE 1

(4(S)-phenyloxazolidin-2-on-3-yl)acetyl chloride

A solution of 1.0 equivalent of (4(S)-phenyloxazolidin-2-on-3-yl)acetic acid (Evans, U.S. Pat. No. 4,665,171) and 1.3 equivalent of oxalyl chloride in 200 mL dichloromethane was treated with a catalytic amount of anhydrous dimethylformamide (85 mL/milliequivalent of acetic acid derivative) resulting in vigorous gas evolution. After 45 minutes all gas evolution had ceased and the reaction mixture was concentrated under reduced pressure to provide the title compound as an off-white solid after drying for 2 h under vacuum.

EXAMPLE 2

General Procedure for Amide Formation From an Activated Ester Derivative

N-Benzyloxycarbonyl-L-aspartic acid β-t-butyl ester α-(3-trifluoromethyl)benzylamide.

A solution of N-benzyloxycarbonyl-L-aspartic acid β-t-butyl ester α-N-hydroxysuccinimide ester (1.95 g, 4.64 mmol, Advanced ChemTech) in 20 mL of dry tetrahydrofuran was treated with 0.68 mL (4.74 mmol) of 3-(trifluoromethyl)benzyl amine. Upon completion (TLC, 60:40 hexanes/ethyl acetate), the mixture was evaporated, and the resulting oil was partitioned between dichloromethane and a saturated aqueous solution of sodium bicarbonate. The organic laer was evaporated to give 2.23 g (quantitative yield) of the title compound as a white solid; $^1$H NMR (CDCl$_3$) δ 1.39 (s, 9H), 2.61 (dd, J=6.5 Hz, J=17.2 Hz, 1H), 2.98 (dd, J=3.7 Hz, J=17.0 Hz, 1H), 4.41 (dd, J=5.9 Hz, J=15.3 Hz, 1H), 4.50-4.57 (m, 2H), 5.15 (s, 2H), 5.96-5.99 (m, 1H), 6.95 (s, 1H), 7.29-7.34 (m, 5H), 7.39-7.43 (m, 2H), 7.48-7.52 (m, 2H).

Examples 3-5 were prepared according to the procedure of Example 2, except that N-benzyloxycarbonyl-L-aspartic acid β-t-butyl ester α-N-hydroxysuccinimide ester was replaced by the appropriate amino acid derivative, and 3-(trifluoromethyl)benzyl amine was replaced with the appropriate amine.

EXAMPLE 3

N-Benzyloxycarbonyl-L-aspartic acid β-t-butyl ester α-[4-(2-phenylethyl)]piperazinamide N-benzyloxycarbonyl-L-aspartic acid β-t-butyl ester (α-N-hydroxysuccinimide ester (5.0 g, 12 mmol, Advanced ChemTech) and 4-(phenylethyl)piperazine 2.27 mL (11.9 mmol) gave 5.89 g (quantitative yield) of the title compound as an off-white oil; $^1$H NMR (CDCl$_3$) δ 1.40 (s, 9H), 2.45-2.80 (m, 10H), 3.50-3.80 (m, 4H), 4.87-4.91 (m, 1H), 5.08 (s, 2H), 5.62-5.66 (m, 1H), 7.17-7.33 (m, 10H).

EXAMPLE 4

N-Benzyloxycarbonyl-L-glutamic acid γ-t-butyl ester α-(3-trifluoromethyl)benzylamide N-benzyloxycarbonyl-L-glutamic acid β-t-butyl ester α-N-hydroxysuccinimide ester (4.83 g, 11.1 mmol, Advanced ChemTech) and 3-(trifluoromethyl)benzylamine) 1.63 mL (11.4 mmol) gave 5.41 g (98%) of the title compound as an off-white solid; $^1$H NMR (CDCl$_3$) δ 1.40 (s, 9H), 1.88-1.99 (m, 1H), 2.03-2.13 (m, 1H), 2.23-2.33 (m, 1H), 2.38-2.47 (m,1H), 4.19-4.25 (s, 1H), 4.46-4.48 (m, 2H), 5.05-5.08 (m, 2H), 5.67-5.72 (m, 1H), 7.27-7.34 (m, 5H), 7.39-7.43 (m, 2H), 7.48-7.52 (m, 2H).

EXAMPLE 5

N-Benzyloxycarbonyl-L-glutamic acid γ-t-butyl ester α-[4-(2-phenylethyl)]piperazinamide N-benzyloxycarbonyl-L-glutamic acid γ-t-butyl ester α-N-hydroxysuccinimide ester (5.0 g, 12 mmol, Advanced ChemTech) and 4-phenylethyl)piperazine 2.19 mL (1.51 mmol) gave 5.87 g (quantitative yield) of the title compound as an off-white oil; $^1$H NMR (CDCl$_3$) δ 1.43 (s, 9H); 1.64-1.73 (m,1H); 1.93-2.01 (m, 1H); 2.23-2.40 (m, 2H); 2.42-2.68 (m, 6H); 2.75-2.85 (m, 2H); 3.61-3.74 (m, 4H); 4.66-4.73 (m, 1H); 5.03-5.12 (m, 2H); 5.69-5.72 (m, 1H); 7.16-7.34 (m, 10H).

EXAMPLE 5A

N-[(9H-Fluoren-9-yl)methoxycarbonyl]-O-(benzyl)-D-serine t-Butyl ester

N-[(9H-Fluoren-9-yl)methoxycarbonyl]-O-(benzyl)-D-serine (0.710 g, 1.70 mmole) in dichloromethane (8 mL) was treated with 1-butyl acetate (3 mL) and concentrated sulfuric acid (40 μL) in a sealed flask at 0° C. Upon completion (TLC), the reaction was quenched with of dichloromethane (10 mL) and saturated aqueous potassium bicarbonate (15 mL). The organic layer was washed with distilled water, and evaporated. The resulting residue was purified by flash column chromatography (98:2 dichloromethane/methanol) to yield the title compound as a colorless oil (0.292 g, 77%); $^1$H NMR (CDCl$_3$) δ 1.44 (s, 9H); 3.68 (dd, J=2.9 Hz, J=9.3 Hz, 1H); 3.87 (dd, J=2.9 Hz, J=9.3 Hz, 1H); 4.22 (t, J=7.1 Hz, 1H); 4.30-4.60 (m, 5H); 5.64-5.67 (m, 1H); 7.25-7.39 (m, 9H); 7.58-7.61 (m, 2H); 7.73-7.76 (m, 2H).

EXAMPLE 5B

O-(Benzyl)-D-serine t-Butyl ester

Example 5A (0.620 g, 1.31 mmol) in dichloromethane (5 mL) was treated with tris(2-aminoethyl)amine (2.75 mL) for 5 h. The resulting mixture was washed twice with a phosphate buffer (pH=5.5), once with saturated aqueous potassium bicarbonate, and evaporated to give 0.329 g (quantitative yield) of the title compound as an off-white solid; $^1$H NMR (CD$_3$OD) δ 1.44 (s, 9H); 3.48 (dd, J=J'=4.2 Hz, 1H); 3.61 (dd, J=4.0 Hz, J=9.2 Hz, 1H); 3.72 (dd, J=4.6 Hz, J=9.2 Hz, 1H); 4.47 (d, J=12.0 Hz, 1H); 4.55 (d, J=12.0 Hz, 1H); 7.26-7.33 (m, 5H).

EXAMPLE 6

General Procedure for Amide Formation From a Carboxylic Acid

N-Benzyloxycarbonyl-D-aspartic acid β-t-butyl ester α-(3-trifluoromethyl)benzylamide A solution of 1 g (2.93 mmol) of N-benzyloxycarbonyl-D-aspartic acid β-t-butyl ester monohydrate (Novabiochem) in 3-4 mL of dichloromethane was treated by sequential addition of 0.46 mL (3.21 mmol) of 3-(trifluoromethyl)benzylamine, 0.44 g (3.23 mmol) of 1-hydroxy-7-benzotriazole, and 0.62 g (3.23 mmol) of 1-[3-(dimethylamino)propyl]-3-ethylcarbodiimide hydrochloride. After at least 12 hours at ambient temperature or until complete as determined by thin-layer chromatography (95:5 dichloromethane/methanol eluent), the reaction mixture was washed sequentially with a saturated aqueous sodium bicarbonate solution and with distilled water. The organic layer was evaporated to give 1.41 g (quantitative yield) of the title compound as an off-white solid; $^1$H NMR (CDCl$_3$) δ 1.39 (s, 9H); 2.61 (dd, J=6.5 Hz, J=17.2 Hz, 1H); 2.98 (dd, J=4.2 Hz, J=17.2 Hz, 1H); 4.41 (dd, J=5.9 Hz, J=15.3 Hz, 1H); 4.50-4.57 (m, 2H); 5.10 (s, 2H); 5.96-6.01 (m, 1H); 6.91-7.00 (m, 1H); 7.30-7.36 (m, 5H); 7.39-7.43 (m, 2H); 7.48-7.52 (m, 2H).

Examples 7 and 7A-7E were prepared according to the procedure of Example 6, except that N-benzyloxycarbonyl-D-aspartic acid β-t-butyl ester monohydrate was replaced by the appropriate amino acid derivative, and 3-(trifluoromethyl)benzyl amine was replaced with the appropriate amine.

EXAMPLE 7

N-Benzyloxycarbonyl-D-glutamic acid γ-t-butyl ester α-(3-trifluoromethyl)benzylamide.

N-benzyloxycarbonyl-D-glutamic acid γ-t-butyl ester (1.14 g, 3.37 mmol) and 0.53 mL (3.70 mmol, Novabiochem) of 3-(trifluoromethyl)benzylamine gave 1.67 g (quantitative yield) of Example 7 as an off-white solid.

EXAMPLE 7A

N-Benzyloxycarbonyl-L-glutamic acid α-t-butyl ester γ-(4-cyclohexyl)piperazinamide.

N-benzyloxycarbonyl-L-glutamic acid α-t-butyl ester (1.36 g, 4.03 mmol) and 0.746 g (4.43 mmol) of 1-cyclohexylpiperazine gave 1.93 g (98%) of Example 7A as an off-white solid; $^1$H NMR (CDCl$_3$) δ 1.02-1.12 (m, 5H); 1.43 (s, 9H), 1.60-1.64 (m, 1H); 1.80-1.93 (m, 5H); 2.18-2.52 (m, 8H); 3.38-3.60 (m, 4H); 4.20-4.24 (m, 1H); 5.03-5.13 (m, 2H); 5.53-5.57 (m, 1H); 7.28-7.34 (m, 5H).

EXAMPLE 7B

N-Benzyloxycarbonyl-D-aspartic acid β-t-butyl ester α-(2-fluoro-3-trifluoromethyl)benzylamide.

N-benzyloxycarbonyl-D-aspartic acid β-t-butyl ester monohydrate (Novabiochem) (0.25 g, 0.73 mmol) and 0.12 mL of (2-fluoro-3-trifluoromethyl)benzylamine gave 0.365 g (quantitative yield) of Example 7B as an off-white solid; $^1$H NMR (CDCl$_3$) δ 1.38 (s, 9H); 2.59 (dd, J=6.5 Hz, J=17.0 Hz, 1H); 2.95 (dd, J=4.3 Hz, J=17.0 Hz, 1H); 4.46-4.56 (m, 3H); 5.11 (s, 2H); 5.94-5.96 (m, 1H); 7.15 (t, J=8.0 Hz, 1H); 7.30-7.36 (m, 5H); 7.47-7.52 (m, 2H).

EXAMPLE 7C

N-Benzyloxycarbonyl-D-aspartic acid β-t-butyl ester α-[(S)-α-methylbenzyl]amide.

N-benzyloxycarbonyl-D-aspartic acid β-t-butyl ester monohydrate (Novabiochem) (0.25 g, 0.73 mmol) and 0.094 mL of (S)-α-methylbenzylamine gave 0.281 g (90%) of Example 7C as an off-white solid; $^1$H NMR (CDCl$_3$) δ 1.41 (s, 9H); 1.44 (d, J=7.0 Hz, 3H); 2.61 (dd, J=7.0 Hz, J=17.0 Hz, 1H); 2.93 (dd, J=4.0 Hz, J=17.5 Hz, 1H); 4.50-4.54 (m, 1H); 5.04-5.14 (m, 3H); 5.94-5.96 (m, 1H); 6.76-6.80 (m, 1H); 7.21-7.37 (m, 10H).

EXAMPLE 7D

N-Benzyloxycarbonyl-D-aspartic acid β-t-butyl ester α-[(R)-α-methylbenzyl]amide.

N-benzyloxycarbonyl-D-aspartic acid β-t-butyl ester monohydrate (Novabiochem) (0.25 g, 0.73 mmol) and 0.094 mL of (R)-α-methylbenzylamine gave 0.281 g (90%) of Example 7D as an off-white solid; $^1$H NMR (CDCl$_3$) 67 1.38 (s, 9H); 1.43 (d, J=6.9 Hz, 3H); 2.54 (dd, J=7.3 Hz, J=17.2 Hz, 1H); 2.87 (dd, J=4.1 Hz, J=17.3 Hz, 1H); 4.46-4.50 (m, 1H); 4.99-5.15 (m, 3H); 5.92-5.96 (m, 1H); 6.78-6.82 (m, 1H); 7.21-7.33 (m, 10H).

EXAMPLE 7E

N-Benzyloxycarbonyl-D-aspartic acid γ-t-butyl ester α-[N-methyl-N-(3-trifluoromethylbenzyl)]amide.

N-benzyloxycarbonyl-D-aspartic acid γ-t-butyl ester (0.303 g, 0.89 mmol, Novabiochem) and 0.168 g (0.89 mmol,) of N-methyl-N-(3-trifluoromethylbenzyl)amine gave 0.287 g (65%) of Example 7E as an off-white solid; $^1$H NMR (CDCl$_3$) δ 1.40 (s, 9H); 2.55 (dd, J=5.8 Hz, J=15.8 Hz, 1H); 2.81 (dd, J=7.8 Hz, J=15.8 Hz, 1H); 3.10 (s, 3H); 4.25 (d, J=15.0 Hz, 1H); 4.80 (d, J=15.5 Hz, 1H); 5.01-5.13 (m, 3H); 5.52-5.55 (m, 1H); 7.25-7.52 (m, 10H).

EXAMPLE 8

General Procedure for Hydrogenation of a Benzyloxycarbonyl Amine.

L-aspartic acid β-t-butyl ester α-(3-trifluoromethyl)benzylamide.

A suspension of 2.23 g (4.64 mmol) of N-benzyloxycarbonyl-L-aspartic acid β-t-butyl ester α-(3-trifluoromethyl) benzylamide and palladium (5% wt. on activated carbon, 0.642 g) in 30 mL of methanol was held under an atmosphere of hydrogen until complete conversion as determined by thin layer chromatography (95:5 dichloromethane/methanol eluent). The reaction was filtered to remove the palladium over carbon and the filtrate was evaporated to give 1.52 g (96%) of the title compound as an oil; $^1$H NMR (CDCl$_3$) δ 1.42 (s, 9H); 2.26 (brs, 2H); 2.63-2.71 (m, 1H); 2.82-2.87 (m, 1H); 3.75-3.77 (m, 1H); 4.47-4.50 (m, 2H); 7.41-7.52 (m, 4H); 7.90 (brs, 1H).

Examples 9-13 and 13A-13E were-prepared according to the procedure of Example 8, except that N-benzyloxycarbonyl-L-aspartic acid β-t-butyl ester α-(3-trifluoromethyl)benzylamide was replaced by the appropriate amino acid derivative.

EXAMPLE 9

L-aspartic acid β-t-butyl ester α-[4-(2-phenylethyl)]piperazinamide.

N-benzyloxycarbonyl-L-aspartic acid β-t-butyl ester α-[4-(2-phenylethyl)]piperazinamide (5.89 g, 11.9 mmol) gave 4.24 g (98%) of Example 9 as an off-white oil; $^1$H NMR (CDCl$_3$): δ 1.42 (s, 9H); 2.61-2.95 (m, 10H); 3.60-3.90 (m, 4H); 4.35-4.45 (m, 1H); 7.17-7.29 (m, 5H).

EXAMPLE 10

D-aspartic acid β-t-butyl ester α-(3-trifluoromethyl)benzylamide.

N-benzyloxycarbonyl-D-aspartic acid β-t-butyl ester α-(3-trifluoromethyl)benzylamide (1.41 g, 2.93 mmol) gave 0.973 g (96%) of Example 10 as an off-white oil; $^1$H NMR (CDCl$_3$): δ 1.42 (s, 9H); 2.21 (brs, 2H); 2.67 (dd, J=7.1 Hz, J=16.8 Hz, 1H); 2.84 (dd, J=3.6 Hz, J=16.7 Hz, 1H); 3.73-3.77 (m, 1H); 4.47-4.50 (m, 2H); 7.41-7.52 (m, 4H); 7.83-7.87 (m, 1H).

EXAMPLE 11

L-glutamic acid γ-t-butyl ester α-(3-trifluoromethyl)benzylamide.

N-benzyloxycarbonyl-L-glutamic acid γ-t-butyl ester α-(3-trifluoromethyl)benzylamide (5.41 g, 10.9 mmol) gave 3.94 g (quantitative yield) of Example 11 as an off-white oil; $^1$H NMR (CDCl$_3$): δ 1.41 (s, 9H); 1.73-1.89 (m, 3H); 2.05-2.16 (m, 1H); 2.32-2.38 (m, 2H); 3.47 (dd, J=5.0 Hz, J=7.5 Hz, 1H); 4.47-4.49 (m, 2H); 7.36-7.54 (m, 4H); 7.69-7.77 (m, 1H).

EXAMPLE 12

L-glutamic acid γ-t-butyl ester
α-[4-(2-phenylethyl)]piperazinamide.

N-benzyloxycarbonyl-L-glutamic acid γ-t-butyl ester α-[4-(2-phenylethyl)]piperazinamide (5.86 g, 11.50 mmol) gave 4.28 g (99%) of Example 12 as an off-white oil; $^1$H NMR (CDCl$_3$) δ 1.39 (s, 9H); 2.00-2.08 (m, 1H); 2.38-2.46 (m, 1H); 2.55-2.90 (m, 9H); 3.61-3.82 (m, 4H); 4.48-4.56 (m, 1H); 7.17-7.26 (m, 5H).

EXAMPLE 13

D-glutamic acid γ-t-butyl ester
α-(3-trifluoromethyl)benzylamide.

N-benzyloxycarbonyl-D-glutamic acid γ-t-butyl ester α-(3-trifluoromethyl)benzylamide (1.667 g, 3.37 mmol) gave 1.15 g (94%) of Example 13 as an off-white oil; $^1$H NMR (CDCl$_3$) δ 1.41 (s, 9H); 1.80-2.20 (m, 4H); 2.31-2.40 (m, 2H); 3.51-3.59 (m, 1H); 4.47-4.49 (m, 2H); 7.39-7.52 (m, 4H); 7.71-7.79 (m, 1H).

EXAMPLE 13A

L-glutamic acid α-t-butyl ester
γ-(4-cyclohexyl)piperazinamide.

N-Benzyloxycarbonyl-L-glutamic acid α-t-butyl ester γ-(4-cyclohexyl)piperazinamide (1.93 g, 3.96 mmol) gave 1.30 g (93%) of Example 13A as an off-white oil; $^1$H NMR (CDCl$_3$) δ 1.02-1.25 (m, 5H); 1.41 (s, 9H); 1.45-1.50 (m, 1H); 1.56-1.60 (m, 1H); 1.69-1.80 (m, 6H); 3.30 (dd, J=4.8 Hz, J=8.5 Hz, 1H); 3.44 (t, J=9.9 Hz, 2H); 3.56 (t, J=9.9 Hz, 2H).

EXAMPLE 13B

D-aspartic acid β-t-butyl ester
α-(2-fluoro-3-trifluoromethyl)benzylamide.

N-benzyloxycarbonyl-D-aspartic acid β-t-butyl ester α-(2-fluoro-3-trifluoromethyl)benzylamide (0.36 g, 0.72 mmol) gave 0.256 g (92%) of Example 13B as an off-white oil; $^1$H NMR (CDCl$_3$) δ 1.39 (s, 9H); 2.50 (brs, 2H); 2.74 (dd, J=7.0 Hz, J=16.5 Hz, 1H); 2.86 (dd, J=4.8 Hz, J=16.8 Hz, 1H); 3.89 (brs, 2H); 4.47-4.57 (m, 2H); 7.16 (t, J=7.8 Hz, 1H); 7.48 (t, J=7.3 Hz, 1H); 7.56 (t, J=7.3 Hz, 1H); 7.97-8.02 (m, 1H).

EXAMPLE 13C

D-aspartic acid β-t-butyl ester
α-[(S)-α-methyl]benzylamide.

N-benzyloxycarbonyl-D-aspartic acid β-t-butyl ester α-[(S)-α-methylbenzyl]amide (0.275 g, 0.65 mmol) gave 0.17 g (90%) of Example 13C as an off-white oil; $^1$H NMR (CDCl$_3$) δ 1.40 (s, 9H); 1.47 (d, J=6.9 Hz, 3H); 1.98 (brs, 2H); 2.49 (dd, J=7.9 Hz, J=17.7 Hz, 1H); 2.83 (dd, J=3.6 Hz, J=16.7 Hz, 1H); 3.69 (brs, 1H); 4.99-5.10 (m, 1H); 7.19-7.33 (m, 5H); 7.65-7.6.8 (m, 1H).

EXAMPLE 13D

D-aspartic acid β-t-butyl ester
α-[(R)-α-methylbenzyl]amide.

N-benzyloxycarbonyl-D-aspartic acid β-t-butyl ester α-[(R)-α-methylbenzyl]amide (0.273 g, 0.64 mmol) gave 0.187 g (quantitative yield) of Example 13D as an off-white oil; $^1$H NMR (CDCl$_3$) δ 1.38 (s, 9H); 1.46 (d, J=6.9 Hz, 3H); 1.79 (brs, 2H); 2.51 (dd, J=7.8 Hz, J=17.5 Hz, 1H); 2.87 (dd, J=3.6 Hz, J=16.9 Hz, 1H); 4.19 (brs, 1H); 4.99-5.11 (m, 1H); 7.18-7.34 (m, 5H); 7.86-7.90 (m, 1H).

EXAMPLE 13E

D-aspartic acid β-t-butyl ester
α-[N-methyl-N-(3-trifluoromethylbenzyl)]amide.

N-benzyloxycarbonyl-D-aspartic acid β-t-butyl ester α-[N-methyl-N-(3-trifluoromethylbenzyl)]amide (0.282 g, 0.57 mmol) gave 0.195 g (95%) of Example 13E as an off-white oil.

EXAMPLE 14

General Procedure for Formation of a
2-Azetidinone from an Imine and an Acetyl
chloride.

Step 1: General Procedure for Formation of an Imine from an Amino Acid Derivative.

A solution of 1 equivalent of an α-amino acid ester or amide in dichloromethane is treated sequentially with 1 equivalent of an appropriate aldehyde, and a dessicating agent, such as magnesium sulfate or silica gel, in the amount of about 2 grams of dessicating agent per gram of starting α-amino acid ester or amide. The reaction is stirred at ambient temperature until all of the reactants are consumed as measured by thin layer chromatography. The reactions are typically complete within an hour. The reaction mixture is then filtered, the filter cake is washed with dichloromethane, and the filtrate concentrated under reduced pressure to provide the desired imine that is used as is in the subsequent step.

Step 2: General Procedure for the 2+2 Cycloaddition of an Imine and an Acetyl Chloride.

A dichloromethane solution of the imine (10 mL dichloromethane/1 gram imine) is cooled to 0° C. To this cooled solution is added 1.5 equivalents of an appropriate amine, typically triethylamine, followed by the dropwise addition of a dichloromethane solution of 1.1 equivalents of an appropriate acetyl chloride, such as that described in Example 1 (10 mL dichloromethane/1 gm appropriate acetyl chloride). The reaction mixture is allowed to warm to ambient temperature over 1 h and is then quenched by the addition of a saturated aqueous solution of ammonium chloride. The resulting mixture is partitioned between water and dichloromethane. The layers are separated and the organic layer is washed successively with 1N hydrochloric acid, saturated aqueous sodium bicarbonate, and saturated aqueous sodium chloride. The organic layer is dried over magnesium sulfate and concentrated under reduced pressure. The residue may be used directly for further reactions, or purified by chromatography or by crystallization from an appropriate solvent system if desired.

EXAMPLE 15 tert-Butyl [3(S)-(4(S)-phenyloxazolidin-2-on-3-yl)-4(R)-(2-styryl)azetidin-2-on-1-yl]acetate.

Using the procedure of Example 14, the imine prepared from 4.53 g (34.5 mmol) glycine tert-butyl ester and cinnamaldehyde was combined with 2-(4(S)-phenyloxazolidin-2-on-3-yl) acetyl chloride (Example 1) to give 5.5 g (30%) of Example 15 as colorless crystals (recrystallized, n-chlorobutane); mp 194-195° C.

EXAMPLE 16

General Procedure for Acylation of an (azetidin-2-on-1-yl)acetate.

A solution of (azetidin-2-on-1-yl)acetate in tetrahydrofuran (0.22 M in azetidinone) is cooled to −78° C. and is with lithium bis(trimethylsilyl)amide (2.2 equivalents). The resulting anion is treated with an appropriate acyl halide (1.1 equivalents). Upon complete conversion of the azetidinone, the reaction is quenched with saturated aqueous ammonium chloride and partitioned between ethyl acetate and water. The organic phase is washed sequentially with 1N hydrochloric acid, saturated aqueous sodium bicarbonate, and saturated aqueous sodium chloride. The resulting organic layer is dried (magnesium sulfate) and evaporated. The residue is purified by silica gel chromatography with an appropriate eluent, such as 3:2 hexane/ethyl acetate.

EXAMPLE 17

2,2,2-Trichloroethyl 2(RS)-(tert-butoxycarbonyl)-2-[3(S)-(4(S)-phenyloxazolidin-2-on-3-yl)-4(R)-(2-styryl)azetidin-2-on-1-yl]acetate Using the procedure of Example 16, 9.0 g (20 mmol) of Example 15 was acylated with 4.2 g (20 mmol) of trichloroethylchloroformate to give 7.0 g (56%) of Example 17; mp 176-178° C.

EXAMPLE 18

2(RS)-(tert-Butoxycarbonyl)-2-[3(S)-(4(S)-phenyloxazolidin-2-on-3-yl)-4(R)-(2-styryl)azetidin-2-on-1-yl]acetic acid N-(3-trifluoromethylbenzyl)amide A solution of 0.20 g (0.32 mmol) of Example 17 and 52 µL (0.36 mmol) of (3-trifluoromethylbenzyl)amine in THF was heated at reflux. Upon complete conversion (TLC), the solvent was evaporated and the residue was recrystallized (chloroform/hexane) to give 0.17 g (82%) of Example 18 as a white solid; mp 182-184° C.

Examples 19-25 and 25A-25H were prepared according to the procedure of Example 14, where the appropriate amino acid derivative and aldehyde were used in Step 1, and the appropriate acetyl chloride was used in Step 2.

EXAMPLE 19

2(S)-(tert-Butoxycarbonylmethyl)-2-[3(S)-(4(S)-phenyloxazolidin-2-on-3-yl)-4(R)-(2-styryl)azetidin-2-on-1-yl]acetic acid N-(3-trifluoromethylbenzyl)amide.

The imine prepared from 1.52 g (4.39 mmol) of L-aspartic acid β-1-butyl ester α-(3-trifluoromethyl)benzylamide and cinnamaldehyde was combined with 2-(4(S)-phenyloxazolidin-2-on-3-yl) acetyl chloride (Example 1) to give 2.94 g of an orange-brown oil that gave, after flash column chromatography purification (70:30 hexanes/ethyl acetate), 2.06 g (70%) of Example 19 as a white solid; $^1$H NMR (CDCl$_3$) δ 1.39 (s, 9H); 2.46 (dd, J=11.1 Hz, J=16.3 Hz, 1H); 3.18 (dd, J=3.8 Hz, J=16.4 Hz, 1H); 4.12-4.17 (m, 1H); 4.26 (d, J=5.0 Hz, 1H); 4.45 (dd, J=6.0 Hz, J=14.9 Hz, 1H); 4.54 (dd, J=5.3 Hz, J=9.8 Hz, 1H); 4.58-4.66 (m, 3H); 4.69-4.75 (m, 1H); 4.81 (dd, J=3.8 Hz, J=11.1 Hz, 1H); 6.25 (dd, J=9.6 Hz, J=15.8 Hz, 1H); 6.70 (d, J=15.8 Hz, 1H); 7.14-7.17 (m, 2H); 7.28-7.46 (m, 11H); 7.62 (s, 1H); 8.27-8.32 (m, 1H).

EXAMPLE 20

2(S)-(tert-Butoxycarbonylethyl)-2-[3(S)-(4(S)-phenyloxazolidin-2-on-3-yl)-4(R)-(2-styryl)azetidin-2-on-1-yl]acetic acid N-(3-trifluoromethylbenzyl)amide.

The imine prepared from 3.94 g (10.93 mmol) of L-glutamic acid γ-t-butyl ester α-(3-trifluoromethyl)benzylamide and cinnamaldehyde was combined with 2-(4(S)-phenyloxazolidin-2-on-3-yl) acetyl chloride (Example 1) to give 5.53 g (75%) of Example 20 after flash column chromatography purification (70:30 hexanes/ethyl acetate); $^1$H NMR (CDCl$_3$) δ 1.36 (s, 9H); 1.85-1.96 (m, 1H); 2.18-2.49 (m, 3H); 4.14-4.19 (m, 1H); 4.30 (d, J=4.9 Hz, 2H); 4.44 (dd, J=6.1 Hz, J=14.9 Hz, 1H); 4.56-4.67 (m, 4H); 4.71-4.75 (m, 1H); 6.26 (dd, J=9.6 Hz, J=15.8 Hz, 1H); 6.71 (d, J=15.8 Hz, 1H); 7.16-7.18 (m, 2H); 7.27-7.49 (m, 11H); 7.60 (s, 1H); 8.08-8.12 (m, 1H).

EXAMPLE 21

2(S)-(tert-Butoxycarbonylmethyl)-2-[3(S)-(4(S)-phenyloxazolidin-2-on-3-yl)-4(R)-(2-styryl)azetidin-2-on-1-yl]acetic acid N-[4-(2-phenylethyl)]piperazinamide.

The imine prepared from 4.20 g (11.6 mmol) of L-aspartic acid β-t-butyl ester α-[4-(2-phenylethyl)]piperazinamide and cinnamaldehyde was combined with 2-(4(S)-phenyloxazolidin-2-on-3-yl) acetyl chloride (Example 1) to give 4.37 g (55%) of Example 21 after flash column chromatography purification (50:50 hexanes/ethyl acetate); $^1$H NMR (CDCl$_3$) δ 1.34 (s, 9H); 2.26-2.32 (m, 1H); 2.46-2.63 (m, 4H); 2.75-2.89 (m, 4H); 3.24-3.32 (m, 1H); 3.49-3.76 (m, 3H); 4.07-4.13 (m, 1H); 4.30 (d, J=4.6 Hz, 1H); 4.22-4.48 (m, 1H); 4.55-4.61 (m, 1H); 4.69-4.75 (m, 1H); 5.04-5.09 (m, 1H); 6.15 (dd, J=9.3 Hz, 3=15.9 Hz, 1H); 6.63 (d, J=15.8 Hz, 1H); 7.18-7.42 (m, 15H).

EXAMPLE 22

2(S)-(tert-Butoxycarbonylethyl)-2-[3(S)-(4(S)-phenyloxazolidin-2-on-3-yl)-4(R)-(2-styryl)azetidin-2-on-1-yl]acetic acid (R)-[4-(2-phenylethyl)]piperazinamide.

The imine prepared from 2.54 g (6.75 mmol) of L-glutamic acid γ-t-butyl ester α-[4-(2-phenylethyl)]piperazinamide and cinnamaldehyde was combined with 2-(4(S)-phenyloxazolidin-2-on-3-yl) acetyl chloride (Example 1) to give 3.55 g (76%) of Example 22 after flash column chromatography purification (50:50 hexanes/ethyl acetate); $^1$H NMR (CDCl$_3$) δ 1.32 (s, 9H); 1.96-2.07 (m, 1H); 2.15-2.44 (m, 6H); 2.54-2.62 (m, 2H); 2.69-2.81 (m, 3H); 3.28-3.34

(m, 1H); 3.59-3.68 (m, 1H); 4.08-4.13 (m, 1H); 4.33-4.44 (m, 2H); 4.48-4.60 (m, 2H); 4.67-4.77 (m, 1H); 6.14 (dd, J=8.9 Hz, J=16.0 Hz, 1H); 6.62 (d, J=16.0 Hz, 1H); 7.16-7.42 (m, 15H).

EXAMPLE 23

2(R)-(tert-Butoxycarbonylmethyl)-2-[3(S)-(4(S)-phenyloxazolidin-2-on-3-yl)-4(R)-(2-styryl)azetidin-2-on-1-yl]acetic acid N-(3-trifluoromethylbenzyl) amide.

The imine prepared from 0.973 g (2.81 mmol) of D-aspartic acid β-t-butyl ester α-(3-trifluoromethyl)benzylamide and cinnamaldehyde was combined with 2-(4(S)-phenyloxazolidin-2-on-3-yl) acetyl chloride (Example 1) to give 1.53 g (82%) of Example 23 after flash column chromatography purification (70:30 hexanes/ethyl acetate); $^1$H NMR (CDCl$_3$) δ 1.37 (s, 9H); 3.10 (dd, J=3.7 Hz, J=17.8 Hz, 1H); 3.20 (dd, J=10.7 Hz, J=17.8 Hz, 1H); 4.02 (dd, J=3.6 Hz, J=10.6 Hz, 1H); 4.11-4.17 (m, 1H); 4.24 (d, J=4.9 Hz, 1H); 4.46 (dd, J=5.8 Hz, J=15.1 Hz, 1H); 4.58-4.67 (m, 3H); 4.70-4.76 (m, 1H); 6.27 (dd, J=9.5 Hz, J=15.8 Hz, 1H); 6.79 (d, J=15.8 Hz, 1H); 7.25-7.50 (m, 13H); 7.63 (s, 1H); 8.50-8.54 (m, 1H).

EXAMPLE 24

2(R)-(tert-Butoxycarbonylethyl)-2-[3(S)-(4(S)-phenyloxazolidin-2-on-3-yl)-4(R)-(2-styryl)azetidin-2-on-1-yl]acetic acid N-(3-trifluoromethylbenzyl) amide.

The imine prepared from 1.15 g (3.20 mmol) of D-glutamic acid γ-t-butyl ester α-(3-trifluoromethyl)benzylamide and cinnamaldehyde was combined with 2-(4(S)-phenyloxazolidin-2-on-3-yl) acetyl chloride (Example 1) to give 1.84 g (85%) of Example 24 after flash column chromatography purification (70:30 hexanes/ethyl acetate); $^1$H NMR (CDCl$_3$) δ 1.37 (s, 9H); 2.23-2.39 (m, 4H); 3.71-3.75 (m, 1H); 4.13-4.18 (m, 1H); 4.31 (d, J=4.9 Hz, 1H); 4.44-4.51 (m, 2H); 4.56-4.68 (m, 2H); 4.71-4.76 (m, 1H); 6.26 (dd, J=9.5 Hz, J=15.8 Hz, 1H); 6.71 (d, J=15.8 Hz, 1H); 7.25-7.52 (m, 13H); 7.63 (s, 1H); 8.25-8.30 (m, 1H).

EXAMPLE 25

2(S)-(tert-Butoxycarbonylethyl)-2-[3(S)-(4(S)-phenyloxazolidin-2-on-3-yl)-4(R)-(2-styryl)azetidin-2-on-1-yl]acetic acid N-(4-cyclohexyl)piperazinamide.

The imine prepared from 2.58 g (5.94 mmol) of L-glutamic acid γ-t-butyl ester α-(4-cyclohexyl)piperazinamide and cinnamaldehyde was combined with 2-(4(S)-phenyloxazolidin-2-on-3-yl) acetyl chloride (Example 1) to give 3.27 g (94%) of Example 25 after flash column chromatography purification (95:5 dichloromethane/methanol); $^1$H NMR (CDCl$_3$) δ 1.32 (s, 9H); 1.10-1.18 (m, 1H); 1.20-1.31 (m, 2H); 1.38-1.45 (m, 2H); 1.61-1.66 (m, 1H); 1.84-1.89 (m, 2H); 1.95-2.01 (m, 1H); 2.04-2.14 (m, 3H); 2.20-2.24 (m, 1H); 2.29-2.35 (m, 1H); 2.85-2.92 (m, 1H); 3.24-3.32 (m, 1H); 3.36-3.45 (m, 2H); 3.80-3.86 (m, 1H); 4.08 (t, J=8.3 Hz, 1H); 4.27 (d, J=5.0 Hz, 1H); 4.31-4.55 (m, 4H); 4.71 (t, J=8.3 Hz, 1H); 4.83-4.90 (m, 1H); 6.18 (dd, J=9.1 Hz, J=15.9 Hz, 1H); 6.67 (d, J=15.9 Hz, 1H); 7.25-7.44 (m, 10H); 8.22 (br, 1H).

EXAMPLE 25A tert-Butyl 2(S)-(2-(4-cyclohexylpiperazin-1-ylcarbonyl)ethyl)-2-[3(S)-(4(S)-phenyloxazolidin-2-on-3-yl)-4(R)-(2-styryl)azetidin-2-on-1-yl]acetate The imine prepared from 1.282 g (3.63 mmol) of L-glutamic acid α-t-butyl, ester γ-(4-cyclohexyl)piperazinamide and cinnamaldehyde was combined with 2-(4(S)-phenyloxazolidin-2-on-3-yl) acetyl chloride (Example 1) to give 1.946 g (80%) of Example 25A after flash column chromatography purification (50:50 hexanes/ethyl acetate); $^1$H NMR (CDCl$_3$) δ 1.15-1.26 (m, 6H); 1.39 (s, 9H); 1.55-1.64 (m, 2H); 1.77-1.83 (m, 3H); 2.22-2.35 (m, 2H); 2.40-2.50 (m, 6H); 2.75-2.79 (m, 1H); 3.43-3.48 (m, 1H); 3.56-3.60 (m, 2H); 3.75-3.79 (in, 1H); 4.10 (t, J=8.3 Hz, 1H); 4.31-4.35 (m, 2H); 4.58 (t, J=8.8 Hz, 1H); 4.73 (t, J=8.4 Hz, 1H); 6.17 (dd, J=8.6 Hz, J=16.0 Hz, 1H); 6.65 (d, J=16.0 Hz, 1H); 7.27-7.42 (m, 10H).

EXAMPLE 25B

2(R)-(tert-Butoxycarbonylmethyl)-2-[3(S)-(4(S)-phenyloxazolidin-2-on-3-yl)-4(R)-(2-styryl)azetidin-2-on-1-yl]acetic acid N-(2-fluoro-3-trifluoromethylbenzyl)amide.

The imine prepared from 0.256 g (0.70 mmol) of D-aspartic acid β-t-butyl ester α-(2-fluoro-3-trifluoromethyl)benzylamide and cinnamaldehyde was combined with 2-(4(S)-phenyloxazolidin-2-on-3-yl) acetyl chloride (Example 1) to give 0.287 g (60%) of Example 25B after flash column chromatography purification (70:30 hexanes/ethyl acetate); $^1$H NMR (CDCl$_3$) δ 1.38 (s, 9H); 3.12 (dd, J=4.0 Hz, J=17.8 Hz, 1H); 3.20 (dd, J=10.4 Hz, J=17.8 Hz, 1H); 4.05 (dd, J=3.9 Hz, J=10.4 Hz, H); 4.14 (dd, J=J'=8.2 Hz, 1H); 4.25 (d, J=4.9 Hz, 1H); 4.59-4.67 (m, 4H); 4.74 (t, J=8.3 Hz, 1H); 6.36 (dd, J=9.6 Hz, J=15.8 Hz, 1H); 6.83 (d, J=15.8 Hz, 1H); 7.02-7.07 (m, 1H); 7.28-7.55 (m, 12H); 8.44-8.48 (m, 1H).

EXAMPLE 25C

2(R)-(tert-Butoxycarbonylmethyl)-2-[3(S)-(4(S)-phenyloxazolidin-2-on-3-yl)-4(R)-(2-styryl)azetidin-2-on-1-yl]acetic acid N-[(S)-α-methylbenzyl]amide.

The imine prepared from 0.167 g (0.57 mmol) of D-aspartic acid β-t-butyl ester [(S)-α-methylbenzyl]amide and cinnamaldehyde was combined with 2-(4(S)-phenyloxazolidin-2-on-3-yl) acetyl chloride (Example 1) to give 0.219 g (63%) of Example 25C after flash column chromatography purification (70:30 hexanes/ethyl acetate); $^1$H NMR (CDCl$_3$) δ 1.35 (s, 9H); 1.56 (d, J=7.0 Hz, 3H); 2.97 (dd, J=3.5 Hz, J=18.0 Hz, 1H); 3.15 (dd, J=11.0 Hz, J=17.5 Hz, 1H); 4.01 (dd, J=3.0 Hz, J=11.0 Hz, 1H); 4.14 (t, J=8.5 Hz, 1H); 4.24 (d, J=5.0 Hz, 1H); 4.57 (dd, J=5.0 Hz, J=9.5 Hz, 1H); 4.64 (t, J=8.8 Hz, 1H); 5.07 (t, J=8.5 Hz, 1H); 5.03-5.09 (m, 1H); 6.43 (dd, J=9.5 Hz, J=16.0 Hz, 1H); 6.83 (d, J=16.0 Hz, 1H); 7.16-7.20 (m, 1H); 7.27-7.49 (m, 14H); 8.07-8.10 (m, 1H).

EXAMPLE 25D

2(R)-(tert-Butoxycarbonylmethyl)-2-[3(S)-(4(S)-phenyloxazolidin-2-on-3-yl)-4(R)-(2-styryl)azetidin-2-on-1-yl]acetic acid N-[(R)-α-methylbenzyl]amide.

The imine prepared from 0.187 g (0.46 mmol) of D-aspartic acid β-t-butyl ester [(R)-α-methylbenzyl]amide and cinnamaldehyde was combined with 2-(4(S)-phenyloxazolidin-2-on-3-yl) acetyl chloride (Example 1) to give 0.25 g (64%) of Example 25D after flash column chromatography purification (70:30 hexanes/ethyl acetate); $^1$H NMR (CDCl$_3$) δ 1.36 (s, 9H); 1.59 (d, J=7.1 Hz, 3H); 3.10 (dd, J=3.5 Hz, J=17.8 Hz, 1H); 3.22 (dd, J=10.9 Hz, J=17.8 Hz, 1H); 3.93 (dd, J=3.5 Hz, J=10.8 Hz, 1H); 4.14 (t, J=8.1 Hz, 1H); 4.24 (d, J=5.0 Hz, 1H); 4.58 (dd, J=5.0 Hz, J=9.5 Hz, 1H); 4.65 (t, J=8.7 Hz, 1H); 4.74 (t, J=8.2 Hz, 1H); 5.06-5.14 (m, 1H); 6.32 (dd, J=9.5 Hz, J=15.8 Hz, 1H); 6.74 (d, J=15.8 Hz, 1H); 7.19-7.43 (m, 15H); 8.15-8.18 (m, 1H).

EXAMPLE 25E

2(R)-(tert-Butoxycarbonylmethyl)-2-[3(S)-(4(S)-phenyloxazolidin-2-on-3-yl)-4(R)-(2-styryl)azetidin-2-on-1-yl]acetic acid N-methyl-N-(3-trifluoromethylbenzyl)amide.

The imine prepared from 0.195 g (0.41 mmol) of D-aspartic acid β-t-butyl ester α-[N-methyl-N-(3-trifluoromethylbenzyl)]amide and cinnamaldehyde was combined with 2-(4(S)-phenyloxazolidin-2-on-3-yl) acetyl chloride (Example 1) to give 0.253 g (69%) of Example 25E after flash column chromatography purification (70:30 hexanes/ethyl acetate); $^1$H NMR (CDCl$_3$) δ 1.36 (s, 9H); 2.53 (dd, J=4.0 Hz, J=17.0 Hz, 1H); 3.06 (dd, J=10.8 Hz, J=16.8 Hz; 1H); 3.13 (s, 3H); 4.12 (dd, J=8.0 Hz, J=9.0 Hz, 1H); 4.26 (d, J=5.0 Hz, H); 4.38 (d, J=15.0 Hz, 1H); 4.46 (dd, J=5.0 Hz, J=9.5 Hz, 1H); 4.56 (t, J=6.8 Hz, 1H); 4.70-4.79 (m, 2H); 5.27 (dd, J=4.0 Hz, J=11.0 Hz, 1H); 6.22 (dd, J=9.3 Hz, J=15.8 Hz, 1H); 6.73 (d, J=15.8 Hz, 1H); 7.33-7.45 (m, 14H).

EXAMPLE 25F

2(S)-(tert-Butoxycarbonylethyl)-2-[3(S)-(4(S)-phenyloxazolidin-2-on-3-yl)-4(R)-(2-chlorostyr-2-yl)azetidin-2-on-1-yl]acetic acid N-(3-trifluoromethylbenzyl)amide.

The imine prepared from 1.62 g (4.44 mmol) of L-glutamic acid γ-t-butyl ester α-(3-trifluoromethyl)benzylamide and α-chlorocinnamaldehyde was combined with 2-(4(S)-phenyloxazolidin-2-on-3-yl) acetyl chloride (Example 1) to give 0.708 g (22%) of Example 25F after flash column chromatography purification (70:30 hexanes/ethyl acetate); $^1$H NMR (CDCl$_3$) δ 1.35 (s, 9H); 1.68 (brs, 1H); 2.19-2.35 (m, 2H); 2.40-2.61 (m, 2H); 4.13 (dd, J=7.5 Hz, J=9.0 Hz, 1H); 4.22 (t, J=7.0 Hz, 1H); 4.34 (d, J=4.5 Hz, 1H); 4.45 (dd, J=5.5 Hz, J=15.0 Hz, 1H); 4.51-4.60 (m, 3H); 4.89 (dd, J=7.5 Hz, J=8.5 Hz, 1H); 6.89 (s, 1H); 7.28-7.54 (m, 14H).

EXAMPLE 25G

2(R)-(tert-Butoxycarbonylmethyl)-2-[3(S)-(4(S)-phenyloxazolidin-2-on-3-yl)-4(R)-(2'-methoxystyr-2-yl)azetidin-2-on-1-yl]acetic acid N-(3-trifluoromethylbenzyl)amide.

The imine prepared from 0.34 g (0.98 mmol) of D-aspartic acid β-t-butyl ester α-(3-trifluoromethylbenzyl)amide and 2'-methoxycinnamaldehyde was combined with 2-(4(S)-phenyloxazolidin-2-on-3-yl) acetyl chloride (Example 1) to give 0.402 g (59%) of Example 25G after flash column chromatography purification (70:30 hexanes/ethyl acetate);

$^1$H NMR (CDCl$_3$) δ 1.35 (s, 9H); 1.68 (brs, 1H); 2.19-2.35 (m, 2H); 2.40-2.61 (m, 2H); 4.13 (dd, J=7.5 Hz, J=9.0 Hz, 1H); 4.22 (t, J=7.0 Hz, 1H); 4.34 (d, J=4.5 Hz, 1H); 4.45 (dd, J=5.5 Hz, J=15.0 Hz, 1H); 4.51-4.60 (m, 3H); 4.89 (dd, J=7.5 Hz, J=8.5 Hz, 1H); 6.89 (s, 1H); 7.28-7.54 (m, 14H).

EXAMPLE 25H tert-Butyl (2R)-(Benzyloxymethyl)-2-[3(S)-(4(S)-phenyloxazolidin-2-on-3-yl)-4(R)-(2-styryl)azetidin-2-on-1-yl]acetate.

The imine prepared from 0.329 g (1.31 mmol) of O-(benzyl)-D-serine t-butyl ester and cinnamaldehyde was combined with 2-(4(S)-phenyloxazolidin-2-on-3-yl) acetyl chloride (Example 1) to give 0.543 g (73%) of Example 25H after flash column chromatography purification (90:10 hexanes/ethyl acetate); $^1$H NMR (CDCl$_3$) δ 1.39 (s, 9H); 3.56 (dd, J=2.7 Hz, J=9.5 Hz, 1H); 3.82 (dd, J=4.8 Hz, J=9.5 Hz, 1H); 4.11 (t, J=8.3 Hz, 1H); 4.21-4.29 (m, 2H); 4.50-4.58 (m, 3H); 4.71-4.78 (m, 2H); 6.19 (dd, J=9.1 Hz, J=16.0 Hz, 1H); 6.49 (d, J=16.0 Hz, 1H); 7.07-7.11 (m, 1H); 7.19-7.40 (m, 14H).

EXAMPLE 26

General Procedure for Hydrolysis of a tert-Butyl Ester

A solution of tert-butyl ester derivative in formic acid, typically 1 g in 10 mL, is stirred at ambient temperature until no more ester is detected by thin layer chromatography (dichloromethane 95%/methanol 5%), a typical reaction time being around 3 hours. The formic acid is evaporated under reduced pressure; the resulting solid residue is partitioned between dichloromethane and saturated aqueous sodium bicarbonate. The organic layer is evaporated to give an off-white solid that may be used directly for further reactions, or recrystallized from an appropriate solvent system if desired.

Examples 27-34 and 34A-34H were prepared from the appropriate tert-butyl ester according to the procedure used in Example 26.

EXAMPLE 27

2(R,S)-(Carboxy)-2-[3(S)-(4(S)-phenyloxazolidin-2-on-3-yl)-4(R)-(2-styryl)azetidin-2-on-1-yl]acetic acid N-(3-trifluoromethylbenzyl)amide.

Example 18 (0.30 g, 0.46 mmol) was hydrolyzed to give 0.27 g (quantitative yield) of Example 27 as an off-white solid; $^1$H NMR (CDCl$_3$) δ 4.17-5.28 (m, 9H); 6.21-6.29 (m, 1H), 6.68-6.82 (m, 1H); 7.05-7.75 (m, 13H); 9.12-9.18 (m, 1H).

EXAMPLE 28

2(S)-(Carboxymethyl)-2-[3(S)-(4(S)-phenyloxazolidin-2-on-3-yl)-4(R)-(2-styryl)azetidin-2-on-1-yl] acetic acid N-(3-trifluoromethylbenzyl)amide.

Example 19 (1.72 g, 2.59 mmol) was hydrolyzed to give 1.57 g (quantitative yield) of Example 28 as an off-white solid; $^1$H NMR (CDCl$_3$) δ 2.61 (dd, J=9.3 Hz, J=16.6 Hz, 1H); 3.09-3.14 (m, 1H); 4.10-4.13 (m, 1H); 4.30 (d, J=4.5 Hz, 1H); 4.39-4.85 (m, 6H); 6.20 (dd, J=9.6 Hz, J=15.7 Hz, 1H); 6.69 (d, J=15.8 Hz, 1H); 7.12-7.15 (m, 2H); 7.26-7.50 (m, 11H); 7.61 (s, 1H); 8.41-8.45 (m, 1H).

EXAMPLE 29

2(S)-(Carboxyethyl)-2-[3(S)-(4(S)-phenyloxazolidin-2-on-3-yl)-4(R)-(2-styryl)azetidin-2-on-1-yl] acetic acid N-(3-trifluoromethylbenzyl)amide.

Example 20 (4.97 g, 7.34 mmol) was hydrolyzed to give 4.43 g (97%) of Example 29 as an off-white solid; $^1$H NMR (CDCl$_3$) δ 1.92-2.03 (m,1H); 2.37-2.51 (m, 3H); 4.13-4.19 (m, 1H); 3.32 (d, J=4.9 Hz, 1H); 4.35-4.39 (m, 1H); 4.44 (dd, J=5.9 Hz, J=14.9 Hz, 1H); 4.50-4.57 (m, 2H); 4.61-4.67 (m, 1H); 4.70-4.76 (m, 1H); 6.24 (dd, J=9.6 Hz, J=15.8 Hz, 1H); 6.70 (d, J=15.8 Hz, 1H); 7.18-7.47 (m, 14H).

EXAMPLE 30

2(S)-(Carboxymethyl)-2-[3(S)-(4(S)-phenyloxazolidin-2-on-3-yl)-4(R)-(2-styryl)azetidin-2-on-1-yl] acetic acid N-[4-(2-phenylethyl)]piperazinamide.

Example 21 (1.88 g, 2.78 mmol) was hydrolyzed to give 1.02 g (60%) of Example 30 as an off-white solid; $^1$H NMR (CDCl$_3$) δ 2.63 (dd, J=6.0 Hz, J=16.5 Hz, 1H); 2.75-2.85 (m, 1H); 3.00 (dd, J=8.2 Hz, J=16.6 Hz, 1H); 3.13-3.26 (m, 4H); 3.37-3.56 (m, 4H); 3.86-4.00 (m, 1H); 4.05-4.11 (m, 1H); 4.24 (d, J=5.0 Hz, 1H); 4.46-4.66 (m, 1H); 4.65-4.70 (m, 1H); 5.10-5.15 (m, 1H); 6.14 (dd, J=9.3 Hz, J=15.9 Hz, 1H); 6.71 (d, J=15.9 Hz, 1H); 7.22-7.41 (m, 0.15H); 12.02 (s, 1H).

EXAMPLE 31

2(S)-(Carboxyethyl)-2-[3(S)-(4(S)-phenyloxazolidin-2-on-3-yl)-4(R)-(2-styryl)azetidin-2-on-1-yl] acetic acid N-[4-(2-phenylethyl)]piperazinamide.

Example 22 (0.383 g, 0.55 mmol) was hydrolyzed to give 0.352 g (quantitative yield) of Example 31 as an off-white solid; $^1$H NMR (CDCl$_3$) δ 1.93-2.01 (m, 1H); 2.07-2.36 (m, 6H); 2.82-2.90 (m, 1H); 3.00-3.20 (m, 4H); 3.36-3.54 (m, 4H); 3.74-3.82 (m, 1H); 4.06-4.11 (m, 1H); 4.29 (d, J=4.9 Hz, 1H); 4.33-4.46 (m, 2H); 4.50-4.58 (m, 2H); 4.67-4.72 (m, 1H); 4.95-5.00 (m, 1H); 6.18 (dd, J=9.2 Hz, J=16.0 Hz, 1H); 6.67 (d, J=15.9 Hz, 1H); 7.19-7.42 (m, 15H); 8.80 (brs, 1H).

EXAMPLE 32

2(R)-(Carboxymethyl)-2-[3(S)-(4(S)-phenyloxazolidin-2-on-3-yl)-4(R)-(2-styryl)azetidin-2-on-1-yl] acetic acid N-(3-trifluoromethylbenzyl)amide.

Example 23 (1.51 g, 2.27 mmol) was hydrolyzed to give 1.38 g (quantitative yield) of Example 32 as an off-white solid.

EXAMPLE 33

2(R)-(Carboxyethyl)-2-[3(S)-(4(S)-phenyloxazolidin-2-on-3-yl)-4(R)-(2-styryl)azetidin-2-on-1-yl] acetic acid N-(3-trifluorormethylbenzyl)amide Example 24 (0.604 g, 0.89 mmol) was hydrolyzed to give 0.554 g (quantitative yield) of Example 33 as an off-white solid.

EXAMPLE 34

2(S)-(Carboxyethyl)-2-[3(S)-(4(S)-phenyloxazolidin-2-on-3-yl)-4(R)-(2-styryl)azetidin-2-on-1-yl] acetic acid N-(4-cyclohexyl)piperazinamide Example 25 (0.537 g, 0.80 mmol) was hydrolyzed to give 0.492 g (quantitative yield) of Example 34 as an off-white solid; $^1$H NMR (CDCl$_3$) δ 1.09-1.17 (m, 1H); 1.22-1.33 (m, 2H); 1.40-1.47 (m, 2H); 1.63-1.67 (m, 1H); 1.85-1.90 (m, 2H); 1.95-2.00 (m, 1H); 2.05-2.15 (m, 3H); 2.20-2.24 (m, 1H); 2.30-2.36 (m, 1H); 2.85-2.93 (m, 1H); 3.25-3.33 (m, 1H); 3.36-3.46 (m, 2H); 3.81-3.87 (m, 1H); 4.08 (t, J=8.3 Hz, 1H); 4.28 (d, J=5.0 Hz, 1H); 4.33-4.56 (m, 4H); 4.70 (t, J=8.3 Hz, 1H); 4.83-4.19 (m, 1H); 6.17 (dd, J=9.1 Hz, J=15.9 Hz, 1H); 6.67 (d, J=15.9 Hz, 1H); 7.25-7.44 (m, 10H); 8.22 (brs, 1H).

EXAMPLE 34A

2(S)-(2-(4-Cyclohexylpiperazin-1-ylcarbonyl)ethyl)-2-[3(S)-(4(S)-phenyloxazolidin-2-on-3-yl)-4(R)-(2-styryl)azetidin-2-on-1-yl]acetic acid.

Example 25A (0.787 g, 1.28 mmol) was hydrolyzed to give 0.665 g (92%) of Example 34A as an off-white solid; $^1$H NMR (CDCl$_3$) δ 1.05-1.13 (m, 1H); 1.20-1.40 (m, 5H); 1.60-1.64 (m, 1H); 1.79-1.83 (m, 2H); 2.00-2.05 (m, 2H); 2.22-2.44 (m, 3H); 2.67-2.71 (m, 1H); 2.93-3.01 (m, 4H); 3.14-3.18 (m, 1H); 3.38-3.42 (m, 1H); 3.48-3.52 (m, 1H); 3.64-3.69 (m, 1H); 4.06-4.14 (m, 2H); 4.34-4.43 (m, 2H); 4.56 (t, J=8.8 Hz, 1H); 4.73 (t, J=8.4 Hz, 1H); 6.15 (dd, J=9.1 Hz, J=16.0 Hz, 1H); 6.65 (d, J=16.0 Hz, 1H); 7.25-7.42 (m, 10H).

EXAMPLE 34B

2(R)-(Carboxymethyl)-2-[3(S)-(4(S)-phenyloxazolidin-2-on-3-yl)-4(R)-(2-styryl)azetidin-2-on-1-yl] acetic acid N-(2-fluoro-3-trifluoromethylbenzyl) carboxamide.

Example 25B (0.26 g, 0.38 mmol) was hydrolyzed to give 0.238 g (quantitative yield) of Example 34B as an off-white solid; $^1$H NMR (CDCl$_3$) δ 3.27 (d, J=7.2 Hz, 1H); 4.06 (t, J=7.2 Hz, 1H); 4.15 (t, J=8.1 Hz, 1H); 4.27 (d, J=4.8 Hz, 1H); 4.56-4.76 (m, 5H); 6.34 (dd, J=9.5 Hz, J=15.7 Hz, 1H); 6.80 (d, J=15.7 Hz, 1H); 7.06 (t, J=7.7 Hz, 1H); 7.31-7.54 (m, 12H); 8.58 (t, J=5.9 Hz, 1H).

EXAMPLE 34C

2(R)-(Carboxymethyl)-2-[3(S)-(4(S)-phenyloxazolidin-2-on-3-yl)-4(R)-(2-styryl)azetidin-2-on-1-yl] acetic acid N-[(S)-α-rmethylbenzyl]amide.

Example 25C (0.215 g, 0.35 mmol) was hydrolyzed to give 0.195 g (quantitative yield) of Example 34C as an off-white solid; $^1$H NMR (CDCl$_3$) δ 1.56 (d, J=7.0 Hz, 1H); 3.10 (dd, J=4.5 Hz, J=17.9 Hz, 1H); 3.18 (dd, J=9.8 Hz, J=17.9 Hz, 1H); 4.00 (dd, J=4.5 Hz, J=9.7 Hz, 1H); 4.14 (t, J=8.2 Hz, 1H); 4.26 (d, J=4.7 Hz, 1H); 5.02-5.09 (m, 1H); 6.41 (dd, J=9.4 Hz, J=15.8 Hz, 1H); 6.78 (d, J=15.8 Hz, 1H); 7.18 (t, J=7.3 Hz, 1H); 7.26-7.43 (m, 12H); 8.29 (d, J=8.2 Hz, 1H).

EXAMPLE 34D

2(R)-(Carboxymethyl)-2-[3(S)-(4(S)-phenyloxazolidin-2-on-3-yl)-4(R)-(2-styryl)azetidin-2-on-1-yl]acetic acid N-[(R)-α-methylbenzyl]amide.

Example 25D (0.22 g, 0.35 mmol) was hydrolyzed to give 0.20 g (quantitative yield) of Example 34D as an off-white solid; $^1$H NMR (CDCl$_3$) δ 1.59 (d, J=7.0 Hz, 1H); 3.25 (d, J=7.0 Hz, 2H); 3.92 (t, J=7.3 Hz, 1H); 4.15 (t, J=8.3 Hz, 1H); 4.26 (d, J=5.0 Hz, 1H); 4.52 (dd, J=4.8 Hz, J=9.3 Hz, 1H); 4.65 (t, J=8.8 Hz, 1H); 4.72 (t, J=8.3 Hz, 1H); 5.07-5.28 (m, 1H); 6.29 (dd, J=9.5 Hz, J=15.6 Hz, 1H); 6.71 (d, J=16.0 Hz, 1H); 7.20-7.43 (m, 13H); 8.31 (d, J=8.0 Hz, 1H).

EXAMPLE 34E

2(R)-(Carboxymethyl)-2-[3(S)-(4(S)-phenyloxazolidin-2-on-3-yl)-4(R)-(2-styryl)azetidin-2-on-1-yl]acetic acid N-methyl-N-(3-trifluoromethylbenzyl)amide.

Example 25E (0.253 g, 0.37 mmol) was hydrolyzed to give 0.232 g (quantitative yield) of Example 34E as an off-white solid; $^1$H NMR (CDCl$_3$) δ 3.07-3.15 (m, 4H); 4.13 (t, J=8.2 Hz, 1H); 4.30 (d, J=4.9 Hz, 1H); 4.46-4.78 (m, 5H); 5.23 (dd, J=4.6 Hz, J=9.7 Hz, 1H); 6.20 (dd, J=9.4 Hz, J=15.9 Hz, 1H); 6.73 (d, J=15.9 Hz, 1H); 7.25-7.43 (m, 15H).

EXAMPLE 34F

2(S)-(Carboxyethyl)-2-[3(S)-(4(S)-phenyloxazolidin-2-on-3-yl)-4(R)-(2-chlorostyr-2-yl)azetidin-2-on-1-yl]acetic acid N-(3-trifluoromethylbenzyl)amide.

Example 25F (0.707 g, 0.99 mmol) was hydrolyzed to give 0.648 g (99%) of Example 34F as an off-white solid; $^1$H NMR (CDCl$_3$) δ 2.22-2.28 (m,2H); 2.49-2.64 (m, 2H); 4.09 (t, J=8.0 Hz, 1H); 4.25-4.62 (m, 6H); 4.87 (t, J=8.0 Hz, 1H); 6.88 (s, 1H); 7.25-7.66 (m, 15H).

EXAMPLE 34G

2(R)-(Carboxymethyl)-2-[3(S)-(4(S)-phenyloxazolidin-2-on-3-yl)-4(R)-(2'-methoxystyr-2-yl)azetidin-2-on-1-yl]acetic acid N-(3-trifluoromethylbenzyl)amide Example 25G (0.268 g, 0.39 mmol) was hydrolyzed to give 0.242 g (98%) of Example 34G as an off-white solid; $^1$H NMR (CDCl$_3$) δ 3.26 (d, J=7.1 Hz, 1H); 3.79 (s, 3H); 4.14 (t, J=8.2 Hz, 1H); 4.25 (d, J=4.5 Hz, 1H); 4.51 (dd, J=5.9 Hz, J Hz, 1H); 4.53-4.66 (m, 4H); 6.36 (dd, J=9.4 Hz, J=15.8 Hz, 1H); 8.88 (t, J=8.2 Hz, 1H); 6.70 (d, J=15.8 Hz, 1H); 7.18 (d, J=6.5 Hz, 1H); 7.25-7.48 (m, 10H); 7.48 (s, 1H); 8.66-8.69 (m, 1H).

EXAMPLE 34H (2R)-(Benzyloxymethyl)-2-[3(S)-(4(S)-phenyloxazolidin-2-on-3-yl)-4(R)-(2-styryl)azetidin-2-on-1-yl]acetic acid.

Example 25H (0.16 g, 0.28 mmol) was hydrolyzed to give 0.144 g of Example 34H as an off-white solid; $^1$H NMR (CDCl$_3$) δ 3.65 (dd, J=4.0 Hz, J=9.5 Hz, 1H); 3.82 (dd, J=5.5 Hz, J=9.5 Hz, 1H); 4.11 (dd, J=7.8 Hz, J=8.8 Hz, 1H); 4.33 (s, 2H); 4.50 (d, J=5.0 Hz, 1H); 4.57 (t, J=9.0 Hz, 1H); 4.67 (dd, J=4.0 Hz, J=5.0 Hz, 1H); 4.69 (dd, J=5.0 Hz, J=9.5 Hz, 1H); 4.75 (t, J=8.0 Hz, 1H); 6.17 (dd, J=9.3 Hz, J=15.8 Hz, 1H); 6.55 (d, J=16.0 Hz, 1H); 7.09-7.12 (m, 2H); 7.19-7.42 (m, 13H).

EXAMPLE 35

2(S)-[4-(2-phenylethyl)piperazin-1-yl-carbonylethyl]-2-[3(S)-(4(S)-phenyloxazolidin-2-on-3-yl)-4(R)-(2-styryl)azetidin-2-on-1-yl]acetic acid N-(3-trifluoromethylbenzyl)amide.

Using the procedure of Example 6, except that N-benzyloxycarbonyl-D-aspartic acid β-t-butyl ester monohydrate was replaced with the carboxylic acid of Example 29 and 3-(trifluoromethyl)benzyl amine was replaced with 4-(2-phenylethyl)piperazine, the title compound was prepared; $^1$H NMR (CDCl$_3$) δ 2.21-2.23 (m, 1H); 2.25-2.45 (m, 6H); 2.52-2.63 (m, 3H); 2.72-2.82 (m, 2H); 3.42-3.48 (m, 2H); 3.52-3.58 (m, 1H); 4.13-4.18 (m, 1H); 4.26 (dd, J=5.1 Hz, J=8.3 Hz, 1H); 4.29 (d, J=5.0 Hz, 1H); 4.44 (dd, J=6.0 Hz, J=15.0 Hz, 1H); 4.54 (dd, J=6.2 Hz, J=14.9 Hz, 1H); 4.61-4.68 (m, 2H); 4.70-4.75 (m, 1H); 6.27 (dd, J=9.6 Hz, J=15.8 Hz, 1H); 6.73 (d, J=15.8 Hz, 1H); 7.16-7.60 (m, 19H); 8.07-8.12 (m, 1H); FAB$^+$(M+H)$^+$/z 794; Elemental Analysis calculated for C$_{45}$H$_{46}$F$_3$N$_5$O$_5$: C, 68.08; H, 5.84; N, 8.82; found: C, 67.94; H, 5.90; N, 8.64.

Examples 36-42 and 42A, shown in Table 6, were prepared using the procedure of Example 6, except that N-benzyloxycarbonyl-D-aspartic acid β-t-butyl ester monohydrate was replaced with Example 27, and 3-(trifluoromethyl)benzyl amine was replaced with the appropriate amine; all listed Examples exhibited an $^1$H NMR spectrum consistent with the assigned structure.

TABLE 6

| Example | A' |
|---|---|
| 36 | 2-(piperidin-1-yl)ethylamino |
| 37 | 4-(piperidin-1-yl)piperidin-1-yl |
| 38 | 4-(2-phenylethyl)piperazin-1-yl |
| 39 | 1-benzylpiperidin-4-ylamino |
| 40 | 4-butylpiperazin-1-yl |
| 41 | 4-isopropylpiperazin-1-yl |
| 42 | 4-cyclohexylpiperazin-1-yl |
| 42A | 4-[2-(piperidin-1-yl)ethyl]piperidin-1-yl |

Examples 43-86 and 86A, shown in Table 7, were prepared using the procedure of Example 6, except that N-benzyloxycarbonyl-D-aspartic acid β-t-butyl ester monohydrate was replaced with Example 28, and 3-(trifluoromethyl)

benzyl amine was replaced with the appropriate amine; all listed Examples exhibited an ¹H NMR spectrum consistent with the assigned structure.

TABLE 7

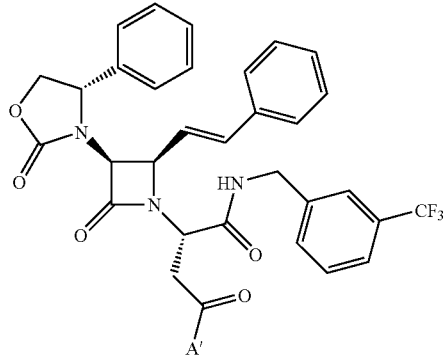

| Example | A' |
|---|---|
| 43 | 2-(piperidin-1-yl)ethylamino |
| 44 | 4-(piperidin-1-yl)piperidin-1-yl |
| 45 | 4-(phenylethyl)piperazin-1-yl |
| 46 | fur-2-ylmethylamino |
| 47 | 4-(pyrrolidin-1-yl)piperazin-1-yl |
| 48 | 4-(3-trifluoromethylphefly1)piperazin-1-yl |
| 49 | 4-(benzyloxycarbonyl)piperazin-1-yl |
| 50 | 4-[2-(2-hydroxyethoxy)ethyl]piperazin-1-yl |
| 51 | 4-benzylpiperazin-1-yl |
| 52 | 4-(3,4-methylenedioxybenzyl)piperazin-1-yl |
| 53 | 4-phenylpiperazin-1-yl |
| 54 | 4-(3-phenylprop-2-enyl)piperazin-1-yl |
| 55 | 4-ethylpiperazin-1-yl |
| 56 | 2-(diniethylamino)ethylamino |
| 57 | 4-(pyrrolidin-1-ylcarbonylmethyl)piperazin-1-yl |
| 58 | 4-(1-methylpiperidin-4-yl)piperazin-1-yl |
| 59 | 4-butylpiperazin-1-yl |
| 60 | 4-isopropylpiperazin-1-yl |
| 61 | 4-pyridylmethylamino |
| 62 | 3-(dimethylaxnino)propylamino |
| 63 | 1-benzylpiperidin-4-ylamino |
| 64 | N-benzyl-2-(dimethylamino)ethylamino |
| 65 | 3-pyridylmethylamino |
| 66 | 4-(cyclohexyl)piperazin-1-yl |
| 67 | 4-(2-cyclohexylethyl)piperazin-1-yl |
| 68 | 4-[2-(morpholin-4-yl)ethyl]piperazin-1-yl |
| 69 | 4-(4-tert-butylbenzyl)piperazin-1-yl |
| 70 | 4-[2-(piperidin-1-yl)ethyl]piperazin-1-yl |
| 71 | 4-[3-(piperidin-1-yl)propyl]piperazin-1-yl |
| 72 | 4-[2-(N,N-dipropylamino)ethyl]piperazin-1-yl |
| 73 | 4-[3-(N,N-diethylamino)propyl]piperazin-1-yl |
| 74 | 4-[2-(dimethylamino)ethyl]piperazin-1-yl |
| 75 | 4-[3-(pyrrolidin-1-yl)propyl]piperazin-1-yl |
| 76 | 4-(cyclohexylmethyl)piperazin-1-yl |
| 77 | 4-cyclopentylpiperazin-1-yl |
| 78 | 4-[2-(pyrrolidin-1-yl)ethyl]piperazin-1-yl |
| 79 | 4-[2-(thien-2-yl)ethyl]piperazin-1-yl |
| 80 | 4-(3-phenylpropyl)piperazin-1-yl |
| 81 | 4-[2-(N,N-diethylamino)ethyl]piperazin-1-yl |
| 82 | 4-benzylhomopiperazin-1-yl |
| 83 | 4-(bisphenylmethyl)piperazin-1-yl |
| 84 | 3-(4-methylpiperazin-1-yl)propylamino |
| 85 | (+)-3(S)-1-benzylpyrrolidin-3-ylamino |
| 86 | 2-pyridylmethylamino |
| 86A | 4-[2-(piperidin-1-yl)ethyl]piperidin-1-yl |

Examples 87-120 and 120A-120D, shown in Table 8, were prepared using the procedure of Example 6, except that N-benzyloxycarbonyl-D-aspartic acid β-t-butyl ester monohydrate was replaced with Example 29, and 3-(trifluoromethyl)benzyl amine was replaced with the appropriate amine; all listed Examples exhibited an ¹H NMR spectrum consistent with the assigned structure.

TABLE 8

| Example | A' |
|---|---|
| 87 | 2-(piperidin-1-yl)ethylamino |
| 88 | 4-(piperidin-1-yl)piperidin-1-yl |
| 89 | 2-(pyrid-2-yl)ethylamino |
| 90 | morpholin-4-ylanuino |
| 91 | 4-(pyrrolidin-1-yl)piperazin-1-yl |
| 92 | 4-(3-trifluorophenyl)piperazin-1-yl |
| 93 | 4-(benzyloxycarbonyl)piperazin-1-yl |
| 94 | 4-[2-(2-hydroxylethoxy)ethyl]piperazin-1-yl |
| 95 | 4-benzylpiperazin-1-yl |
| 96 | 4-(3,4-methylenedioxybenzyl)piperazin-1-yl |
| 97 | 4-phenylpiperazin-1-yl |
| 98 | 4-(3-phenylprop-2-enyl)piperazin-1-yl |
| 99 | 4-ethylpiperazin-1-yl |
| 100 | 2-(dimethylamino)ethylamino |
| 101 | 4-(pyrrolidin-1-ylcarbonylmethyl)piperazin-1-yl |
| 102 | 4-(1-methylpiperidin-4-yl)piperazin-1-yl |
| 103 | 4-butylpiperazin-1-yl |
| 104 | 4-isopropylpiperazin-1-yl |
| 105 | 4-pyridylmethylamino |
| 106 | 3-(dimethylamino)propylamino |
| 107 | 1-benzylpiperidin-4-ylamino |
| 108 | N-benzyl-2-(dimethylamino)ethylamino |
| 109 | 3-pyridylmethylamino |
| 110 | 4-cyclohexylpiperazin-1-yl |
| 111 | 4-(2-cyclohexylethyl)piperazin-1-yl |
| 112 | 4-[2-(morpholin-4-yl)ethyl]piperazin-1-yl |
| 113 | 4-(4-tert-butylbenzyl)piperazin-1-yl |
| 114 | 4-[2-(piperidin-1-yl)ethyl]piperazin-1-yl |
| 115 | 4-[3-(piperidin-1-yl)propyl]piperazin-1-yl |
| 116 | 4-[2-(diisopropylanhino)ethyl]piperazin-1-yl |
| 117 | 4-[3-(diethylamino)propyl]piperazin-1-yl |
| 118 | 4-(2-dimethylaminoethyl)piperazin-1-yl |
| 119 | 4-[3-(pyrrolidin-1-yl)propyl]piperazin-1-yl |
| 120 | 4-(cyclohexylmethyl)piperazin-1-yl |
| 120A | 4-[2-(piperidin-1-yl)ethyl]piperidin-1-yl |
| 120B | 4-propyl-piperazin-1-yl |
| 120C | 4-[N-(isopropyl)acetamid-2-yl]piperazin-1-yl |
| 120D | 3-benzyl-hexahydro-(1H)-1,3-diazepin-1-yl |

Examples 121-132, shown in Table 9, were prepared using the procedure of Example 6, except that N-benzyloxycarbonyl-D-aspartic acid β-t-butyl ester monohydrate was replaced with Example 30, and 3-(trifluoromethyl)benzyl amine was replaced with the appropriate amine; all listed Examples exhibited an ¹H NMR spectrum consistent with the assigned structure.

TABLE 9

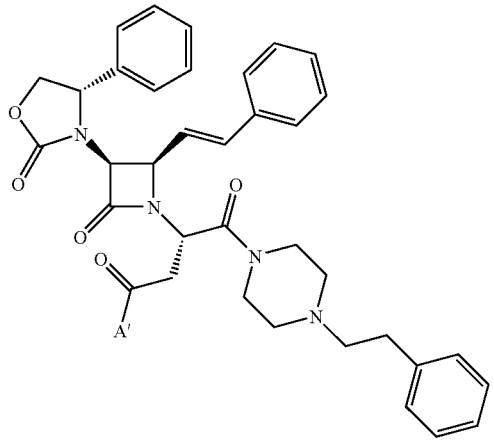

| Example | A' |
|---|---|
| 121 | 3-trifluoromethylbenzylamino |
| 122 | morpholin-4-ylamino |
| 123 | 2-(dimethylamino)ethylamino |
| 124 | 3-(dimethylamino)propylamino |
| 125 | cyclohexylamino |
| 126 | piperidin-1-yl |
| 127 | 2-methoxyethylamino |
| 128 | isopropylamino |
| 129 | isobutylamino |
| 130 | ethylamino |
| 131 | dimethylamino |
| 132 | methylamino |

Examples 133-134 and 134A-134F, shown in Table 10, were prepared using the procedure of Example 6, except that N-benzyloxycarbonyl-D-aspartic acid β-t-butyl ester monohydrate was replaced with Example 32, and 3-(trifluoromethyl)benzyl amine was replaced with the appropriate amine; all listed Examples exhibited an ¹H NMR spectrum consistent with the assigned structure.

TABLE 10

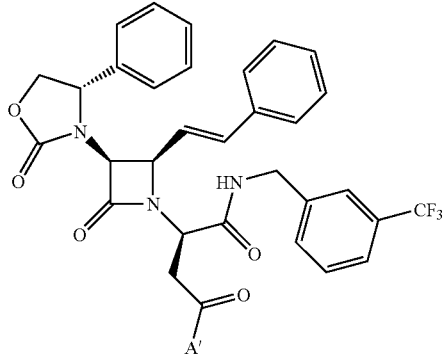

| Example | A' |
|---|---|
| 133 | 4-(piperidin-1-yl)piperidin-1-yl |
| 134 | 4-(2-phenylethyl)piperazin-1-yl |
| 134A | 4-[2-(pipridin-1-yl)ethyl]piperidin-1-yl |
| 134B | 4-(pyrrolidin-1-yl)piperazin-1-yl |
| 134C | 1-benzylpiperidin-4-ylamino |
| 134D | (pyridin-3-ylmethyl)amino |
| 134E | 3-(dimethylamino)propylamino |
| 134F | 3-(S)-(1-benzylpyrrolidin-3-yl)amino |

Examples 135-140, shown in Table 11, were prepared using the procedure of Example 6, except that N-benzyloxycarbonyl-D-aspartic acid β-t-butyl ester monohydrate was replaced with Example 33, and 3-(trifluoromethyl)benzyl amine was replaced with the appropriate amine; all listed Examples exhibited an ¹H NMR spectrum consistent with the assigned structure.

TABLE 11

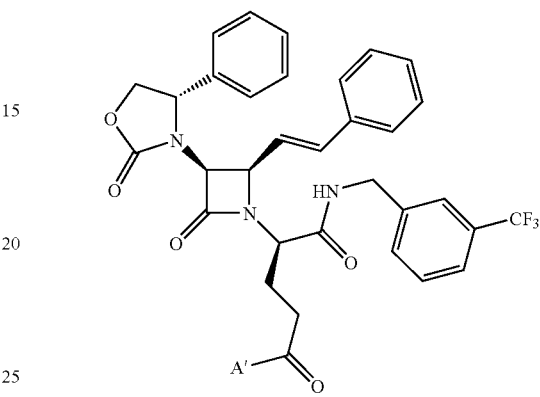

| Example | A' |
|---|---|
| 135 | 4-(piperidin-1-yl)piperidin-1-yl |
| 136 | 4-(2-phenylethyl)piperazin-1-yl |
| 137 | 4-butylpiperazin-1-yl |
| 138 | 4-isopropylpiperazin-1-yl |
| 139 | 4-cyclohexylpiperazin-1-yl |
| 140 | 4-(cyclohexylmethyl)piperazin-1-yl |

Examples 141-171, shown in Table 12, were prepared using the procedure of Example 6, except that N-benzyloxycarbonyl-D-aspartic acid β-t-butyl ester monohydrate was replaced with Example 34, and 3-(trifluoromethyl)benzyl amine was replaced with the appropriate amine; all listed Examples exhibited an ¹H NMR spectrum consistent with the assigned structure.

TABLE 12

| Example | A' |
|---|---|
| 141 | benzylamino |
| 142 | (2-methylbenzyl)amino |

TABLE 12-continued

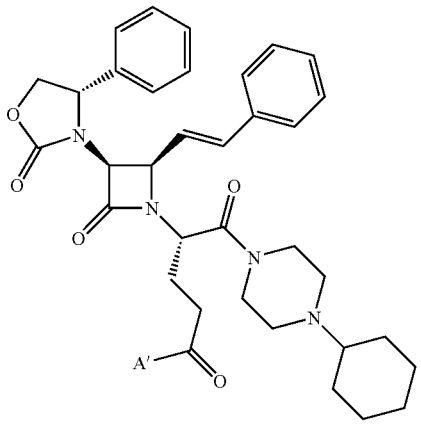

| Example | A' |
|---------|-----|
| 143 | (3-methylbenzyl)amino |
| 144 | (4-methylbenzyl)amino |
| 145 | (α-methylbenzyl) amino |
| 146 | N-benzyl-N-methylamino |
| 147 | N-benzyl-N-(t-butyl)amino |
| 148 | N-benzyl-N-butylamino |
| 149 | (3,5-dimethylbenzyl)amino |
| 150 | (2-phenylethyl)amino |
| 151 | dimethylamino |
| 152 | (3-trifluoromethoxybenzyl)amino |
| 153 | (3,4-dichlorobenzyl)amino |
| 154 | (3,5-dichlorobenzyl)amino |
| 155 | (2,5-dichlorobenzyl)amino |
| 156 | (2,3-dichlorobenzyl)amino |
| 157 | (2-fluoro-5-trifluoromethylbenzyl)amino |
| 158 | (4-fluoro-3-trifluoromethylbenzyl)amino |
| 159 | (3-fluoro-5-trifluoromethylbenzyl)amino |
| 160 | (2-fluoro-3-trifluoromethylbenzyl)amino |
| 161 | (4-chloro-3-trifluoromethylbenzyl)amino |
| 162 | indan-1-ylamino |
| 163 | 4-(2-hydroxybenzimidazol-1-yl)-piperidin-1-yl |
| 164 | 3(S)-(tert-butylaminocarbonyl)-1,2,3,4-tetrahydroisoquinolin-2-yl |
| 165 | (3,3-dimethylbutyl)amino |
| 166 | 4-hydroxy-4-phenylpiperidin-1-yl |
| 167 | (cyclohexylmethyl)amino |
| 168 | (2-phenoxyethyl)amino |
| 169 | 3,4-methylenedioxybenzylamino |
| 170 | 4-benzylpiperidin-1-yl |
| 171 | (3-trifluoromethylphenyl)amino |

Examples 172-221, shown in Table 13, were prepared using the procedure of Example 6, except that N-benzyloxycarbonyl-D-aspartic acid β-t-butyl ester monohydrate was replaced with Example 34A, and 3-(trifluoromethyl)benzyl amine was replaced with the appropriate amine; all listed Examples exhibited an ¹H NMR spectrum consistent with the assigned structure.

TABLE 13

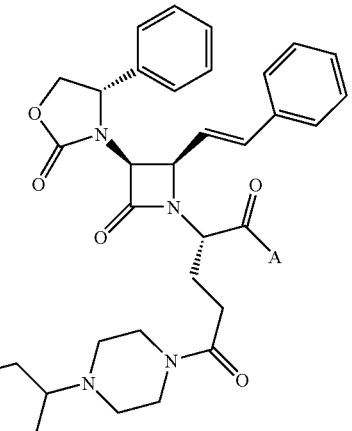

| Example | A' |
|---------|-----|
| 172 | (3-trifluoromethoxybenzyl)amino |
| 173 | (3,4-dichlorobenzyl)amino |
| 174 | (3,5-dichlorobenzyl)amino |
| 175 | (2,5-dichlorobenzyl)amino |
| 176 | (2,3-dichlorobenzyl)amino |
| 177 | (2-fluoro-5-trifluoromethylbenzyl)amino |
| 178 | (4-fluoro-3-trifluoromethylbenzyl)amino |
| 179 | (3-fluoro-5-trifluoromethylbenzyl)amino |
| 180 | (2-fluoro-3-trifluoromethylbenzyl)amino |
| 181 | (4-chloro-3-trifluoromethylbenzyl)amino |
| 182 | (2-trifluoromethylbenzyl)amino |
| 183 | (3-methoxybenzyl)amino |
| 184 | (3-fluorobenzyl)amino |
| 185 | (3,5-difluorobenzyl)amino |
| 186 | (3-chloro-4-fluorobenzyl)amino |
| 187 | (3-chlorobenzyl)amino |
| 188 | [3,5-bis(trifluoromethyl)benzyl]amino |
| 189 | (3-nitrobenzyl)amino |
| 190 | (3-bromobenzyl)amino |
| 191 | benzylamino |
| 192 | (2-methylbenzyl)amino |
| 193 | (3-methylbenzyl)amino |
| 194 | (4-methylbenzyl)amino |
| 195 | (α-methylbenzyl)amino |
| 196 | (N-methylbenzyl)amino |
| 197 | (N-tert-butylbenzyl)amino |
| 198 | (N-butylbenzyl)amino |
| 199 | (3,5-dimethylbenzyl)amino |
| 200 | (2-phenylethyl)amino |
| 201 | (3,5-dimethoxybenzyl)amino |
| 202 | (1R)-(3-methoxyphenyl)ethylamino |
| 203 | (1S)-(3-methoxyphenyl)ethylamino |
| 204 | (α,α-dimethylbenzyl)amino |
| 205 | N-methyl-N-(3-trifluoromethylbenzyl)amino |
| 206 | [(S)-α-methylbenzyl]amino |
| 207 | (1-phenylcycloprop-1-yl)amino |
| 208 | (pyridin-2-ylmethyl)amino |
| 209 | (pyridin-3-ylmethyl)amino |
| 210 | (pyridin-4-ylmethyl)amino |
| 211 | (fur-2-ylmethyl)amino |
| 212 | [(5-methylfur-2-yl)methyl]amino |
| 213 | (thien-2-ylmethyl)amino |
| 214 | [(S)-1,2,3,4-tetrahydro-1-naphth-1-yl]amino |
| 215 | [(R)-1,2,3,4-tetrahydro-1-naphth-1-yl]amino |
| 216 | (indan-1-yl)amino |
| 217 | (1-phenylcyclopent-1-yl)amino |
| 218 | (α,α-dimethyl-3,5-dimethoxybenzyl)amino |
| 219 | (2,5-dimethoxybenzyl)amino |
| 220 | (2-methoxybenzyl)amino |
| 221 | (α,α-2-trimethylbenzyl)amino |

EXAMPLE 222

2(R)-[[4-(Piperidin-1-yl)piperidin-1-yl]carbonylmethyl]-2-[3(S)-(4(S)-phenyloxazolidin-2-on-3-yl)-4(R)-(2-styryl)azetidin-2-on-1-yl]acetic acid N-(2-fluoro-3-trifluoromethylbenzyl)carboxamide Example 222 was prepared using the procedure of Example 6, except that N-benzyloxycarbonyl-D-aspartic acid β-t-butyl ester monohydrate was replaced with Example 34B, and 3-(trifluoromethyl)benzyl amine was replaced with 4-(piperidin-1-yl)piperidine; Example 222 exhibited an ¹H NMR spectrum consistent with the assigned structure.

EXAMPLE 223

2(R)-[[4-(Piperidin-1-yl)piperidin-1-yl]carbonylmethyl]-2-[3(S)-(4(S)-phenyloxazolidin-2-on-3-yl)-4(R)-(2-styryl)azetidin-2-on-1-yl]acetic acid N-[(S)-α-methylbenzyl]amide Example 223 was prepared using the procedure of Example 6, except that N-benzyloxycarbonyl-D-aspartic acid β-t-butyl ester monohydrate was replaced with Example 34C, and 3-(trifluoromethyl)benzyl amine was replaced with 4-(piperidin-1-yl)piperidine; Example 223 exhibited an ¹H NMR spectrum consistent with the assigned structure.

EXAMPLE 224

2(R)-[[4-(Piperidin-1-yl)piperidin-1-yl]carbonylmethyl]-2-[3(S)-(4(S)-phenyloxazolidin-2-on-3-yl)-4(R)-(2-styryl)azetidin-2-on-1-yl]acetic acid N-[(R)-α-methylbenzyl]amide Example 224 was prepared using the procedure of Example 6, except that N-benzyloxycarbonyl-D-aspartic acid β-t-butyl ester monohydrate was replaced with Example 34D, and 3-(trifluoromethyl)benzyl amine was replaced with 4-(piperidin-1-yl)piperidine; Example 223 exhibited an ¹H NMR spectrum consistent with the assigned structure.

EXAMPLE 225

2(R)-[[4-(Piperidin-1-yl)piperidin-1-yl]carbonylmethyl]-2-[3(S)-(4(S)-phenyloxazolidin-2-on-3-yl)-4(R)-(2-styryl)azetidin-2-on-1-yl]acetic acid N-methyl-N-(3-trifluoromethylbenzyl)amide Example 225 was prepared using the procedure of Example 6, except that N-benzyloxycarbonyl-D-aspartic acid β-t-butyl ester monohydrate was replaced with Example 34E, and 3-(trifluoromethyl)benzyl amine was replaced with 4-(piperidin-1-yl)piperidine; Example 223 exhibited an ¹H NMR spectrum consistent with the assigned structure.

Examples 226-230, shown in Table 14, were prepared using the procedure of Example 6, except that N-benzyloxycarbonyl-D-aspartic acid β-t-butyl ester monohydrate was replaced with Example 34F, and 3-(trifluoromethyl)benzyl amine was replaced with the appropriate amine; all listed Examples exhibited an ¹H NMR spectrum consistent with the assigned structure.

TABLE 14

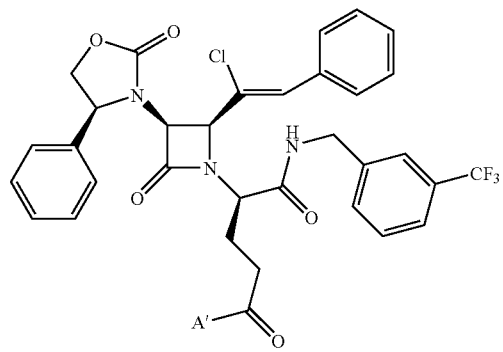

| Example | A' |
|---|---|
| 226 | 4-cyclohexylpiperazin-1-yl |
| 227 | 4-(pyrrolidin-1-yl)piperazin-1-yl |
| 228 | 4-ethylpiperazin-1-yl |
| 229 | 4-n-butylpiperazin-1-yl |
| 230 | 4-isopropylpiperazin-1-yl |

EXAMPLE 231

2(R)-[[4-Piperidin-1-yl)piperidin-1-yl]carbonylmethyl]-2-[3(S)-(4(S)-phenyloxazolidin-2-on-3-yl)-4(R)-(2'-methoxystyr-2-yl)azetidin-2-on-1-yl]acetic acid N-(3-trifluoromethylbenzyl)amide Example 231 was prepared using the procedure of Example 6, except that N-benzyloxycarbonyl-D-aspartic acid β-t-butyl ester monohydrate was replaced with Example 34, and 3-(trifluoromethyl)benzyl amine was replaced with 4-(piperidin-1-yl)piperidine; Example 231 exhibited an ¹H NMR spectrum consistent with the assigned structure.

Example 232-233, shown in Table 15, were prepared using the procedure of Example 6, except that N-benzyloxycarbonyl-D-aspartic acid β-t-butyl ester monohydrate was replaced with Example 34H, and 3-(trifluoromethyl)benzyl amine was replaced with the appropriate amine; all listed Examples exhibited an ¹H NMR spectrum consistent with the assigned structure.

TABLE 15

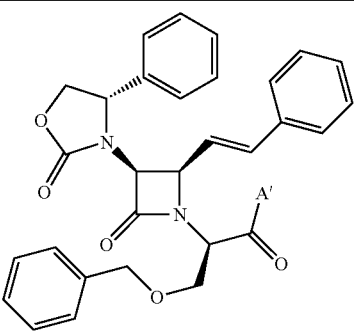

| Example | A' |
|---|---|
| 232 | 4-(piperidin-1-yl)piperidin-1-yl |
| 233 | 4-[2-(piperidin-1-yl)ethyl]piperidin-1-yl |

EXAMPLE 234

(2RS)-[4-(piperidin-1-yl)piperidin-1-ylcarbonyl]-2-methyl-2-[3(S)-(4(S)-phenyloxazolin-2-on-3-yl)-4(R)-(2-styryl)azetidin-2-on-1-yl]acetic acid N-(3-trifluoromethylbenzyl)amide

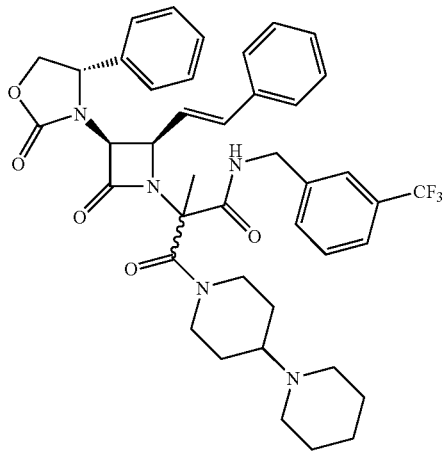

Example 37 (50 mg, 0.067 mmol) in tetrahydrofuran (4 mL) was treated sequentially with sodium hydride (4 mg, 0.168 mmol) and methyl iodide (6 μL, 0.094 mmol) at −78° C. The resulting mixture was slowly warmed to ambient temperature, and evaporated. The resulting residue was partitioned between dichloromethane and water, and the organic layer was evaporated. The resulting residue was purified by silica gel chromatography (95:5 chloroform/methanol) to give 28 mg (55%) of the title compound as an off-white solid; MS (ES$^+$): m/z=757 (M$^+$).

EXAMPLE 235

2(S)-[[(1-Benzylpiperidin-4-yl)amino]carbonylmethyl]-2-[3(S)-(4(S)-phenyloxazolidin-2-on-3-yl)-4(R)-(2-phenyleth-1-yl)azetidin-2-on-1-yl]acetic acid N-(3-trifluoromethylbenzyl)amide Example 235 was prepared using the procedure of Example 8, except that N-benzyloxycarbonyl-L-aspartic acid β-t-butyl ester α-(3-trifluoromethyl)benzylamide was replaced with Example 63 (50 mg, 0.064 mmol) to give 40 mg (80%) of Example 235 as an off-white solid; Example 235 exhibited an $^1$H NMR spectrum consistent with the assigned structure.

EXAMPLE 235

(2S)-[(4-cyclohexylpiperazin-1-yl)carbonylethyl]-2-[3(S)-(4(S)-phenyloxazolidin-2-on-3-yl)-4(R)-(2-phenyleth-1-yl)azetidin-2-on-1-yl]acetic acid N-(3-trifluoromethylbenzyl)amide Example 236 was prepared using the procedure of Example 8, except that N-benzyloxycarbonyl-L-aspartic acid β-t-butyl ester α-(3-trifluoromethyl)benzylamide was replaced with Example 110 (50 mg, 0.065 mmol) to give 42 mg (84%) of Example 236 as an off-white solid; Example 236 exhibited an $^1$H NMR spectrum consistent with the assigned structure.

Table 16 illustrates compounds further characterized by mass spectral analysis using FAB$^+$ to observe the corresponding (M+H)$^+$ parent ion.

TABLE 16

| Example | (m + H)$^+$/z |
|---|---|
| 37 | 744 |
| 38 | 766 |
| 39 | 766 |
| 40 | 718 |
| 41 | 704 |
| 42 | 744 |
| 42A | 772 |
| 44 | 758 |
| 63 | 780 |
| 85 | 766 |
| 86A | 786 |
| 88 | 772 |
| 91 | 759 |
| 95 | 780 |
| 96 | 824 |
| 104 | 732 |
| 110 | 772 |
| 111 | 800 |
| 112 | 803 |
| 120 | 786 |
| 120A | 800 |
| 120B | 732 |
| 133 | 758 |
| 134A | 786 |
| 134C | 780 |
| 136 | 794 |
| 137 | 746 |
| 138 | 732 |
| 139 | 772 |
| 174 | 772 |
| 175 | 772 |
| 176 | 772 |
| 177 | 790 |
| 179 | 790 |
| 180 | 790 |
| 182 | 772 |
| 183 | 734 |
| 184 | 722 |
| 185 | 740 |
| 186 | 756 |
| 187 | 738 |
| 188 | 840 |
| 189 | 749 |
| 190 | 782 |
| 191 | 704 |
| 192 | 718 |
| 193 | 718 |
| 199 | 732 |
| 200 | 718 |
| 201 | 764 |
| 202 | 748 |
| 203 | 748 |
| 205 | 786 |
| 206 | 718 |
| 207 | 730 |
| 208 | 705 |
| 209 | 705 |
| 210 | 705 |
| 211 | 694 |
| 212 | 708 |
| 213 | 710 |
| 214 | 744 |
| 215 | 744 |
| 216 | 7530 |
| 217 | 758 |
| 218 | 792 |
| 219 | 764 |
| 220 | 734 |
| 221 | 746 |
| 222 | 776 |
| 224 | 704 |
| 225 | 772 |
| 226 | 806 |

TABLE 16-continued

| Example | (m + H)+/z |
|---|---|
| 227 | 792 |
| 228 | 752 |
| 229 | 780 |
| 230 | 766 |
| 231 | 788 |
| 232 | 663 |
| 233 | 691 |
| 234 | 758 |
| 235 | 782 |
| 236 | 774 |

Method Example 1

Human Vasopression $V_{1a}$ Receptor Binding Assay.

A cell line expressing the human $V_{1a}$ receptor in CHO cells (henceforth referred to as the $hV_{1a}$ cell line) was obtained from Dr. Michael Brownstein, NIMH, Bethesda, Md., USA. The $hV_{1a}$ cDNA sequence is described by Thibonnier et al., *Journal of Biological Chemistry*, 269, 3304-3310 (1994), and the expression method was the same as described by Morel et al. (1992). The $hV_{1a}$ cell line was grown in alpha-MEM with 10% fetal bovine serum and 250 ug/ml G418 (Gibco, Grand Island, N.Y., USA). For competitive binding assay, hV1a cells were plated into 6-well culture plate at 1:10 dilution from a confluency flask, and maintained in culture for at least two days. Culture medium was then removed, cells were washed with 2 ml binding buffer (25 mM Hepes, 0.25% BSA, 1×DMEM, PH=7.0). To each well, 990 µl binding buffer containing 1 nM 3H-AVP was added, and followed by 10 µl series diluted Example compounds dissolved in DMSO. All incubations were in triplicate, and dose-inhibition curves consisted of total binding (DMSO) and 5 concentrations (0.1, 1.0, 10, 100, and 1000 nM) of test agents encompassing the $IC_{50}$. 100 nM cold AVP (Sigma) was used to assess non-specific binding. Cells were incubated for 45 minutes at 37° C., assay mixture was removed and each well was washed three times with PBS (pH=7.4). 1 ml 2% SDS was added per well and plates were let sit for 30 minutes. The whole content in a well was transferred to a scintillation vial. Each well was rinsed with 0.5 ml PBS which was then added to the corresponding vial. Scintillation fluid (Ecoscint, National Diagnostics, Atlanta, Ga.) was then added at 3 ml per vial. Samples were counted in a liquid scintillation counter (Beckman LS3801). $IC_{50}$ values were calculated by Prism Curve fitting software.

All of the alkanedioic esters and amides exemplified in the foregoing examples were tested in this assay described of Example 201. Binding affinities for certain of the preferred compounds are summarized in the Table 17.

TABLE 17

| Example | $V_{1a}$ BINDING AFFINITY ($IC_{50}$ (nM)) |
|---|---|
| 18 | 35 |
| 19 | 35 |
| 20 | 35 |
| 35 | 1.9 |
| 37 | 5.5 |
| 38 | <25 |
| 39 | 23 |
| 40 | 11 |
| 41 | <20 |

TABLE 17-continued

| Example | $V_{1a}$ BINDING AFFINITY ($IC_{50}$ (nM)) |
|---|---|
| 42 | <20 |
| 44 | 3.1 |
| 47 | ~50 |
| 59 | <100 |
| 63 | 1.84 |
| 66 | ~50 |
| 77 | <100 |
| 78 | <100 |
| 81 | <100 |
| 82 | <50 |
| 85 | 5.87 |
| 87 | 15 |
| 88 | 2.4 |
| 91 | 3.24 |
| 95 | 1.76 |
| 96 | 4.35 |
| 100 | <100 |
| 101 | ~100 |
| 102 | <100 |
| 103 | 0.81 |
| 104 | 1.85 |
| 106 | ~100 |
| 107 | <50 |
| 108 | ~100 |
| 109 | ~100 |
| 110 | 0.49 |
| 111 | 1.31 |
| 112 | 1.34 |
| 120 | 0.75 |
| 133 | 2.43 |
| 135 | ~50 |
| 136 | 11 |
| 137 | 17 |
| 138 | 21 |
| 139 | 9.5 |

Method Example 2

Inhibition of Phosphatidylinositol Turnover.

The physiological effects of vasopressin are mediated through specific G-protein coupled receptors. The vasopressin $V_{1a}$ receptor is coupled to the $G_q/G_{11}$ family of G proteins and mediates phosphatidylinositol turnover. The agonist or antagonist character of the compounds of the invention may be determined by their ability to inhibit vasopressin-mediated turnover of phosphatidylinositol by the procedure described in the following paragraphs. Representative compounds of the invention, the compounds of Examples 35, 44, 88, 110, and 133, were tested in this assay and found to be vasopressin $V_{1a}$ antagonists.

Cell Culture and Labeling of Cells.

Three days prior to the assay, near-confluent cultures of hV1a cells were dissociated and seeded in 6-well tissue culture plates, about 100 wells being seeded from each 75 cm² flask (equivalent to 12:1 split ratio). Each well contained 1 mL of growth medium with 2 µCi of [³H]myo-inositol (American Radiolabeled Chemicals, St. Louis, Mo., USA).

Incubations

All assays were in triplicate except for basal and 10 nM AVP (both n=6). AVP ((arginine vasopressin), Peninsula Labs, Belmont, Calif., USA (#8103)) was dissolved in 0.1N acetic acid. Test agents were dissolved in DMSO and diluted in DMSO to 200 times the final test concentration. Test agents and AVP (or corresponding volumes of DMSO) were added separately as 5 µL in DMSO to 12×75 mm glass tubes containing 1 mL of assay buffer (Tyrode's balanced salt solution containing 50 mM glucose, 10 mM LiCl, 15 mM HEPES pH 7.4, 10 µM phosphoramidon, and 100 µM bacitracin). The order of incubations was randomized. Incubations were initiated by removing the prelabeling medium, washing the monolayer once with 1 mL of 0.9% NaCl, and transferring the contents of the assay tubes to corresponding wells. The plates were incubated for 1 hour at 37° C. Incubations were terminated by removing the incubation medium and adding 500 µL of ice cold 0.5% (w/v) trichloroacetic acid and allowing the wells to stand for 15 min.

Measurement of [$^3$H]Inositol Phosphates

BioRad Poly-Prep Econo-Columns were packed with 0.3 mL of AG 1 X-8 100-200 formate form resin. Resin was mixed 1:1 with water and 0.6 mL added to each column. Columns were then washed with 10 mL water. Scintillation vials (20 mL) were placed under each column. For each well, the contents were transferred to a minicolumn, after which the well was washed with 0.5 mL distilled water, which was also added to the minicolumn. The columns were then washed twice with 5 mL of 5 mM myo-inositol to elute free inositol. Aliquots (1 mL) were transferred to 20 mL scintillation vials and 10 mL of Beckman Ready Protein Plus added. After the myo-inositol wash was complete, empty scintillation vials were placed under the columns, and [$^3$H] inositol phosphates were eluted with three additions of 1 mL 0.5 M ammonium formate containing 0.1 N formic acid. Elution conditions were optimized to recover inositol mono-, bis-, and trisphosphates, without eluting the more metabolically inert tetrakis-, pentakis-, and hexakis-phosphates. To each sample was added 10 mL of a high salt capacity scintillation fluid such as Tru-Count High Salt Capacity or Packard Hionic-Fluor. Inositol lipids were measured by adding 1 mL of 2% sodium dodecyl sulfate (SDS) to each well, allowing the wells to stand for at least 30 min., and transferring the solution to 20 mL scintillation vials, to which 10 mL Beckman Ready Protein Plus scintillation fluid was then added. Samples were counted in a Beckman LS 3801 liquid scintillation counter for 10 min. Total inositol incorporation for each well was calculated as the sum of free inositol, inositol phosphates, and inositol lipids.

Data Analysis: Concentration-Inhibition Experiments

Concentration-response curves for AVP and concentration-inhibition curves for test agents versus 10 nM AVP were analyzed by nonlinear least-squares curve-fitting to a 4-parameter logistic function. Parameters for basal and maximal inositol phosphates, $EC_{50}$ or $IC_{50}$, and Hill coefficient were varied to achieve the best fit. The curve-fitting was weighted under the assumption that the standard deviation was proportional to dpm of radioactivity. Full concentration-response curves for AVP were run in each experiment, and $IC_{50}$ values were converted to $K_i$ values by application of the Cheng-Prusoff equation, based on the $EC_{50}$ for AVP in the same experiment. Inositol phosphates were expressed as dpm per $10^6$ dpm of total inositol incorporation.

Data Analysis: Competitivity Experiments

Experiments to test for competitivity of test agents consisted of concentration-response curves for AVP in the absence and presence of two or more concentrations of test agent. Data were fit to a competitive logistic equation $$Y = B + \frac{M \times \{A/[E+(D/K)]\}^Q}{1+\{A/[E+(D/K)]\}^Q}$$

where Y is dpm of inositol phosphates, B is concentration of basal inositol phosphates, M is the maximal increase in concentration of inositol phosphates, A is the concentration of agonist (AVP), E is the $EC_{50}$ for agonist, D is the concentration of antagonist (test agent), K is the $K_i$ for antagonist, and Q is the cooperativity (Hill coefficient).

Vasopressin $V_{1a}$ receptors are also known to mediate platelet aggregation. Vasopressin $V_{1a}$ receptor agonists cause platelet aggregation, while vasopressin $V_{1a}$ receptor antagonists inhibit the platelet aggregation precipitated by vasopressin or vasopressin $V_{1a}$ agonists. The degree of antagonist activity of the compounds of the invention may be determined by the assay described in the following paragraphs.

Blood from healthy, human volunteers was collected by venipuncture and mixed with heparin (60 mL of blood added to 0.4 mL of heparanized saline solution (4 mg heparin/mL saline)). Platelet-rich plasma (PRP) was prepared by centrifuging whole blood (150×g), and indomethacin (3 µM) was added to PRP to block the thromboxane-mediated release reaction. PRP was continuously stirred at 37° C. and change in optical density was followed after the addition of arginine vasopressin (AVP) (30 nM) to initiate aggregation. Compounds were dissolved in 50% dimethylsulfoxide (DMSO) and added (10 µL/415 µL PRP) before the addition of AVP. The percent inhibition of AVP-induced aggregation was measured and an $IC_{50}$ calculated.

In studies using washed platelets, 50 mL of whole blood was mixed with 10 mL of citrate/heparin solution (85 mM sodium citrate, 64 mM citric acid, 111 mM glucose, 5 units/mL heparin) and PRP isolated as described above. PRP was then centrifuged (150×g) and the pellet resuspended in a physiologic buffer solution (10 mM HEPES, 135 mM sodium chloride, 5 mM potassium chloride, and 1 mM magnesium chloride) containing 10 µM indomethicin. Human fibrinogen (0.2 mg/mL) and calcium chloride (1 mM) were added to stirred platelets before initiating aggregation with AVP (30 nM) as previously described.

The activity of compounds of formula I in the antagonism of the vasopressin $V_{1a}$ receptor provides a method of antagonizing the vasopressin $V_{1a}$ receptor comprising administering to a subject in need of such treatment an effective amount of a compound of that formula. It is known that numerous physiological and therapeutic, benefits are obtained through the administration of drugs that antagonize the vasopressin $V_{1a}$ receptor. These activities may be catagorized as peripheral and central. Peripheral utilities include administration of vasopressin $V_{1a}$ antagonists of formula I as adjuncts in heart failure or as antithrombotic agents. Central effects include administration of vasopressin $V_{1a}$ antagonists of formula I in the treatment of obsessive-compulsive disorder, aggressive disorders, depression and anxiety.

Obsessive-compulsive disease appears in a great variety of degrees and symptoms, generally linked by the victim's uncontrollable urge to perform needless, ritualistic acts. Acts of acquiring, ordering, cleansing and the like, beyond any rational need or rationale, are the outward characteristic of the disease. A badly afflicted subject may be unable to do anything but carry out the rituals required by the disease. Obsessive-compulsive disease, in all its variations, is a preferred target of treatment with the present adjunctive therapy method and compositions. The utility of the compounds of Formula I in the treatment of obsessive-compulsive disorder was demonstrated as described in the following assay.

In golden hamsters, a particular stereotypy; flank marking behavior, can be induced by microinjections of vasopressin (10-100 nL, 1-100 µM) into the anterior hypothalamus (Ferris et al., *Science*, 224, 521-523 (1984); Albers and Ferris, *Regulatory Peptides*, 12, 257-260 (1985); Ferris et al., *European Journal of Pharmacology*, 154, 153-159 (1988)). Following the releasing stimulus, the behavior is initiated by grooming, licking and combing of the large sebaceous glands on the dorsolateral flanks. Bouts of flank gland grooming may be so intense that the flank region is left matted and soaked in saliva. After grooming, the hamsters display flank marking behavior, a type of scent marking involved in olfactory communication (Johnston, *Physio. Behav.*, 51, 437-448 (1985); Ferris et al., *Physio. Behav.*, 40, 661-664 (1987)), by arching the back and rubbing the flank glands vigorously against any vertical surface. Vasopressin-induced flank marking is usually induced within a minute after the microinjection (Ferris et al., *Science*, 224, 521-523 (1984)). The behavior is specific to vasopressin, as microinjections of other neuropeptides, excitatory amino acids, and catecholamines do not elicit flank marking (Ferris et al., *Science*, 224, 521-523 (1984); Albers and Ferris, *Regulatory Peptides*, 12, 257-260 (1985)). Furthermore, flank marking is specific to the vasopressin $V_1$ receptor, as the behavior is selectively inhibited by $V_1$ receptor antagonists and activated by $V_1$ receptor agonists (Ferris et al. *Neuroscience Letters*, 55, 239-243 (1985); Albers et al., *Journal of Neuroscience*, 6, 2085-2089 (1986); Ferris et al., *European Journal of Pharmacology*, 154, 153-159 (1988)).

All animals were adult male golden hamsters (*Mesocricetus auratus*) weighing approximately 160 gm. The animals underwent stereotaxic surgery, and were allowed to recover before behavioral testing. The hamsters were kept on a reverse light cycle (14 hr-light, 10 hr dark, lights on at 19:00) in Plexiglas™ cages, and received food and water ad libitum.

Stereotaxic surgery was performed under pentobarbital anesthesia. The stereotaxic coordinates were: 1.1 mm anterior to the bregma, 1.8 mm lateral to the midsagittal suture at an 8° angle from the verticle line, and 4.5 mm below the dura. The nose bar was placed at the level of the interaural line. An unilateral 26-gauge guide cannula was lowered to the site and secured to the skull with dental cement. The guide cannulae were closed with a 33-gauge obturator extending 1 mm beyond the guide. The innercanulae used for the microinjections extended 3.0 mm beyond the guide to reach the anterior hypothalamus.

The hamsters were microinjected with 1 µM vasopressin in a volume of 150 nL. The vasopressin was given as a cocktail with 200 mM, 20 mM, 2 mM of the test compound or alone, in the vehicle, dimethylsulfoxide. Both the vasopressin and the test compound were dissolved in 100% dimethylsulfoxide. All injections were aimed at the anterior hypothalamus. Animals were scored for flank marking for a period of 10 minutes in a clean cage.

Another aspect of this invention is the use of compounds of formula I in combination with a serotonin reuptake inhibitor for use in the treatment of obsessive-compulsive disease, aggressive disorder, or depression. Compounds useful as serotonin reuptake inhibitors include but are not limited to:

Fluoxetine, N-methyl-3-(p-trifluoromethylphenoxy)-3-phenylpropylamine, is marketed in the hydrochloride salt form, and as the racemic mixture of its two enantiomers. U.S. Pat. No. 4,314,081 is an early reference on the compound. Robertson et al., *J. Med. Chem.*, 31, 1412 (1988), taught the separation of the R and S enantiomers of fluoxetine and showed that their activity as serotonin uptake inhibitors is similar to each other. In this document, the word "fluoxetine" will be used to mean any acid addition salt or the free base, and to include either the racemic mixture or either of the R and S enantiomers;

Duloxetine, N-methyl-3-(1-naphthalenyloxy)-3-(2-thienyl)propanamine, is usually administered as the hydrochloride salt and as the (+) enantiomer. It was first taught by U.S. Pat. No. 4,956,388, which shows its high potency. The word "duloxetine" will be used here to refer to any acid addition salt or the free base of the molecule;

Venlafaxine is known in the literature, and its method of synthesis and its activity as an inhibitor of serotonin and norepinephrine uptake are taught by U.S. Pat. No. 4,761,501. Venlafaxine is identified as compound A in that patent;

Milnacipran (N,N-diethyl-2-aminomethyl-1-phenylcyclopropanecarboxamide) is taught by U.S. Pat. No. 4,478,836, which prepared milnacipran as its Example 4. The patent describes its compounds as antidepressants. Moret et al., *Neuropharmacology*, 24, 1211-19 (1985), describe its pharmacological activities as an inhibitor of serotonin and norepinephrine reuptake;

Citalopram, 1-[3-(dimethylamino)propyl]-1-(4-fluorophenyl)-1,3-dihydro-5-isobenzofurancarbonitrile, is disclosed in U.S. Pat. No. 4,136,193 as a serotonin reuptake inhibitor. Its pharmacology was disclosed by Christensen et al., *Eur. J. Pharmacol.*, 41, 153 (1977), and reports of its clinical effectiveness in depression may be found in Dufour et al., *Int. Clin. Psychopharmacol.*, 2, 225 (1987), and Timmermnan et al., ibid., 239;

Fluvoxamine, 5-methoxy-1-[4-(trifluoromethyl)phenyl]-1-pentanone O-(2-aminoethyl)oxime, is taught by U.S. Pat. No. 4,085,225. Scientific articles about the drug have been published by Claassen et al., *Brit. J. Pharmacol.*, 60, 505 (1977); and De Wilde et al., *J. Affective Disord.*, 4, 249 (1982); and Benfield et al., *Drugs*, 32, 313 (1986);

Paroxetine, trans-(−)-3-[(1,3-benzodioxol-5-yloxy)methyl]-4-(4-fluorophenyl)piperidine, may be found in U.S. Pat. Nos. 3,912,743 and 4,007,196. Reports of the drug's activity are in Lassen, *Eur. J. Pharmacol.*, 47, 351 (1978); Hassan et al., *Brit. J. Clin. Pharmacol.*, 19, 705 (1985); Laursen et al., *Acta Psychiat. Scand.*, 71, 249 (1985); and Battegay et al., *Neuropsychobiology*, 13, 31 (1985); and Sertraline, (1S-cis)-4-(3,4-dichlorophenyl)-1,2,3,4-tetrahydro-N-methyl-1-naphthylamine hydrochloride, a serotonin reuptake inhibitor disclosed in U.S. Pat. No. 4,536,518, is marketed as an antidepressant.

All of the above-referenced patents are hereby incorporated by reference.

The adjunctive therapy of this aspect of the present invention is carried out by administering a vasopressin $V_{1a}$ antagonist together with a serotonin reuptake inhibitor in any manner that provides effective levels of the compounds in the body at the same time. All of the compounds concerned are orally available and are normally administered orally, and so oral administration of the adjunctive combination is preferred. They may be administered together, in a single dosage form, or may be administered separately.

This aspect of the present invention provides a potentiation of the decrease in the concentration of vasopressin observed as an effect of administration of a vasopressin $V_{1a}$ antagonist by administration of a serotonin reuptake inhibitor. This aspect of the present invention is particularly suited for use in the treatment of depression and obsessive compulsive disorder. Such disorders may often be resistant to treatment with a serotonin reuptake inhibitor alone.

Method Example 3

Human Oxytocin Binding and Functional Assay.

Compounds of the present invention are believed to be oxytocin agents. Oxytocin preparations and a number of oxytocin agonists are commercially available for therapeutic use. In recent years, oxytocin antagonists with antiuterotonic activity have been developed and evaluated for their potential use in the treatment of preterm labor and dysmenorrhyea (Pavo et al., *J. Med. Chem.*, 37, 255-259 (1994); Akerlund et al., *Br. J. Obstet. Gynaecol.*, 94, 1040-1044 (1987); Akerlund et al., *Br. J. Obstet. Gynaecol.*, 86, 484-487 (1979)). The oxytocin antagonist atosiban has been studied clinically and resulted in a more significant inhibition of preterm contractions than did placebo (Goodwin et al., *Am. J. Obstet. Gynecol.*, 170, 474 (1994)).

The human oxytocin receptor has been cloned and expressed (Kimura et al., *Nature*, 356, 526-529 (1992)), it is identified under the accession number X64878. To demonstrate the affinity of the compounds of the present invention for the human oxytocin receptor, binding studies were performed using a cell line expressing the human oxytocin receptor in 293 cells (henceforth referred to as the OTR cell line) substantially by the procedure described by Morel et al. (*Nature*, 356, 523-526 (1992)). The 293 cell line is a permanent line of primary human embryonal kidney cells transformed by sheared human adenovirus type 5 DNA. It is identified as ATCC CRL-1533.

The OTR cell line was grown in DMEM (Delbecco's Modified Essential Medium, Sigma, St. Louis, Mo., USA) with 10% fetal bovine serum, 2 mM L-glutamine, 200 µg hygromycin (Sigma, St. Louis, Mo., USA) and 250 µg/ml G418 (Gibco, Grand Island, N.Y., USA). To prepare membranes, OTR cells were grown to confluency in 20 roller bottles. Cells were dissociated with enzyme-free cell dissociation medium (Specialty Media, Lavallette, N.J., USA) and centrifuged at 3200 rpm for 15 minutes. The pellet was resuspended in 40 mL of Tris-HCl (tris[hydroxymethyl] aminomethane hydro-chloride) buffer (50 mM, pH 7.4) and homogenized for 1 minute with a Tekmar Tissumizer (Cincinnatti, Ohio USA). The suspension was centrifuged at 40,000×g for 10 minutes. The pellet was resuspended and centrifuged as above. The final pellet was suspended in 80 mL of Tris 7.4 buffer and stored in 4 mL aliquots at −80° C. For assay, aliquots were resuspended in assay buffer and diluted to 375 µg protein per mL. Protein concentration was determined by BCA assay (Pierce, Rockford, Ill., USA).

Assay buffer was 50 mM Tris-HCl (tris[hydroxymethyl] aminomethane hydrochloride), 5 mM $MgCl_2$, and 0.1% bovine serum albumin at pH 7.4. The radioligand for binding assays was [$^3$H]oxytocin ([tyrosyl-2,6-$^3$H]oxytocin, 48.5 Ci/mmol, DuPont NEN, Boston, Mass., USA). The order of additions was 195 µL assay buffer, 200 µL OTR membranes (75 µg protein) in assay buffer, 5 µL of test agent in dimethylsulfoxide (DMSO) or DMSO alone, and 100 µL [$^3$H]oxytocin in assay buffer (final concentration 1.0 nM). Incubations were for one hour at room temperature. Bound radioligand was separated from free by filtration on a Brandel cell harvester (Gaithersburg, Md., USA) through Whatman GF/B glass-fiber filters that had been soaked for 2 hours in 0.3% polyethylenimine. The filters were washed with ice-cold 50 mM Tris-HCl (pH 7.7 at 25° C.) and the filter circles were placed in scintillation vials, to which were then added 5 mL Ready Protein Plus™ scintillation fluid, and counted in a liquid scintillation counter. All incubations were in triplicate, and dose-inhibition curves consisted of total binding, nonspecific binding (100 µM oxytocin, Sigma, St. Louis, Mo., USA), and 6 or 7 concentrations of test agent encompassing the $IC_{50}$. Total binding was typically about 1,000 cpm and nonspecific binding about 200 cpm. $IC_{50}$ values were calculated by nonlinear least-squares curve-fitting to a 4-parameter logistic model. Certain compounds of formula I have shown affinity for the oxytocin receptor.

Several bioassays are available to determine the agonist or antagonist character of compounds exhibiting affinity at the oxytocin receptor. One such assay is described in U.S. Pat. No. 5,373,089, hereby incorporated by reference. Said bioassay is derived from procedures described in a paper by Sawyer et al. (*Endocrinology*, 106, 81 (1980)), which in turn was based on a report of Holton (*Brit. J. Pharmacol.*, 3, 328 (1948)). The assay calculations for $pA_2$ estimates are described by Schild (*Brit. J. Pharmacol.*, 2, 189 (1947)).

Assay Method

1. Animals—a 1.5 cm piece of uterus from a virgin rat (Holtzman) in natural estrus is used for the assay.

2. Buffer/Assay Bath—The buffer used is Munsicks. This buffer contains 0.5 mM $Mg^{2+}$. The buffer is gassed continuously with 95% oxygen/5% carbon dioxide giving a pH of 7.4. The temperature of the assay bath is 37° C. A 10 mL assay bath is used that contains a water jacket for maintaining the temperature and inlet and outlet spikets for adding and removing buffer.

3. Polygraph/transducer—The piece of uterine tissue used for the assay is anchored at one end and connected to a Statham Strain Gauge Force Transducer at the other end which in turn is attached to a Grass Polygraph Model 79 for monitoring the contractions.

4. Assay Protocol:

(a) The tissue is equilibrated in the assay bath for one hour with washing with new buffer every 15 minutes. One gram of tension is kept on the tissue at all times.

(b) The tissue is stimulated initially with oxytocin at 10 nM to acclimate the tissue and with 4 mM potassium chloride (KCl) to determine the maximum contractile response.

(c) A cumulative dose response curve is then done with oxytocin and a concentration of oxytocin equivalent to approximately 80% of the maximum is used for estimating the $pA_2$ of the antagonist.

(d) The tissue is exposed to oxytocin (Calbiochemical, San Diego, Calif.) for one minute and washed out. There is a three minute interval before addition of the next dose of agonist or antagonist. When the antagonist is tested, it is given five minutes before the agonist. The agonist is given for one minute. All responses are integrated using a 7P10 Grass Integrator. A single concentration of oxytocin, equal to 80% of the maximum response, is used to test the antagonist. Three different concentrations of antagonists are used, two that will reduce the response to the agonist by less than 50% and one that will reduce the response greater than 50% (ideally this relation would be 25%, 50% and 75%). This is repeated three times for each dose of antagonist for a three point assay.

(e) Calculations for $pA_2$—The dose-response (DR) ratios are calculated for antagonist and a Schild's Plot is performed by plotting the Log (DR−1) vs. Log of antagonist concentration. The line plotted is calculated by least-squares regression analysis. The $pA_2$ is the concentration of antagonist at the point where the regression line crosses the 0 point of the Log (DR−1) ordinate. The $pA_2$ is the negative Log of the concentration of antagonist that will reduce the response to the agonist by one-half.

Oxytocin is well known for its hormonal role in parturition and lactation. Oxytocin agonists are useful clinically to induce lactation; induce or augment labor; control postpartum uterine atony and hemmorhage; cause uterine contraction after cesarean section or during other uterine surgery; and to induce therapeutic abortion. Oxytocin, acting as a neurotransmitter in the central nervous system, also plays an important role in the expression of central functions such as maternal behavior, sexual behavior (including penile erection, lordosis and copulatory behavior), yawning, tolerance and dependance mechanisms, feeding, grooming, cardiovascular regulation and thermoregulation (Argiolas and Gessa, *Neuroscience and Biobehavioral Reviews*, 15, 217-231 (1991)). Oxytocin antagonists find therapeutic utility as agents for the delay or prevention of premature labor; or to slow or arrest delivery for brief periods in order to undertake other therapeutic measures.

Method Example 4

Tachykinin Receptor Binding Assay

Compounds of the present invention are believed to be tachykinin agents. Tachykinins are a family of peptides which share a common amidated carboxy terminal sequence. Substance P was the first peptide of this family to be isolated, although its purification and the determination of its primary sequence did not occur until the early 1970's. Between 1983 and 1984 several groups reported the isolation of two novel mammalian tachykinins, now termed neurokinin A (also known as substance K, neuromedin L, and neurokinin α), and neurokinin B (also known as neuromedin K and neurokinin β). See, J. E. Maggio, *Peptides*, 6 (Supplement 3), 237-243 (1985) for a review of these discoveries.

Tachykinins are widely distributed in both the central and peripheral nervous systems. When released from nerves, they exert a variety of biological actions, which, in most cases, depend upon activation of specific receptors expressed on the membrane of target cells. Tachykinins are also produced by a number of non-neural tissues. The mammalian tachykinins substance P, neurokinin A, and neurokinin B act through three major receptor subtypes, denoted as NK-1, NK-2, and NK-3, respectively. These receptors are present in a variety of organs.

Substance P is believed inter alia to be involved in the neurotransmission of pain sensations, including the pain associated with migraine headaches and with arthritis. These peptides have also been implicated in gastrointestinal disorders and diseases of the gastrointestinal tract such as inflammatory bowel disease. Tachykinins have also been implicated as playing a role in numerous other maladies, as discussed infra.

In view of the wide number of clinical maladies associated with an excess of tachykinins, the development of tachykinin receptor antagonists will serve to control these clinical conditions. The earliest tachykinin receptor antagonists were peptide derivatives. These antagonists proved to be of limited pharmaceutical utility because of their metabolic instability. Recent publications have described novel classes of non-peptidyl tachykinin receptor antagonists which generally have greater oral bioavailability and metabolic stability than the earlier classes of tachykinin receptor antagonists. Examples of such newer non-peptidyl tachykinin receptor antagonists are found in European Patent Publication 591,040 A1, published Apr. 6, 1994; Patent Cooperation Treaty publication WO 94/01402, published Jan. 20, 1994; Patent Cooperation Treaty publication WO 94/04494, published Mar. 3, 1994; Patent Cooperation Treaty publication WO 93/011609, published Jan. 21, 1993, Patent Cooperation Treaty publication WO 94/26735, published Nov. 24, 1994. Assays useful for evaluating tachykinin receptor antagonists are well known in the art. See, e.g., J. Jukic et al., *Life Sciences*, 49, 1463-1469 (1991); N. Kucharczyk et al., *Journal of Medicinal Chemistry*, 36, 1654-1661 (1993); N. Rouissi et al., *Biochemical and Biophysical Research Communications*, 176, 894-901 (1991).

Method Example 5

NK-1 Receptor Binding Assay

Radioreceptor binding assays were performed using a derivative of a previously published protocol. D. G. Payan et al., *Journal of immunology*, 133,3260-3265 (1984). In this assay an aliquot of IM9 cells ($1\times10^6$ cells/tube in RPMI 1604 medium supplemented with 10% fetal calf serum) was incubated with 20 pM $^{125}$I-labeled substance P in the presence of increasing competitor concentrations for 45 minutes at 4° C.

The IM9 cell line is a well-characterized cell line which is readily available to the public. See, e.g., *Annals of the New York Academy of Science*, 190, 221-234 (1972); *Nature (London)*, 251,443-444 (1974); *Proceedings of the National Academy of Sciences (USA)*, 71, 84-88 (1974). These cells were routinely cultured in RPMI 1640 supplemented with 50 µg/mL gentamicin sulfate and 10% fetal calf serum.

The reaction was terminated by filtration through a glass fiber filter harvesting system using filters previously soaked for 20 minutes in 0.1% polyethylenimine. Specific binding of labeled substance P was determined in the presence of 20 nM unlabeled ligand.

Method Example 6

NK-2 Receptor Binding Assay

The CHO-hNK-2R cells, a CHO-derived cell line transformed with the human NK-2 receptor, expressing about 400,000 such receptors per cell, were grown in 75 $cm^2$ flasks or roller bottles in minimal essential medium (alpha modification) with 10% fetal bovine serum. The gene sequence of the human NK-2 receptor is given in N. P. Gerard et al., *Journal of Biological Chemistry*, 265, 20455-20462 (1990).

For preparation of membranes, 30 confluent roller bottle cultures were dissociated by washing each roller bottle with 10 ml of Dulbecco's phosphate buffered saline (PBS) without calcium and magnesium, followed by addition of 10 ml of enzyme-free cell dissociation solution (PBS-based, from Specialty Media, Inc.). After an additional 15 minutes, the dissociated cells were pooled and centrifuged at 1,000 RPM for 10 minutes in a clinical centrifuge. Membranes were prepared by homogenization of the cell pellets in 300 mL 50 mM Tris buffer, pH 7.4 with a Tekmar® homogenizer for 10-15 seconds, followed by centrifugation at 12,000 RPM (20,000×g) for 30 minutes using a Beckman JA-14® rotor. The pellets were washed once using the above procedure and the final pellets were resuspended in 100-120 mL 50 mM Tris buffer, pH 7.4, and 4 ml aliquots stored frozen at −70° C. The protein concentration of this preparation was 2 mg/mL.

For the receptor binding assay, one 4-mL aliquot of the CHO-hNK-2R membrane preparation was suspended in 40 mL of assay buffer containing 50 mM Tris, pH 7.4, 3 mM manganese chloride, 0.02% bovine serum albumin (BSA)

and 4 μg/mL chymostatin. A 200 μL volume of the homogenate (40 μg protein) was used per sample. The radioactive ligand was [$^{125}$I]iodohistidyl-neurokinin A (New England Nuclear, NEX-252), 2200 Ci/mmol. The ligand was prepared in assay buffer at 20 nCi per 100 μL; the final concentration in the assay was 20 pM. Non-specific binding was determined using 1 μM eledoisin. Ten concentrations of eledoisin from 0.1 to 1000 nM were used for a standard concentration-response curve.

All samples and standards were added to the incubation in 10 μL dimethylsulfoxide (DMSO) for screening (single dose) or in 5 μL DMSO for IC$_{50}$ determinations. The order of additions for incubation was 190 or 195 μL assay buffer, 200 μL homogenate, 10 or 5 μL sample in DMSO, 100 μL radioactive ligand. The samples were incubated 1 hr at room temperature and then filtered on a cell harvester through filters which had been presoaked for two hours in 50 mM Tris buffer, pH 7.7, containing 0.5% BSA. The filter was washed 3 times with approximately 3 mL of cold 50 mM. Tris buffer, pH 7.7. The filter circles were then punched into 12×75 mm polystyrene tubes and counted in a gamma counter.

Tachykinin receptor antagonists are of value in the treatment of a wide variety of clinical conditions which are characterized by the presence of an excess of tachykinin. These clinical conditions may include disorders of the central nervous system such as anxiety, depression, psychosis, and schizophrenia; neurodegenerative disorders such as dementia, including senile dementia of the Alzheimer's type, Alzheimer's disease, AIDS-associated dementia, and Down's syndrome; demyelinating diseases such as multiple sclerosis and amyotrophic lateral sclerosis and other neuropathological disorders such as peripheral neuropathy, such as diabetic and chemotherapy-induced neuropathy, and postherpetic and other neuralgias; acute and chronic obstructive airway diseases such as adult respiratory distress syndrome, bronchopneumonia, bronchospasm, chronic bronchitis, drivercough, and asthma; inflammatory diseases such as inflammatory bowel disease, psoriasis, fibrositis, osteoarthritis, and rheumatoid arthritis; disorders of the musculo-skeletal system, such as osteoporosis; allergies such as eczema and rhinitis; hypersensitivity disorders such as poison ivy; ophthalmic diseases such as conjunctivitis, vernal conjunctivitis, and the like; cutaneous diseases such as contact dermatitis, atopic dermatitis, urticaria, and other eczematoid dermatites; addiction disorders such as alcoholism; stress-related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal disorders or diseases associated with the neuronal control of viscera such as ulcerative colitis, Crohn's disease, emesis, and irritable bowel syndrome; disorders of bladder function such as bladder detrusor hyper-reflexia and incontinence; artherosclerosis; fibrosing and collagen diseases such as scleroderma and eosinophilic fascioliasis; irritative symptoms of benign prostatic hypertrophy; disorders of blood flow caused by vasodilation and vasospastic diseases such as angina, migraine, and Raynaud's disease; and pain or nociception, for example, that attributable to or associated with any of the foregoing conditions, especially the transmission of pain in migraine.

NK-1 antagonists are useful in the treatment of pain, especially chronic pain, such as neuropathic pain, post-operative pain, and migraines, pain associated with arthritis, cancer-associated pain, chronic lower back pain, cluster headaches, herpes neuralgia, phantom limb pain, central pain, dental pain, neuropathic pain, opioid-resistant pain, visceral pain, surgical pain, bone injury pain, pain during labor and delivery, pain resulting from burns, including sunburn, post partum pain, angina pain, and genitourinary tract-related pain including cystitis.

In addition to pain, NK-1 antagonists are especially useful in the treatment and prevention of urinary incontinence; irritative symptoms of benign prostatic hypertrophy; motility disorders of the gastrointestinal tract, such as irritable bowel syndrome; acute and chronic obstructive airway diseases, such as bronchospasm, bronchopneumonia, asthma, and adult respiratory distress syndrome; artherosclerosis; inflammatory conditions, such as inflammatory bowel disease, ulcerative colitis, Crohn's disease, rheumatoid arthritis, osteoarthritis, neurogenic inflammation, allergies, rhinitis, cough, dermatitis, urticaria, psoriasis, conjunctivitis, emesis, irritation-induced miosis; tissue transplant rejection; plasma extravasation resulting from cytokine chemotherapy and the like; spinal cord trauma; stroke; cerebral stroke (ischemia); Alzheimer's disease; Parkinson's disease; multiple sclerosis; amyotrophic lateral sclerosis; schizophrenia; anxiety; and depression.

NK-2 antagonists are useful in the treatment of urinary incontinence, bronchospasm, asthma, adult respiratory distress syndrome, motility disorders of the gastrointestinal tract, such as irritable bowel syndrome, and pain.

In addition to the above indications the compounds of the invention may be useful in the treatment of emesis, including acute, delayed, or anticipatory emesis, such as emesis induced by chemotherapy, radiation, toxins, pregnancy, vestibular disorders, motion, surgery, migraine, and variations in intercranial pressure. Most especially, the compounds of formula I are of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulfonates, and other compounds with an alkylating action, such as nitrosoureas, cisplatin, and dacarbazine; antimetabolites, for example, folic acid, purine, or pyrimidine antagonists; mitotic inhibitors, for example vinca alkaloids and derivatives of podophyllotoxin; and cytotoxic antibiotics.

Particular examples of chemotherapeutic agents are described, for instance, by D. J. Stewart in NAUSEA AND VOMITING: RECENT RESEARCH AND CLINICAL ADVANCES, (J. Kucharczyk et al., eds., 1991), at pages 177-203. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin, daunorubicin, procarbazine, mitomycin, cytarabine, etoposide, methotrexate, 5-fluorouracil, vinblastine, vincristine, bleomycin, and chlorambucil. R. J. Gralla et al., *Cancer Treatment Reports*, 68, 163-172 (1984).

The compounds of formula I may also be of use in the treatment of emesis induced by radiation, including radiation therapy such as in the treatment of cancer, or radiation sickness; and in the treatment of post-operaive nausea and vomiting.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., REMINGTON'S PHARMACEUTICAL SCIENCES, (16th ed. 1980).

In making the compositions employed in the present invention the active ingredient is usually mixed with an excipient, diluted by an excipient, or enclosed within such a carrier which can be in the form of a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1-0.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
| --- | --- |
| Compound of Example 35 | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Compound of Example 95 | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Compound of Example 63 | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| Compound of Example 103 | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |

| Ingredient | Quantity (mg/tablet) |
|---|---|
| Magnesium stearate | 0.5 mg |
| Talc | 1.0 mg |
| Total | 120 mg |

The active ingredient, starch, and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Compound of Example 104 | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6.

Suppositories, each containing 25 mg of active ingredient are made as follows:

| Ingredient | Amount |
|---|---|
| Compound of Example 110 | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
|---|---|
| Compound of Example 111 | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose, and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
|---|---|
| Compound of Example 112 | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9

An intravenous formulation may be prepared as follows:

| Ingredient | Quantity |
|---|---|
| Compound of Example 120 | 250.0 mg |
| Isotonic saline | 1000 ml |

Formulation Example 10

A topical formulation may be prepared as follows:

| Ingredient | Quantity |
|---|---|
| Compound of Example 35 | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

Sublingual or buccal tablets, each containing 10 mg of active ingredient, may be prepared as follows:

| Ingredient | Quantity Per Tablet |
| --- | --- |
| Compound of Example 95 | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the resulting solution is cooled to about 50-55° C. and the medicament is slowly admixed. The homogenous mixture is poured into forms made of an inert material to produce a drug-containing diffusion matrix having a thickness of about 2-4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions that can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

While the invention has been illustrated and described in detail in the foregoing description, such an illustration and description is to be considered as exemplary and not restrictive in character, it being understood that only the illustrative embodiments have been shown and described and that all changes and modifications that come within the spirit of the invention are desired to be protected.

What is claimed is:

1. A compound of the formula

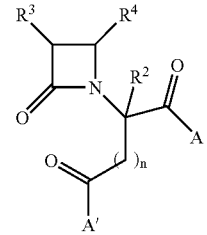

in a hydrate or solvate form, wherein:

n is an integer from 0 to 2;

A is XNH—, or $R^5XN$—;

A' is X'NH—, or $R^{5'}X'N$—;

$R^2$ is hydrogen or $C_1$-$C_6$ alkyl;

$R^3$ is a structure selected from the group consisting of

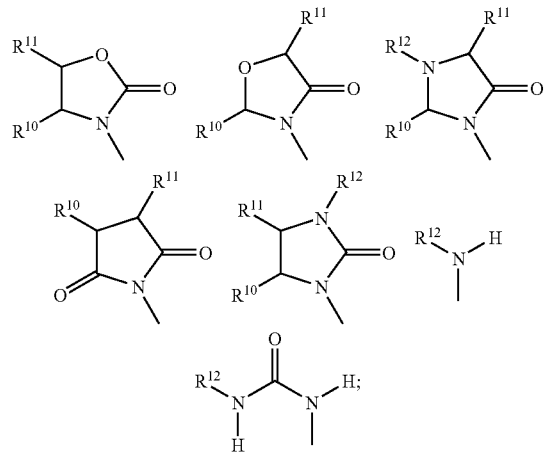

$R^4$ is $C_1$-$C_6$ alkyl, $C_2$-$C_6$ alkenyl, $C_2$-$C_6$ alkynyl, $C_3$-$C_8$ cycloalkyl, $C_3$-$C_9$ cycloalkenyl, limonenyl, pinenyl, $C_1$-$C_3$ alkanoyl, optionally-substituted aryl, optionally-substituted aryl($C_1$-$C_4$ alkyl), optionally-substituted aryl(halo $C_1$-$C_4$ alkyl), optionally-substituted aryl(alkoxy $C_1$-$C_4$ alkyl), optionally-substituted aryl($C_2$-$C_4$ alkenyl), optionally-substituted aryl(halo $C_2$-$C_4$ alkenyl), or optionally-substituted aryl($C_2$-$C_4$ alkynyl);

X is selected from the group consisting of $C_1$-$C_6$ alkyl, $C_3$-$C_8$ cycloalkyl, ($C_1$-$C_4$ alkoxy)-($C_1$-$C_4$ alkyl), optionally-substituted aryl, optionally-substituted aryl ($C_1$-$C_4$ alkyl), optionally-substituted aryl($C_3$-$C_7$ cycloalkyl), optionally-substituted indan-1-yl, optionally-substituted indan-2-yl, optionally-substituted 1,2,3,4-tetrahydronaphth-1-yl, optionally-substituted 1,2,3,4-tetrahydronaphth-2-yl, the heterocycle Y, Y—($C_1$-$C_4$ alkyl), $R^7R^8N$—, and $R^7R^8N$—($C_2$-$C_4$ alkyl); and $R^5$ is selected from the group consisting of hydroxy, $C_1$-$C_6$ alkyl, $C_1$-$C_4$ alkoxycarbonyl, and benzyl; or $R^5$ and X are taken together with the attached nitrogen atom to form an optionally substituted heterocycle selected from the group consisting of pyrrolidinyl, piperidinyl, piperazinyl, and homopiperazinyl, where said heterocycle is optionally substituted with $R^{10}$, $R^{12}$, $R^7R^8N$—, or $R^7R^8N$—($C_1$-$C_4$ alkyl);

X' is selected from the group consisting of $C_1$-$C_6$ alkyl, $C_3$-$C_8$ cycloalkyl, ($C_1$-$C_4$ alkoxy)-($C_1$-$C_4$ alkyl), optionally-substituted aryl, optionally-substituted aryl ($C_1$-$C_4$ alkyl), optionally-substituted aryl($C_3$-$C_7$ cycloalkyl), optionally-substituted indan-1-yl, optionally-substituted indan-2-yl, optionally-substituted 1,2,3,4-tetrahydronaphth-1-yl, optionally-substituted 1,2,3,4-tetrahydronaphth-2-yl, the heterocycle Y', Y'—($C_1$-$C_4$ alkyl), $R^7R^8N$—, and $R^7R^8N$—($C_2$-$C_4$ alkyl); and $R^{5'}$ is selected from the group consisting of hydroxy, $C_1$-$C_6$ alkyl, $C_1$-$C_4$ alkoxycarbonyl, and benzyl; or $R^{5'}$ and X' are taken together with the attached nitrogen atom to form an optionally substituted heterocycle selected from the group consisting of pyrrolidinyl, piperidinyl, piperazinyl, and homopiperazinyl, where said heterocycle is optionally substituted with $R^{10}$, $R^{12'}$, $R^7R^8N$—, or $R^{7'}R^{8'N}$—($C_1$-$C_4$ alkyl);

where the heterocycle Y and the heterocycle Y' are each independently selected from the group consisting of tetrahydrofuryl, morpholinyl, pyrrolidinyl, piperidinyl, piperazinyl, homopiperazinyl, or quinuclidinyl; where said morpholinyl, pyrrolidinyl, piperidinyl, piperazinyl, homopiperazinyl, or quinuclidinyl is optionally N-substituted with $C_1$-$C_4$ alkyl or optionally-substituted aryl($C_1$-$C_4$ alkyl);

$R^7$ is hydrogen or $C_1$-$C_6$ alkyl; and $R^8$ is $C_1$-$C_6$ alkyl, $C_3$-$C_8$ cycloalkyl, optionally-substituted aryl, or optionally-substituted aryl($C_1$-$C_4$ alkyl); or $R^7$ and $R^8$ are taken together with the attached nitrogen atom to form an heterocycle selected from the group consisting of pyrrolidinyl, piperidinyl, morpholinyl, piperazinyl, and homopiperazinyl; where said piperazinyl or homopiperazinyl is optionally N-substitued with $R^{12}$;

$R^{7'}$ is hydrogen or $C_1$-$C_6$ alkyl; and $R^{8'}$ is $C_1$-$C_6$ alkyl, $C_3$-$C_8$ cycloalkyl, optionally-substituted aryl, or optionally-substituted aryl($C_1$-$C_4$ alkyl); or $R^{7'}$ and $R^{8'}$ are taken together with the attached nitrogen atom to form an heterocycle selected from the group consisting of pyrrolidinyl, piperidinyl, morpholinyl, piperazinyl, and homopiperazinyl; where said piperazinyl or homopiperazinyl is optionally N-substituted with $R^{12'}$;

$R^{10}$ and $R^{11}$ are each independently chosen from the group consisting of hydrogen, $C_1$-$C_6$ alkyl, $C_3$-$C_8$ cycloalkyl, $C_1$-$C_4$ alkoxycarbonyl, $C_1$-$C_5$ alkanoyloxy, benzyloxy, benzoyloxy, diphenylmethoxy, triphenylmethoxy, optionally-substituted aryl, and optionally-substituted aryl($C_1$-$C_4$ alkyl);

where the $C_1$-$C_6$ alkyl or the $C_3$-$C_8$ cycloalkyl is optionally monosubstituted with a substituent selected from the group consisting of hydroxy, protected carboxy, carbamoyl, thiobenzyl and $C_1$-$C_4$ thioalkyl; and, where the benzyl of said benzyloxy or said benzoyloxy is optionally substituted with one or two substituents independently selected from the group consisting of $C_1$-$C_4$ alkyl, $C_1$-$C_4$ alkoxy, halogen, hydroxy, cyano, carbamoyl, amino, mono($C_1$-$C_4$ alkyl)amino, di($C_1$-$C_4$ alkyl)amino, $C_1$-$C_4$ alkylsulfonylamino, and nitro; and $R^{12}$ and $R^{12'}$ are each independently selected from the group consisting of hydrogen, $C_1$-$C_6$ alkyl, $C_3$-$C_8$ cycloalkyl, $C_1$-$C_4$ alkoxycarbonyl, optionally-substituted aryloxycarbonyl, optionally-substituted aryl ($C_1$-$C_4$ alkyl), and optionally-substituted aryloyl; and providing that when A is XNH— and the integer n is 0, then A' is not anilinyl, substituted anilinyl, benzylamino, or substituted benzylamino.

2. The compound of claim 1 wherein A is XNH—.

3. The compound of claim 1 wherein A is $R^5XN$—; where $R^5$ is selected from the group consisting of hydroxy, $C_1$-$C_6$ alkyl, $C_1$-$C_4$ alkoxycarbonyl, and benzyl; and where X is selected from the group consisting of $C_1$-$C_6$ alkyl, $C_3$-$C_8$ cycloalkyl, ($C_1$-$C_4$ alkoxy)-($C_1$-$C_4$ alkyl), optionally-substituted aryl, optionally-substituted aryl($C_1$-$C_4$ alkyl), optionally-substituted aryl($C_3$-$C_7$ cycloalkyl), optionally-substituted indan-1-yl, optionally-substituted indan-2-yl, optionally-substituted 1,2,3,4-tetrahydronaphth-1-yl, optionally-substituted 1,2,3,4-tetrahydronaphth-2-yl, the heterocycle Y, Y—($C_1$-$C_4$ alkyl), $R^7R^8N$—, and $R^7R^8N$—($C_2$-$C_4$ alkyl).

4. The compound of claim 1 wherein A is $R^5XN$—, where $R^5$ and X are taken together with the attached nitrogen atom to form an optionally substituted heterocycle selected from the group consisting of pyrrolidinyl, piperidinyl, piperazinyl, and homopiperazinyl;

where said heterocycle is optionally substituted with $R^{10}$, $R^{12}$, $R^7R^8N$—, or $R^7R^8N$—($C_1$-$C_4$ alkyl).

5. The compound of claim 4 wherein $R^5$ and X are taken together with the attached nitrogen atom to form piperidinyl optionally substituted at the 4-position with hydroxy, $C_1$-$C_6$ alkyl, $C_3$-$C_8$ cycloalkyl, $C_1$-$C_4$ alkoxy, ($C_1$-$C_4$ alkoxy)carbonyl, (hydroxy($C_2$-$C_4$ alkyloxy))-($C_2$-$C_4$ alkyl), $R^7R^8N$—, $R^7R^8N$—($C_1$-$C_4$ alkyl), diphenylmethyl, optionally-substituted aryl, optionally-substituted aryl($C_1$-$C_4$ alkyl), or piperidin-1-yl($C_1$-$C_4$ alkyl).

6. The compound of claim 4 wherein $R^5$ and X are taken together with the attached nitrogen atom to form piperazinyl optionally substituted at the 4-position with $C_1$-$C_6$ alkyl, $C_3$-$C_8$ cycloalkyl, optionally-substituted aryl, optionally-substituted aryl($C_1$-$C_4$ alkyl), α-methylbenzyl, N—(C1-C5 alkyl) acetamid-2-yl, N—($C_3$-$C_8$ cycloalkyl) acetamid-2-yl, $R^7R^8N$—, or ($C_1$-$C_4$ alkoxy)carbonyl.

7. The compound of claim 4 wherein $R^5$ and X are taken together with the attached nitrogen atom to form homopiperazinyl optionally substituted in the 4-position with $C_1$-$C_4$ alkyl, aryl, or aryl($C_1$-$C_4$ alkyl).

8. The compound of claim 1 wherein A is $R^5XN$—, where $R^5$ and X are taken together with the attached nitrogen atom to form an heterocycle selected from the group consisting of pyrrolidinonyl, piperidinonyl, 2-(pyrrolidin-1-ylmethyl)pyrrolidin-1-yl, 1,2,3,4-tetrahydroisoquinolin-2-yl.

9. The compound of claim 1 wherein A' is X'NH—.

10. The compound of claim 1 wherein A' is $R^{5'}X'N$—; where $R^{5'}$ is selected from the group consisting of hydroxy, $C_1$-$C_6$ alkyl, $C_1$-$C_4$ alkoxycarbonyl, and benzyl; and X' is selected from the group consisting of $C_1$-$C_6$ alkyl, $C_3$-$C_8$ cycloalkyl, ($C_1$-$C_4$ alkoxy)-($C_1$-$C_4$ alkyl), optionally-substituted aryl, optionally-substituted aryl($C_1$-$C_4$ alkyl), optionally-substituted aryl($C_3$-$C_7$ cycloalkyl), optionally-substituted indan-1-yl, optionally-substituted indan-2-yl, optionally-substituted 1,2,3,4-tetrahydronaphth-1-yl, optionally-substituted 1,2,3,4-tetrahydronaphth-2-yl, the heterocycle Y', Y'—($C_1$-$C_4$ alkyl), $R^7R^8N$—, and $R^7R^8N$—($C_2$-$C_4$ alkyl).

11. The compound of claim 1 wherein A' is $R^{5'}X'N$—, where $R^{5'}$ and X' are taken together with the attached nitrogen atom to form an optionally substituted heterocycle selected from the group consisting of pyrrolidinyl, piperidinyl, piperazinyl, and homopiperazinyl;

where said heterocycle is optionally substituted with $R^{10}$, $R^{12'}$, $R^7R^8N$—, or $R^7R^8N$—($C_1$-$C_4$ alkyl).

12. The compound of claim 11 wherein $R^{5'}$ and X' are taken together with the attached nitrogen atom to form piperidinyl optionally substituted at the 4-position with hydroxy, $C_1$-$C_6$ alkyl, $C_3$-$C_8$ cycloalkyl, $C_1$-$C_4$ alkoxy, ($C_1$-$C_4$ alkoxy)carbonyl, (hydroxy($C_1$-$C_4$ alkyloxy))-($C_1$-$C_4$ alkyl), $R^7R^8N$—, $R^7R^8N$—($C_1$-$C_4$ alkyl), diphenylmethyl, optionally-substituted aryl, optionally-substituted aryl ($C_1$-$C_4$ alkyl), or piperidin-1-yl($C_1$-$C_4$ alkyl).

13. The compound of claim 11 wherein $R^{5'}$ and X' are taken together with the attached nitrogen atom to form piperazinyl optionally substituted at the 4-position with $C_1$-$C_6$ alkyl, $C_3$-$C_8$ cycloalkyl, optionally-substituted aryl, optionally-substituted aryl($C_1$-$C_4$ alkyl), α-methylbenzyl, N—(C1-C5 alkyl) acetamid-2-yl, N—($C_3$-$C_8$ cycloalkyl) acetamid-2-yl, $R^7R^8N$—, or ($C_1$-$C_4$ alkoxy)carbonyl.

14. The compound of claim 11 wherein $R^{5'}$ and X' are taken together with the attached nitrogen atom to form homopiperazinyl optionally substituted in the 4-position with $C_1$-$C_4$ alkyl, aryl, or aryl($C_1$-$C_4$ alkyl).

15. The compound of claim 1 wherein A' is $R^{5'}$X'N—, where $R^{5'}$ and X' are taken together with the attached nitrogen atom to form an heterocycle selected from the group consisting of pyrrolidinonyl, piperidinonyl, 2-(pyrrolidin-1-ylmethyl)pyrrolidin-1-yl, 1,2,3,4-tetrahydroisoquinolin-2-yl.

16. The compound of claim 2 wherein A' is X'NH—; where X' is selected from the group consisting of the heterocycle Y', Y'—($C_1$-$C_4$ alkyl), $R^7R^8N$—, and $R^7R^8N$-($C_2$-$C_4$ alkyl).

17. The compound of claim 16 wherein X is selected from the group consisting of optionally-substituted aryl($C_1$-$C_4$ alkyl), optionally-substituted aryl($C_3$-$C_7$ cycloalkyl), the heterocycle Y, Y—($C_1$-$C_4$ alkyl), $R^7R^8N$—, and $R^7R^8N$—($C_2$-$C_4$ alkyl).

18. The compound of claim 2 wherein A' is $R^{5'}$X'N—, where $R^{5'}$ and X' are taken together with the attached nitrogen atom to form an heterocycle selected from the group consisting of pyrrolidinyl, piperidinyl, piperazinyl, and homopiperazinyl;

where said heterocycle is optionally substituted with $R^{10}$, $R^{12'}$, $R^7R^8N$—, or $R^7R^8N$—($C_1$-$C_4$ alkyl).

19. The compound of claim 18 wherein X is selected from the group consisting of optionally-substituted aryl($C_1$-$C_4$ alkyl), optionally-substituted aryl($C_3$-$C_7$ cycloalkyl), the heterocycle Y, Y—($C_1$-$C_4$ alkyl), $R^7R^8N$—, and $R^7R^8N$—($C_2$-$C_4$ alkyl).

20. The compound of claim 2 wherein A' is X'NH—, or $R^{5'}$X'N—; and n is 1.

21. The compound of claim 2 wherein A' is X'NH—, or $R^{5'}$X'N—; and n is 2.

22. The compound of claim 9 wherein A is XNH—; where X is selected from the group consisting of the heterocycle Y, Y—($C_1$-$C_4$ alkyl), $R^7R^8N$—, and $R^7R^8N$—($C_2$-$C_4$-alkyl).

23. The compound of claim 22 wherein X' is selected from the group consisting of optionally-substituted aryl ($C_1$-$C_4$ alkyl), optionally-substituted aryl($C_3$-$C_7$ cycloalkyl), the heterocycle Y', Y'—($C_1$-$C_4$ alkyl), $R^7R^8N$—, and $R^7R^8N$—($C_2$-$C_4$ alkyl).

24. The compound of claim 9 wherein A is $R^5XN$—, where $R^5$ and X are taken together with the attached nitrogen atom to form an heterocycle selected from the group consisting of pyrrolidinyl, piperidinyl, piperazinyl, and homopiperazinyl;

where said heterocycle is optionally substituted with $R^{10}$, $R^{12'}$, $R^7R^8N$—, or $R^7R^8N$—($C_1$-$C_4$ alkyl).

25. The compound of claim 24 wherein X' is selected from the group consisting of optionally-substituted aryl ($C_1$-$C_4$ alkyl), optionally-substituted aryl($C_3$-$C_7$ cycloalkyl), the heterocycle Y', Y'—($C_1$-$C_4$ alkyl), $R^7R^8N$—, and $R^7R^8N$—($C_2$-$C_4$ alkyl).

26. The compound of claim 9 wherein A is XNH—, or $R^5XN$—; and n is 1.

27. The compound of claim 9 wherein A is XNH—, or $R^5XN$—; and n is 2.

28. The compound of claim 1 wherein A is $R^5XN$—, where $R^5$ and X are taken together with the attached nitrogen atom to form an heterocycle selected from the group consisting of pyrrolidinyl, piperidinyl, piperazinyl, and homopiperazinyl; where said heterocycle is optionally substituted with $R^{10}$, $R^{12}$, $R^7R^8N$—, or $R^7R^8N$—($C_1$-$C_4$ alkyl); and A' is $R^{5'}$X'N—, where $R^{5'}$ and X' are taken together with the attached nitrogen atom to form an heterocycle selected from the group consisting of pyrrolidinyl, piperidinyl, piperazinyl, and homopiperazinyl; where said heterocycle is optionally substituted with $R^{10}$, $R^{12'}$, $R^7R^8N$—, or $R^7R^8N$—($C_1$-$C_4$ alkyl) as defined above.

29. The compound of claim 28 wherein n is 1.

30. The compound of claim 28 wherein n is 2.

31. The compound of claim 1 wherein $R^4$ is optionally-substituted aryl($C_1$-$C_4$ alkyl), optionally-substituted aryl ($C_2$-$C_4$ alkenyl), or optionally-substituted aryl($C_2$-$C_4$ alkynyl).

32. The compound of claim 1 wherein $R^3$ is the structure

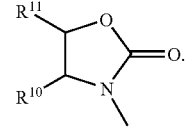

33. The compound of claim 1 wherein $R^2$ is hydrogen.

34. The compound of claim 1 wherein A is $R^5XN$—, where $R^5$ and X are taken together with the attached nitrogen atom to form an heterocycle selected from the group consisting of pyrrolidinyl, piperidinyl, and piperazinyl; where said heterocycle is optionally substituted with $C_1$-$C_6$ alkyl, $C_3$-$C_8$ cycloalkyl, $R^7R^8N$—, $R^7R^8N$—($C_1$-$C_4$ alkyl), optionally-substituted aryl, or optionally-substituted aryl($C_1$-$C_4$ alkyl).

35. The compound of claim 1 wherein A is XNH—, where X is optionally-substituted aryl($C_1$-$C_4$ alkyl).

36. The compound of claim 35 wherein $R^4$ is optionally-substituted aryl($C_1$-$C_4$ alkyl), optionally-substituted aryl ($C_2$-$C_4$ alkenyl), or optionally-substituted aryl($C_2$-$C_4$ alkynyl); $R^3$ is the structure

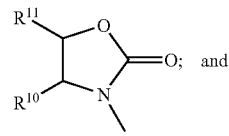

$R^2$ is hydrogen.

37. The compound of claim 36 wherein A' is X'NH—, where X' is optionally-substituted aryl($C_1$-$C_4$ alkyl), the heterocycle Y', Y'—($C_1$-$C_4$ alkyl), $R^{7'}R^{8'}N$—, or $R^{7'}R^{8'}N$—($C_2$-$C_4$ alkyl).

38. The compound of claim 37 wherein X' is $R^{7'}R^{8'}N$— or $R^{7'}R^{8'}N$—($C_2$-$C_4$ alkyl).

39. The compound of claim 37 wherein X' is the heterocycle Y' or Y'—($C_1$-$C_4$ alkyl), where said heterocycle Y' is selected from the group consisting of pyrrolidinyl, piperidinyl, morpholinyl, piperazinyl, and homopiperazinyl, where said heterocycle is optionally N-substituted with optionally-substituted aryl($C_1$-$C_4$ alkyl).

40. The compound of claim 37 wherein the integer n is 1.

41. The compound of claim 37 wherein $R^{8'}$ is selected from the group consisting of $C_1$-$C_6$ alkyl, $C_3$-$C_8$ cycloalkyl, and aryl($C_1$-$C_4$ alkyl).

42. The compound of claim 37 wherein $R^{7'}$ and $R^{8'}$ are taken together with the attached nitrogen atom to form an heterocycle selected from the group consisting of pyrrolidinyl, piperidinyl, morpholinyl, piperazinyl, and homopiperazinyl, where said piperazinyl or homopiperazinyl is optionally substituted at the 4-position with ($C_1$-$C_4$ alkyl), ($C_3$-$C_8$ cycloalkyl), or aryl($C_1$-$C_4$ alkyl).

43. The compound of claim 36 wherein A' is $R^{5'}X'N$—.

44. The compound of claim 43 wherein $R^{5'}$ is aryl($C_1$-$C_4$ alkyl), and X' is selected from the group consisting of optionally-substituted aryl($C_1$-$C_4$ alkyl), the heterocycle Y', Y'—($C_1$-$C_4$ alkyl), $R^{7'}R^{8'}N$—, and $R^{7'}R^{8'}N$—($C_2$-$C_4$ alkyl).

45. The compound of claim 43 wherein $R^{8'}$ is selected from the group consisting of $C_1$-$C_6$ alkyl, $C_3$-$C_8$ cycloalkyl, and aryl($C_1$-$C_4$ alkyl).

46. The compound of claim 43 wherein $R^{7'}$ and $R^{8'}$ are taken together with the attached nitrogen atom to form an heterocycle selected from the group consisting of pyrrolidinyl, piperidinyl, morpholinyl, piperazinyl, and homopiperazinyl, where said piperazinyl or homopiperazinyl is optionally substituted at the 4-position with ($C_1$-$C_4$ alkyl), ($C_3$-$C_8$ cycloalkyl), or aryl($C_1$-$C_4$ alkyl).

47. The compound of claim 43 wherein $R^{5'}$ and X' are taken together with the attached nitrogen atom to form an heterocycle selected from the group consisting of pyrrolidin-1-yl, piperidin-1-yl, piperazin-1-yl, and homopiperazin-1-yl; where said heterocycle is substituted with $C_1$-$C_6$ alkyl, $C_3$-$C_8$ cycloalkyl, optionally-substituted aryl, optionally-substituted aryl($C_1$-$C_4$ alkyl), the heterocycle Y', Y'—($C_1$-$C_4$ alkyl), $R^{7'}R^{8'}N$—, $R^{7'}R^{8'}N$—($C_1$-$C_4$ alkyl), or $R^{7'}R^{8'}N$—C(O)—($C_1$-$C_4$ alkyl).

48. The compound of claim 43 wherein $R^{5'}$ and X' are taken together with the attached nitrogen atom to form an heterocycle selected from the group consisting of piperidin-1-yl and piperazin-1-yl, where the heterocycle is substituted with $C_1$-$C_6$ alkyl, $C_3$-$C_8$ cycloalkyl, optionally-substituted aryl($C_1$-$C_4$ alkyl), $R^{7'}R^{8'}N$—, or $R^{7'}R^{8'}N$—($C_1$-$C_4$ alkyl).

49. The compound of claim 48 wherein $R^{7'}$ and $R^{8'}$ are taken together with the attached nitrogen atom to form an heterocycle selected from the group consisting of pyrrolidinyl, piperidinyl, morpholinyl, piperazinyl, and homopiperazinyl, where said piperazinyl or homopiperazinyl is optionally substituted at the 4-position with ($C_1$-$C_4$ alkyl), ($C_3$-$C_8$ cycloalkyl), or aryl($C_1$-$C_4$ alkyl).

50. The compound of claim 43 wherein $R^{5'}$ and X' are taken together with the attached nitrogen to form piperazin-1-yl, where said piperazin-1-yl is substituted with $C_1$-$C_6$ alkyl, $C_3$-$C_8$ cycloalkyl, or aryl($C_1$-$C_4$ alkyl).

51. The compound of claim 43 wherein the integer n is 1.

52. The compound of claim 43 wherein the integer n is 2.

53. A compound of the formula

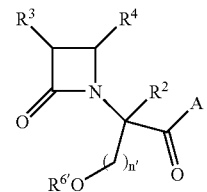

in a hydrate or solvate form, wherein:
n' is an integer from 1 to 3;
A is XNH—, or $R^5XN$—;
$R^2$ is hydrogen or $C_1$-$C_6$ alkyl;
$R^3$ is a structure selected from the group consisting of

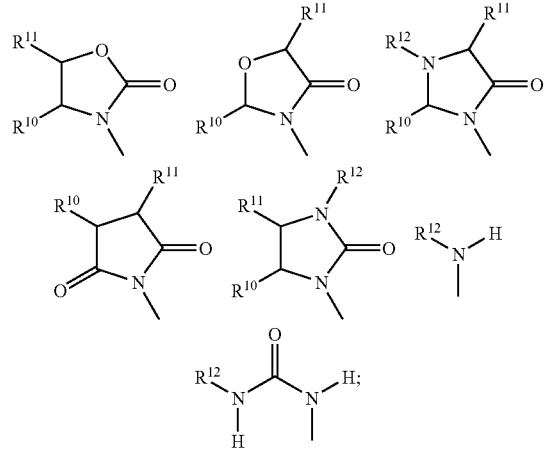

$R^4$ is $C_1$-$C_6$ alkyl, $C_2$-$C_6$ alkenyl, $C_2$-$C_6$ alkynyl, $C_3$-$C_8$ cycloalkyl, $C_3$-$C_9$ cycloalkenyl, limonenyl, pinenyl, $C_1$-$C_3$ alkanoyl, optionally-substituted aryl, optionally-substituted aryl($C_1$-$C_4$ alkyl), optionally-substituted aryl(halo $C_1$-$C_4$ alkyl), optionally-substituted aryl(alkoxy $C_1$-$C_4$ alkyl), optionally-substituted aryl($C_2$-$C_4$ alkenyl), optionally-substituted aryl(halo $C_2$-$C_4$ alkenyl), or optionally-substituted aryl($C_2$-$C_4$ alkynyl);

X is selected from the group consisting of $C_1$-$C_6$ alkyl, $C_3$-$C_8$ cycloalkyl, ($C_1$-$C_4$ alkoxy)-($C_1$-$C_4$ alkyl), optionally-substituted aryl, optionally-substituted aryl ($C_1$-$C_4$ alkyl), optionally-substituted aryl($C_3$-$C_7$ cycloalkyl), optionally-substituted indan-1-yl, optionally-substituted indan-2-yl, optionally-substituted 1,2,3,4-tetrahydronaphth-1-yl, optionally-substituted 1,2,3,4-tetrahydronaphth-2-yl, the heterocycle Y, Y—($C_1$-$C_4$ alkyl), $R^7R^8N$—, and $R^7R^8N$—($C_2$-$C_4$ alkyl); and $R^5$ is selected from the group consisting of hydroxy, $C_1$-$C_6$ alkyl, $C_1$-$C_4$ alkoxycarbonyl, and benzyl; and where X is selected from the group consisting of $C_1$-$C_6$ alkyl, $C_3$-$C_8$ cycloalkyl, ($C_1$-$C_4$ alkoxy)-($C_1$-$C_4$ alkyl), optionally-substituted aryl, optionally-substituted aryl ($C_1$-$C_4$ alkyl), optionally-substituted aryl($C_3$-$C_7$ cycloalkyl), optionally-substituted indan-1-yl, optionally-substituted indan-2-yl, optionally-substituted 1,2,3,4tetrahydronaphth-1-yl, optionally-substituted 1,2,3,4-tetrahydronaphth-2-yl, the heterocycle Y, Y—($C_1$-$C_4$ alkyl), $R^7R^8N$—, and $R^7R^8N$—($C_2$-$C_4$ alkyl); or $R^5$ and X are taken together with the attached nitrogen atom to form an optionally substituted heterocycle selected from the group consisting of pyrrolidinyl, piperidinyl, piperazinyl, and homopiperazinyl, where said heterocycle is optionally substituted with $R^{10}$, $R^{12}$, $R^7R^8N$—, or $R^7R^8N$—($C_1$-$C_4$ alkyl);

$R^{6'}$ is selected from the group consisting of $C_1$-$C_6$ alkyl, $C_3$-$C_8$ cycloalkyl, ($C_1$-$C_4$ alkoxy)-($C_1$-$C_4$ alkyl), optionally-substituted aryl($C_1$-$C_4$ alkyl), Y'—($C_1$-$C_4$ alkyl), and $R^7R^{8'}N$—($C_2$-$C_4$ alkyl);
where the heterocycle Y and the heterocycle Y' are each independently selected from the group consisting of tetrahydrofuryl, morpholinyl, pyrrolidinyl, piperidinyl, piperazinyl, homopiperazinyl, or quinuclidinyl; where said morpholinyl, pyrrolidinyl, piperidinyl, piperazinyl, homopiperazinyl, or quinuclidinyl is optionally N-substituted with $C_1$-$C_4$ alkyl or optionally-substituted aryl($C_1$-$C_4$ alkyl);

$R^7$ is hydrogen or $C_1$-$C_6$ alkyl; and $R^8$ is $C_1$-$C_6$ alkyl, $C_3$-$C_8$ cycloalkyl, optionally-substituted aryl, or optionally-substituted aryl($C_1$-$C_4$ alkyl); or $R^7$ and $R^8$ are taken together with the attached nitrogen atom to form an heterocycle selected from the group consisting of pyrrolidinyl, piperidinyl, morpholinyl, piperazinyl, and homopiperazinyl; where said piperazinyl or homopiperazinyl is optionally N-substitued with $R^{12}$;

$R^{7'}$ is hydrogen or $C_1$-$C_6$ alkyl; and $R^{8'}$ is $C_1$-$C_6$ alkyl, $C_3$-$C_8$ cycloalkyl, optionally-substituted aryl, or optionally-substituted aryl($C_1$-$C_4$ alkyl); or $R^{7'}$ and $R^{8'}$ are taken together with the attached nitrogen atom to form an heterocycle selected from the group consisting of pyrrolidinyl, piperidinyl, morpholinyl, piperazinyl, and homopiperazinyl; where said piperazinyl or homopiperazinyl is optionally N-substituted with $R^{12'}$;

$R^{10}$ and $R^{11}$ are each independently chosen from the group consisting of hydrogen, $C_1$-$C_6$ alkyl, $C_3$-$C_8$ cycloalkyl, $C_1$-$C_4$ alkoxycarbonyl, $C_1$-$C_5$ alkanoyloxy, benzyloxy, benzoyloxy, diphenylmethoxy, triphenylmethoxy, optionally-substituted aryl, and optionally-substituted aryl($C_1$-$C_4$ alkyl);
where the $C_1$-$C_6$ alkyl or the $C_3$-$C_8$ cycloalkyl is optionally monosubstituted with a substituent selected from the group consisting of hydroxy, protected carboxy, carbamoyl, thiobenzyl and $C_1$-$C_4$ thioalkyl; and,
where the benzyl of said benzyloxy or said benzoyloxy is optionally substituted with one or two substituents independently selected from the group consisting of $C_1$-$C_4$ alkyl, $C_1$-$C_4$ alkoxy, halogen, hydroxy, cyano, carbamoyl, amino, mono($C_1$-$C_4$ alkyl)amino, di($C_1$-$C_4$ alkyl)amino, $C_1$-$C_4$ alkylsulfonylamino, and nitro; and $R^{12}$ and $R^{12'}$ are each independently selected from the group consisting of hydrogen, $C_1$-$C_6$ alkyl, $C_3$-$C_8$ cycloalkyl, $C_1$-$C_4$ alkoxycarbonyl, optionally-substituted aryloxycarbonyl, optionally-substituted aryl ($C_1$—$C_4$ alkyl), and optionally-substituted aryloyl.

54. The compound of claim 52 wherein A is XNH—.

55. The compound of claim 53 wherein A is $R^5XN$—; where $R^5$ is selected from the group consisting of hydroxy, $C_1$-$C_6$ alkyl, $C_1$-$C_4$ alkoxycarbonyl, and benzyl; and where X is selected from the group consisting of $C_1$-$C_6$ alkyl, $C_3$-$C_8$ cycloalkyl, ($C_1$-$C_4$ alkoxy)-($C_1$-$C_4$ alkyl), optionally-substituted aryl, optionally-substituted aryl($C_1$-$C_4$ alkyl), optionally-substituted aryl($C_3$-$C_7$ cycloalkyl), optionally-substituted indan-1-yl, optionally-substituted indan-2-yl, optionally-substituted 1,2,3,4-tetrahydronaphth-1-yl, optionally-substituted 1,2,3,4-tetrahydronaphth-2-yl, the heterocycle Y, Y—($C_1$-$C_4$ alkyl), $R^7R^8N$—, and $R^7R^8N$—($C_2$-$C_4$ alkyl).

56. The compound of claim 53 wherein A is $R^5XN$—, where $R^5$ and X are taken together with the attached nitrogen atom to form an heterocycle selected from the group consisting of pyrrolidinyl, piperidinyl, piperazinyl, and homopiperazinyl;
where said heterocycle is optionally substituted with $R^{10}$, $R^{12}$, $R^7R^8N$—, or $R^7R^8N$—($C_1$-$C_4$ alkyl).

57. The compound of claim 56 wherein $R^5$ and X are taken together with the attached nitrogen atom to form piperidinyl optionally substituted at the 4-position with hydroxy, $C_1$-$C_6$ alkyl, $C_3$-$C_8$ cycloalkyl, $C_1$-$C_4$ alkoxy, ($C_1$-$C_4$ alkoxy)carbonyl, (hydroxy($C_2$-$C_4$ alkyloxy))-($C_2$-$C_4$ alkyl), $R^7R^8N$—, $R^7R^8N$—($C_1$-$C_4$ alkyl), diphenylmethyl, optionally-substituted aryl, optionally-substituted aryl ($C_1$-$C_4$ alkyl), or piperidin-1-yl($C_1$-$C_4$ alkyl).

58. The compound of claim 56 wherein $R^5$ and X are taken together with the attached nitrogen atom to form piperazinyl optionally substituted at the 4-position with $C_1$-$C_6$ alkyl, $C_3$-$C_8$ cycloalkyl, optionally-substituted aryl, optionally-substituted aryl($C_1$-$C_4$ alkyl), α-methylbenzyl, N—(C1-C5 alkyl) acetamid-2-yl, N—($C_3$-$C_8$ cycloalkyl) acetamid-2-yl, $R^7R^8N$—, or ($C_1$-$C_4$ alkoxy)carbonyl.

59. The compound of claim 56 wherein $R^5$ and X are taken together with the attached nitrogen atom to form homopiperazinyl optionally substituted in the 4-position with $C_1$-$C_4$ alkyl, aryl, or aryl($C_1$-$C_4$ alkyl).

60. The compound of claim 53 wherein A is $R^5XN$—, where $R^5$ and X are taken together with the attached nitrogen atom to form an heterocycle selected from the group consisting of pyrrolidinonyl, piperidinonyl, 2-(pyrrolidin-1-yl-methyl)pyrrolidin-1-yl, 1,2,3,4-tetrahydroisoquinolin-2-yl.

61. The compound of claim 53 wherein $R^4$ is optionally-substituted aryl($C_1$-$C_4$ alkyl), optionally-substituted aryl ($C_2$-$C_4$ alkenyl), or optionally-substituted aryl($C_2$-$C_4$ alkynyl).

62. The compound of claim 53 wherein $R^3$ is the structure

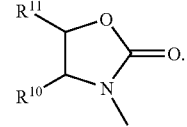

63. The compound of claim 53 wherein $R^2$ is hydrogen.

64. The compound of claim 53 wherein A is $R^5XN$—, where $R^5$ and X are taken together with the attached nitrogen atom to form an heterocycle selected from the group consisting of pyrrolidinyl, piperidinyl, and piperazinyl; where said heterocycle is optionally substituted with $C_1$-$C_6$ alkyl, $C_3$-$C_8$ cycloalkyl, $R^7R^8N$—, $R^7R^8N$—($C_1$-$C_4$ alkyl), optionally-substituted aryl, or optionally-substituted aryl($C_1$-$C_4$ alkyl).

65. The compound of claim 53 wherein A is XNH—, where X is optionally-substituted aryl($C_1$-$C_4$ alkyl).

66. The compound of claim 65 wherein $R^2$ is hydrogen; $R^4$ is optionally-substituted aryl($C_1$-$C_4$ alkyl), optionally-substituted aryl($C_2$-$C_4$ alkenyl), or optionally-substituted aryl($C_2$-$C_4$ alkynyl); and $R^3$ is the structure

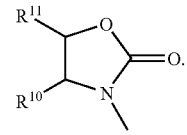

67. The compound of claim 53 wherein the integer n' is 1.

68. The compound of claim 53 wherein the integer n' is 2.

69. A pharmaceutical formulation comprising a compound of claim 1, and a pharmaceutically acceptable carrier, diluent, or excipient therefor.

70. A pharmaceutical formulation comprising a compound of claim 53, and a pharmaceutically acceptable carrier, diluent, or excipient therefor.

* * * * *

UNITED STATES PATENT AND TRADEMARK OFFICE
CERTIFICATE OF CORRECTION

PATENT NO. : 7,268,125 B2
APPLICATION NO. : 11/442788
DATED : September 11, 2007
INVENTOR(S) : Robert F. Bruns, Jr. et al.

It is certified that error appears in the above-identified patent and that said Letters Patent is hereby corrected as shown below:

Column 77, line 19, please replace that portion of the formula that reads "(C1-C5 alkyl)" with --($C_1$-$C_5$ alkyl)--.

Column 81, line 48, please replace the number "52" with --53--.

Column 82, line 14, please replace that portion of the formula that reads "(C1-C5 alkyl)" with --($C_1$-$C_5$ alkyl)--.

Signed and Sealed this

Twenty-fifth Day of December, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,268,125 B2 |
| APPLICATION NO. | : 11/442788 |
| DATED | : September 11, 2007 |
| INVENTOR(S) | : Robert F. Bruns et al. |

It is certified that error appears in the above-identified patent and that said Letters Patent is hereby corrected as shown below:

In the Specification

In column 1, line 18 "This invention was made with support from NIH Grant Nos. R41 HD37290 and R42 HD37290; the government may have certain rights in this invention." should read --This invention was made with government support under R41 HD37290 and R42 HD37290 awarded by the National Institutes of Health. The government has certain rights in the invention.--

Signed and Sealed this
Twenty-second Day of December, 2015

Michelle K. Lee
*Director of the United States Patent and Trademark Office*